United States Patent
Ohashi et al.

(10) Patent No.: US 7,670,751 B2
(45) Date of Patent: *Mar. 2, 2010

(54) PHOTOACID GENERATOR, RESIST COMPOSITION, AND PATTERNING PROCESS

(75) Inventors: Masaki Ohashi, Joetsu (JP); Youichi Ohsawa, Joetsu (JP); Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/204,685

(22) Filed: Sep. 4, 2008

(65) Prior Publication Data

US 2009/0061358 A1 Mar. 5, 2009

(30) Foreign Application Priority Data

Sep. 5, 2007 (JP) .............................. 2007-230363

(51) Int. Cl.
G03F 7/00 (2006.01)
G03F 7/004 (2006.01)

(52) U.S. Cl. .................... 430/270.1; 430/913
(58) Field of Classification Search .............. 430/270.1, 430/913
See application file for complete search history.

(56) References Cited

U.S. PATENT DOCUMENTS

| 5,635,332 | A | 6/1997 | Nakano et al. |
| 5,650,483 | A | 7/1997 | Malik et al. |
| 5,705,702 | A | 1/1998 | Osawa et al. |
| 5,714,625 | A | 2/1998 | Hada et al. |
| 6,048,672 | A | 4/2000 | Cameron et al. |
| 6,063,953 | A | 5/2000 | Hada et al. |
| 6,136,502 | A | 10/2000 | Satoshi et al. |
| 6,261,738 | B1 | 7/2001 | Asakura et al. |
| 6,306,555 | B1 | 10/2001 | Schulz et al. |
| 6,312,867 | B1 | 11/2001 | Kinsho et al. |
| 6,440,634 | B1 | 8/2002 | Ohsawa et al. |
| 6,512,020 | B1 | 1/2003 | Asakura et al. |
| 6,723,483 | B1 | 4/2004 | Oono et al. |
| 6,830,866 | B2 | 12/2004 | Kobayashi et al. |
| 6,849,374 | B2 | 2/2005 | Cameron et al. |
| 6,893,792 | B2 | 5/2005 | Miya et al. |
| 7,304,175 | B2 | 12/2007 | Harada et al. |

(Continued)

FOREIGN PATENT DOCUMENTS

EP 0473547 A1 3/1992

(Continued)

OTHER PUBLICATIONS

Dammel et al., Journal of Photopolymer Science and Technology, vol. 17, No. 4, 2004, pp. 587-601.

(Continued)

*Primary Examiner*—Amanda C. Walke
(74) *Attorney, Agent, or Firm*—Birch, Stewart, Kolasch & Birch, LLP.

(57) ABSTRACT

Photoacid generators generate sulfonic acids of formula (1a) or (1c) upon exposure to high-energy radiation.

$$R^1\text{—COOCH}(CF_3)CF_2SO_3^-H^+ \quad (1a)$$

$$R^1\text{—O—COOCH}(CF_3)CF_2SO_3^-H^+ \quad (1c)$$

$R^1$ is a $C_{20}$-$C_{50}$ hydrocarbon group having a steroid structure. The photoacid generators are compatible with resins and can control acid diffusion and are thus suited for use in chemically amplified resist compositions.

18 Claims, 18 Drawing Sheets

U.S. PATENT DOCUMENTS

| | | |
|---|---|---|
| 7,381,842 B2 | 6/2008 | Kunimoto et al. |
| 7,399,577 B2 | 7/2008 | Yamato et al. |
| 2002/0197558 A1 | 12/2002 | Ferreira et al. |
| 2003/0113659 A1 | 6/2003 | Hatakeyama et al. |
| 2004/0260031 A1 | 12/2004 | Takeda et al. |
| 2006/0040203 A1 | 2/2006 | Kodama et al. |
| 2006/0228648 A1 | 10/2006 | Ohsawa et al. |
| 2007/0003871 A1 | 1/2007 | Kodama et al. |
| 2007/0122750 A1 | 5/2007 | Yamaguchi et al. |
| 2007/0231738 A1 | 10/2007 | Kaneko et al. |
| 2008/0026331 A1 | 1/2008 | Hasegawa et al. |
| 2008/0124652 A1* | 5/2008 | Nishi et al. ............... 430/270.1 |
| 2008/0268370 A1* | 10/2008 | Tanaka et al. ............ 430/270.1 |

FOREIGN PATENT DOCUMENTS

| | | |
|---|---|---|
| EP | 1710230 A1 | 10/2006 |
| JP | 4-230645 A | 8/1992 |
| JP | 7-25846 A | 1/1995 |
| JP | 8-311018 A | 11/1996 |
| JP | 9-15848 A | 1/1997 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 11-190904 A | 7/1999 |
| JP | 2000-122296 A | 4/2000 |
| JP | 2000-336121 A | 5/2000 |
| JP | 2000-314956 A | 11/2000 |
| JP | 2001-122850 A | 5/2001 |
| JP | 2001-181221 A | 7/2001 |
| JP | 2001-233842 A | 8/2001 |
| JP | 2002-193887 A | 7/2002 |
| JP | 2002-193925 A | 7/2002 |
| JP | 2002-214774 A | 7/2002 |
| JP | 2003-66612 A1 | 3/2003 |
| JP | 2003-107706 A | 4/2003 |
| JP | 2003-252855 A | 9/2003 |
| JP | 2004-2252 A | 1/2004 |
| JP | 2004-4561 A | 1/2004 |
| JP | 2004-115630 A | 4/2004 |
| JP | 2004-531749 A | 10/2004 |
| JP | 2005-8766 A | 1/2005 |
| JP | 2005-084365 A | 3/2005 |
| JP | 2005-266766 A | 9/2005 |
| JP | 2006-257078 A | 9/2006 |
| JP | 2007-145797 A | 6/2007 |
| JP | 2007-161707 A | 6/2007 |
| JP | 2007-297590 A | 11/2007 |
| JP | 2008-031298 A1 | 2/2008 |
| WO | WO-2004/074242 | 9/2004 |
| WO | WO-2005/083890 A | 9/2005 |

OTHER PUBLICATIONS

P.A. Lowe, Synthesis of sulphonium salts, The Chemistry of the Sulphonium group Part 1. John-Wiley & Sons, Chapter 11, pp. 268-312, 1981.

DeVoe et al., Advances in Photochemistry, Photochemistry and Photophysics of Onium Salts, vol. 17, pp. 313-321, 1992. ISBN 0-471-81526-8.

Miller et al., Journal of Org. Chem., vol. 53, No. 23, 1988, pp. 5571-5573.

Arimitsu et al., Journal of Photopolynner Science and Technology, vol. 8, No. 1, pp. 43-46, 1995.

Arimitsu et al., Journal of Photopolymer Science and Technology, vol. 9, No. 1, pp. 29-30, 1996.

* cited by examiner

PHOTOACID GENERATOR, RESIST COMPOSITION, AND PATTERNING PROCESS

CROSS-REFERENCE TO RELATED APPLICATION

This non-provisional application claims priority under 35 U.S.C. §119(a) on Patent Application No. 2007-230363 filed in Japan on Sep. 5, 2007, the entire contents of which are hereby incorporated by reference.

TECHNICAL FIELD

This invention relates to novel photoacid generators, resist compositions comprising the same, and a patterning process using the same.

BACKGROUND OF THE INVENTION

While a number of recent efforts are being made to achieve a finer pattern rule in the drive for higher integration and operating speeds in LSI devices, DUV and VUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerin) between the projection lens and the wafer, allowing the projection lens to be designed to a numerical aperture (NA) of 1.0 or higher and achieving a higher resolution. See Journal of Photopolymer Science and Technology, Vol. 17, No. 4, p 587 (2004).

In the photolithography using an ArF excimer laser (wavelength 193 nm) as the light source, a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymers, and hydrogenated ring-opening metathesis polymers have been proposed as the base resin. This choice is effective to some extent in that the transparency of a resin alone is increased.

Studies have also been made on photoacid generators. In prior art chemically amplified resist compositions for lithography using KrF excimer laser, photoacid generators capable of generating alkane- or arene-sulfonic acid are used. However, the use of these photoacid generators in chemically amplified resist compositions for ArF lithography results in an insufficient acid strength to scissor acid labile groups on the resin, a failure of resolution or a low sensitivity. Thus these photoacid generators are not suited for the fabrication of microelectronic devices.

For the above reason, photoacid generators capable of generating perfluoroalkanesulfonic acid having a high acid strength are generally used in ArF chemically amplified resist compositions. These photoacid generators capable of generating perfluoroalkanesulfonic acid have already been developed for use in the KrF resist compositions. For instance, JP-A 2000-122296 and U.S. Pat. No. 6,048,672 (or JP-A 11-282168) describe photoacid generators capable of generating perfluorohexanesulfonic acid, perfluorooctanesulfonic acid, perfluoro-4-ethylcyclohexanesulfonic acid, and perfluorobutanesulfonic acid. JP-A 2002-214774, US Patent Application Publication 2003-0113659 Al (JP-A 2003-140332), and US Patent Application Publication 2002-0197558 A1 describe novel photoacid generators capable of generating perfluoroalkyl ether sulfonic acids.

On the other hand, perfluorooctanesulfonic acid and homologues thereof (collectively referred to as PFOS) are considered problematic with respect to their stability (or non-degradability) due to C—F bonds, and biological concentration and accumulation due to hydrophobic and lipophilic natures. The US EPA adopted Significant New Use Rule, listing 13 PPOS-related chemical substances and further listing 75 chemical substances although their use in the photoresist field is excluded. It has already been proposed to apply the Rule to perfluoroalkanesulfonic acids and derivatives thereof, summing to 183 chemical substances.

Facing the PFOS-related problems, manufacturers made efforts to develop partially fluorinated alkane sulfonic acids having a reduced degree of fluorine substitution. For instance, JP-A 2004-531749 describes the development of α,α-difluoroalkanesulfonic acid salts from α,α-difluoroalkene and a sulfur compound and discloses a resist composition comprising a photoacid generator which generates such sulfonic acid upon irradiation, specifically di(4-tert-butylphenyl)iodonium 1,1-difluoro-2-(1-naphthyl)-ethanesulfonate. JP-A 2004-2252 describes the development of α,α,β,β-tetrafluoroalkanesulfonic acid salts from α,α,β,β-tetrafluoro-α-iodoalkane and sulfur compound and discloses a photoacid generator capable of generating such a sulfonic acid and a resist composition comprising the same. JP-A 2002-214774 discloses such photoacid generators having difluorosulfoacetic acid alkyl esters (e.g., 1-(alkoxycarbonyl)-1,1-difluoromethanesulfonate) and difluorosulfoacetic acid amides (e.g., 1-carbamoyl-1,1-difluoromethanesulfonate) although their synthesis method is lacking. Furthermore, JP-A 2005-266766 discloses a photosensitive composition comprising a compound capable of generating a partially fluorinated alkane sulfonic acid having a sulfonylamide structure derived from perfluoroalkylene disulfonyl difluoride.

The substances disclosed in these patents have a reduced degree of fluorine substitution, but suffer from several problems. They are less degradable because they are lo based on substantially undegradable hydrocarbon skeletons and they do not possess readily degradable substituent groups such as ester groups. A certain limit is imposed on the molecular design for changing the size of alkanesulfonic acid. The starting materials containing fluorine are expensive.

JP-A 2007-145797 discloses $C_1$-$C_{20}$ alkanecarbonyloxy or arenecarbonyloxy-1,1,3,3,3-pentafluoropropanesulfonates, typically triphenylsulfonium 2-(adamantane-1-carbonyloxy)-1,1,3,3,3-pentafluoropropanesulfonate. The control of diffusion is still insufficient.

JP-A 2007-161707 discloses photoacid generators capable of generating partially fluorinated alkanesulfonic acids having a polycyclic hydrocarbon group. In our experiments, they are poorly soluble in resist solvents and thus practically unacceptable.

With respect to the immersion lithography, there remain some problems. Minute water droplets are left on the resist and wafer after the immersion exposure, which can often cause damages and defects to the resist pattern profile. The resist pattern after development can collapse or deform into a T-top profile. There exists a need for a patterning process which can form a satisfactory resist pattern after development according to the immersion lithography.

In forming fine feature size patterns, the problem of pattern density dependency, that is, the size difference between isolated and grouped patterns having different optical contrast becomes significant. Using a photoacid generator capable of generating an acid with low diffusion, the problem of pattern density dependency can be overcome to some extent, but not to a satisfactory extent. Since a certain variation of exposure dose can occur in the practical fabrication of microelectronic devices, the resist composition is required to have an exposure latitude that maintains a substantially identical pattern profile even on a certain variation of the exposure dose. While the resist composition is required to achieve a further reduction of the pattern rule as well as a good balance of sensitivity, substrate adhesion, and etching resistance, it is also required to ameliorate the pattern density dependency and exposure latitude without sacrifice of resolution.

DISCLOSURE OF THE INVENTION

The photoacid generator (PAG) produces an acid which must satisfy many requirements including a sufficient acid strength to cleave acid labile groups in a resist material, stability in the resist material during shelf storage, an adequate diffusion in the resist material, low volatility, minimal leach-out in water, little foreign matter left after development and resist removal, and good degradability in that it is decomposed away after the expiration of its role in lithography without imposing a load to the environment. No acids produced by prior art PAGs satisfy these requirements. Moreover, resist compositions using prior art photoacid generators fail to solve the problems of pattern density dependency and exposure latitude without sacrifice of resolution.

An object of the invention is to solve the problems of prior art photoacid generators, and to provide novel photoacid generators suited for use in resist materials which generators are effective in the ArF immersion lithography due to minimized leach-out in water and controlled formation of foreign matter inherent to the immersion lithography, and overcome the problems of pattern density dependency and exposure latitude. Another object is to provide a resist composition using the photoacid generator, and a patterning process.

The inventors have found that by starting with 1,1,1,3,3,3-hexafluoro-2-propanol which is readily available in the industry, compounds having 1,1,3,3,3-pentafluoro-2-acyloxypropane-1-sulfonate or 1,1,3,3,3-pentafluoro-2-alkyloxycarbonyloxypropane-1-sulfonate having a steroid structure can be prepared, and that these compounds, typically onium salts, oximes and imides are effective photoacid generators in chemically amplified resist compositions. The present invention is predicated on this finding.

The present invention provides novel photoacid generators, resist compositions and a patterning process, defined below.

[1] A photoacid generator for chemically amplified resist compositions which generates a sulfonic acid in response to high-energy radiation selected from UV, deep-UV, EUV, electron beam, x-ray, excimer laser, gamma-ray and synchrotron radiation, said sulfonic acid having the general formula (1a) or (1c):

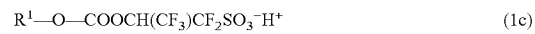

wherein $R^1$ is a $C_{20}$-$C_{50}$ hydrocarbon group having a steroid structure.

[2] The photoacid generator of [1] which generates a sulfonic acid having the following structural formula (1d) or (1e).

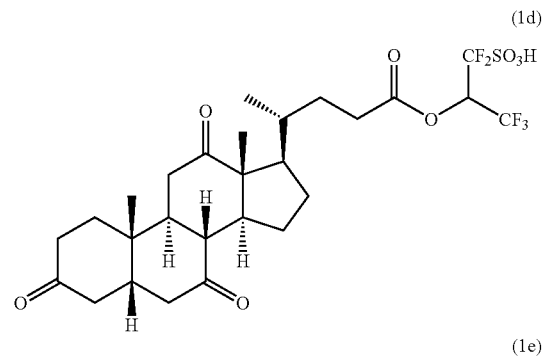

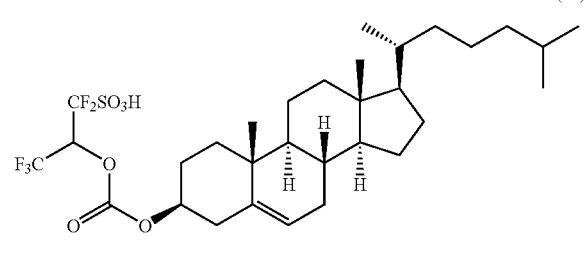

[3] A sulfonium salt having the general formula (2a) or (2c).

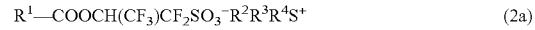

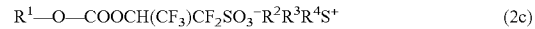

Herein $R^1$ is a $C_{20}$-$C_{50}$ hydrocarbon group having a steroid structure, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxyalkyl group, or at least two of $R^2$, R3 and $R^4$ may bond together to form a ring with the sulfur atom.

[4] A sulfonium salt having the general formula (3a) or (3c).

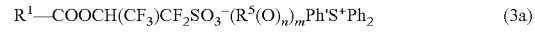

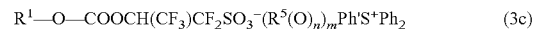

Herein $R^1$ is a $C_{20}$-$C_{50}$ hydrocarbon group having a steroid structure, $R^5$ is a substituted or unsubstituted, straight, branched or cyclic $C_1$-$C_{20}$ alkyl or alkenyl group or a substituted or unsubstituted $C_1$-$C_{14}$ aryl group, m is an integer of 1 to 5, n is 0 or 1, Ph denotes phenyl, and Ph' denotes a phenyl group in which a number "m" of hydrogen atoms are substituted by $R^5(O)_n$— groups.

[5] A iodonium salt having the general formula (4a) or (4c).

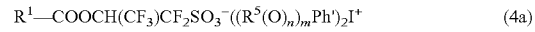

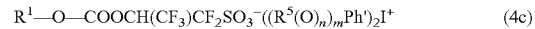

Herein $R^1$ is a $C_{20}$-$C_{50}$ hydrocarbon group having a steroid structure, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, and Ph' denotes a phenyl group in which a number "m" of hydrogen atoms are substituted by $R^5(O)_n$— groups.

[6] An N-sulfonyloxyimide compound having the general formula (5a) or (5c).

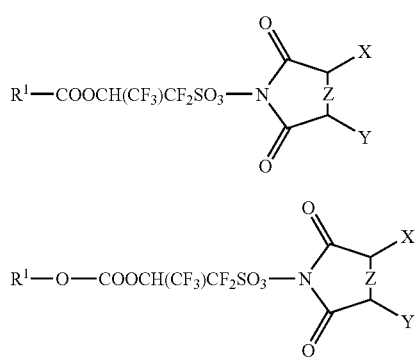

Herein $R^1$ is a $C_{20}$-$C_{50}$ hydrocarbon group having a steroid structure, X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene or oxygen atom.

[7] An oxime sulfonate compound having the general formula (6a) or (6c).

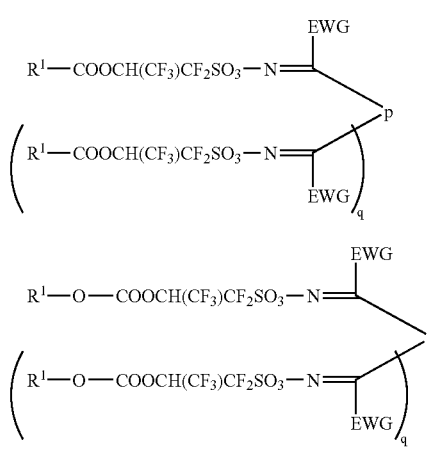

Herein $R^1$ is a $C_{20}$-$C_{50}$ hydrocarbon group having a steroid structure; q is 0 or 1; when q is 0, p is a substituted or unsubstituted $C_1$-$C_{20}$ alkyl group or a substituted or unsubstituted $C_6$-$C_{15}$ aryl group; when q is 1, p is a single bond, a substituted or unsubstituted $C_1$-$C_{20}$ alkylene group or a substituted or unsubstituted $C_6$-$C_{15}$ arylene group; EWG is a cyano, trifluoromethyl, perfluoroethyl, perfluoropropyl, 5H-perfluoropentyl, 6H-perfluorohexyl, nitro or methyl group, and when q is 1, two EWG's may bond together to form a ring of 6 carbon atoms with the carbon atoms to which they are attached.

[8] 0 A resist composition comprising a base resin, an acid generator, and an organic solvent, said acid generator comprising a photoacid generator which generates a sulfonic acid having formula (1a) or (1c) as set forth in [1].

[9] A resist composition comprising a base resin, an acid generator, and an organic solvent, said acid generator comprising a photoacid generator which generates a sulfonic acid having the following structural formula (1d) or (1e) as set forth in [2].

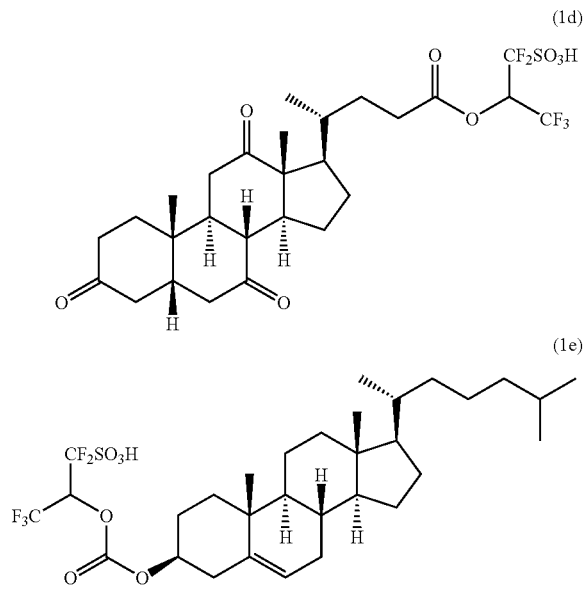

[10] The resist composition of [8] or [9], wherein said base resin is one or more polymers selected from the group consisting of poly(meth)acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers.

[11] The resist composition of [8] or [9], wherein said base resin is a polymeric structure containing silicon atoms.

[12] The resist composition of [8] or [9], wherein said base resin is a polymeric structure containing fluorine atoms.

[13] A chemically amplified positive resist composition comprising a base resin as set forth in [10], [11] or [12], a photoacid generator which generates a sulfonic acid having formula (1a) or (1c) as set forth in [1], and a solvent, wherein said base resin is insoluble or substantially insoluble in a liquid developer, and becomes soluble under the action of the acid.

[14] A chemically amplified positive resist composition comprising a base resin as set forth in [10], [11] or [12], a photoacid generator which generates a sulfonic acid having formula (1d) or (1e) as set forth in [2], and a solvent, wherein said base resin is insoluble or substantially insoluble in a liquid developer, and becomes soluble under the action of the acid.

[15] The chemically amplified positive resist composition of [13] or [14], further comprising a quencher.

[16] The chemically amplified positive resist composition of [13], [14] or [15], further comprising a dissolution inhibitor.

[17] A process for forming a pattern comprising the steps of applying the resist composition of any one of [8] to [16] onto a substrate to form a coating; heat treating the coating and exposing it to high-energy radiation having a wavelength of up to 300 nm through a photomask; and optionally heat treating and developing the exposed coating with a developer.

[18] The process of [17], wherein the exposing step relies on immersion lithography comprising directing radiation from an ArF excimer laser having a wavelength of 193 nm through a projection lens, with a liquid such as water, glycerin or ethylene glycol intervening between the coated substrate and the projection lens.

BENEFITS OF THE INVENTION

Since the photoacid generators of the invention include a bulky steroid structure in the sulfonate, they enable to adequately control acid diffusion and are fully compatible with resins and other components in resist compositions. The photoacid generators that generate these sulfonic acids perform well without raising problems during the device fabrication process including coating, pre-baking, exposure, post-exposure baking, and developing steps. They solve the problems of pattern density dependency and exposure latitude. The leach-out of sulfonic acids in water during the ArF immersion lithography is minimized. The influence of water left on the wafer is minimized, restraining defects from forming. In the disposal of resist-containing waste liquid after the device fabrication, acyloxy or alkylcarbonate groups at β-position are hydrolyzable under basic conditions so that the sulfonic acids are transformed into less accumulative fluorine compounds of lower molecular weight. In the disposal by combustion, the sulfonic acids are more combustible because of a low degree of fluorine substitution.

DESCRIPTION OF THE PREFERRED EMBODIMENTS

Figure 1:
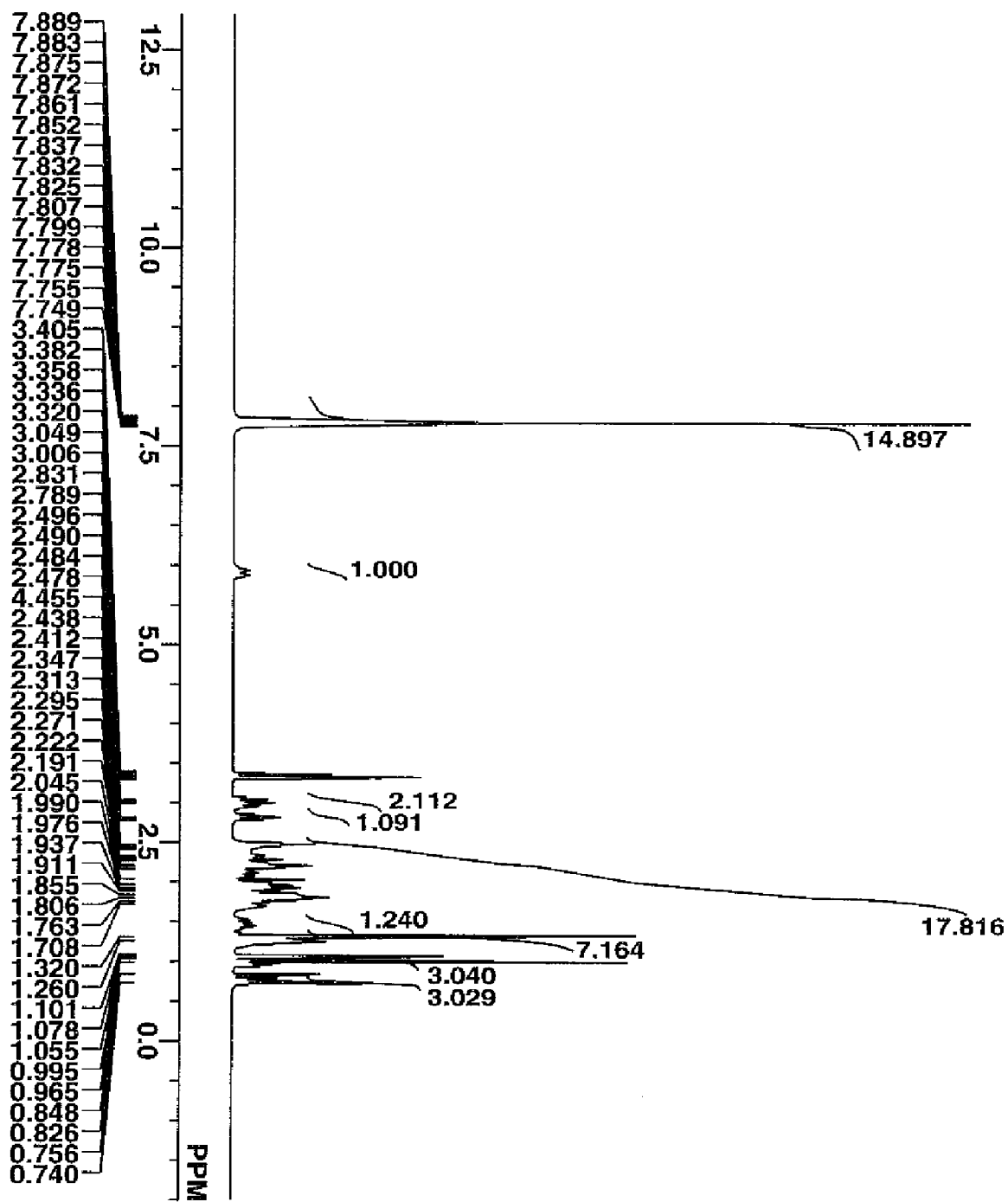
FIG. 1 is a diagram showing the $^1$H-NMR/DMSO-$d_6$ spectrum of PAG-A in Synthesis Example 1-19.

The singular forms "a," "an" and "the" include plural references unless the context clearly dictates otherwise.
The notation (Cn-Cm) means a group containing from n to m carbon atoms per group.

Photoacid Generator

The photoacid generators of the invention are compounds, typically sulfonium salts, iodonium salts, oxime sulfonates and sulfonyloxyimides. These compounds are sensitive to high-energy radiation such as UV, deep-UV, EUV, electron beam, x-ray, excimer laser, gamma-ray and synchrotron radiation and generate sulfonic acids having the general formula (1a) or (1c) in response to high-energy radiation, so that they are useful as photoacid generators in chemically amplified resist compositions.

$$R^1\text{---}COOCH(CF_3)CF_2SO_3^-H^+ \quad (1a)$$

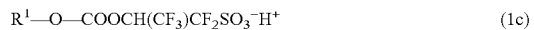

$$R^1\text{---}O\text{---}COOCH(CF_3)CF_2SO_3^-H^+ \quad (1c)$$

Herein $R^1$ is a $C_{20}$-$C_{50}$ hydrocarbon group having a steroid structure.

As used herein, the term "steroid structure" generally designates compounds of the structure having three six-membered rings and one five-membered ring fused together as represented by the general formula (7).

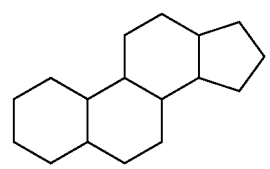

(7)

In formula (1a) or (1c), $R^1$ denotes a substituted or unsubstituted hydrocarbon group of 20 to 50 carbon atoms having a steroid structure. In a preferred embodiment, the sulfonic acids represented by formula (1a) or (1c) are derivatives of cholestanol, cholesterol, or cholic acid. The group of $R^1$ may contain a functional group such as hydroxyl, alkoxyl, acyl or carbonyl.

Examples of the sulfonic acids represented by formula (1a) or (1c) include, but are not limited to, the following wherein Ac denotes acetyl.

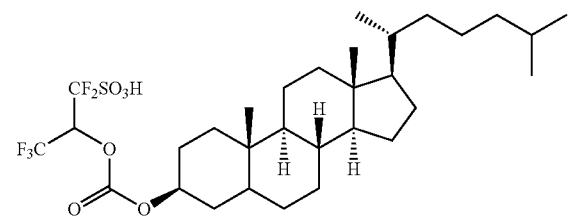

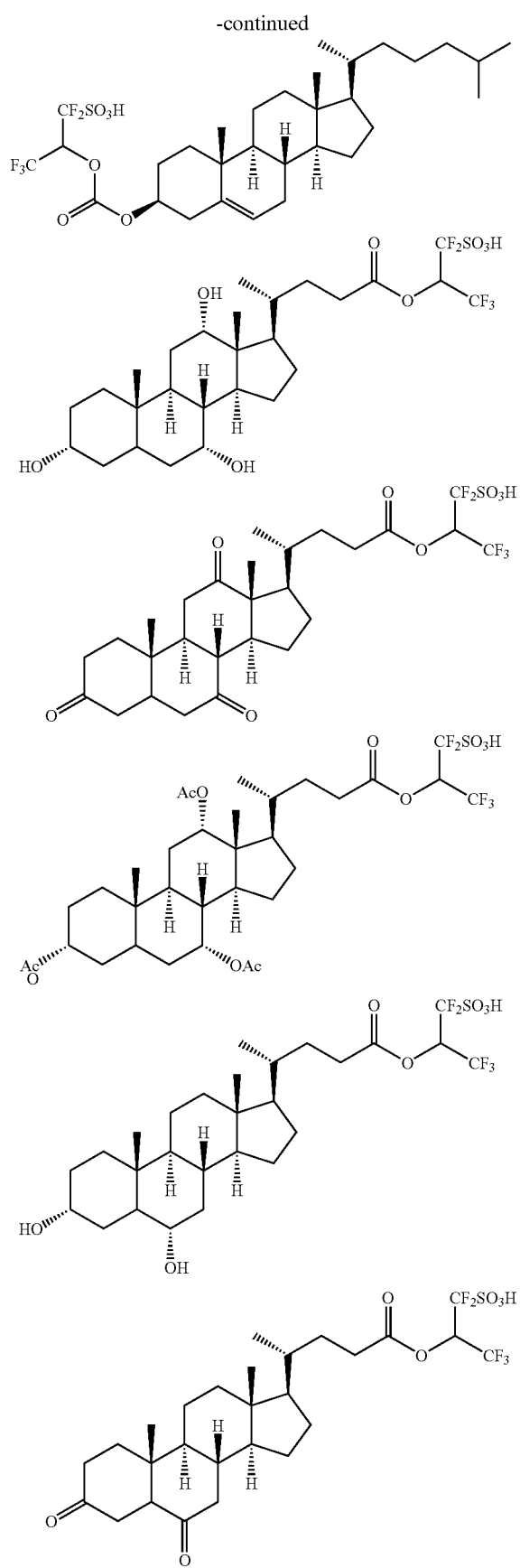
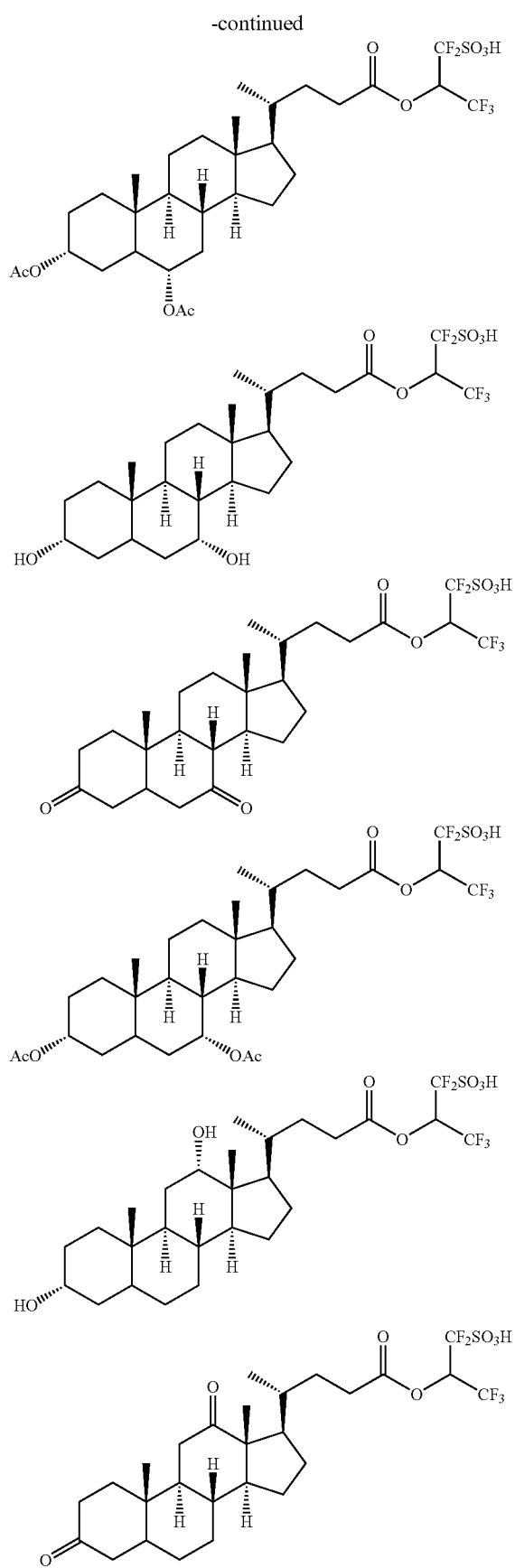

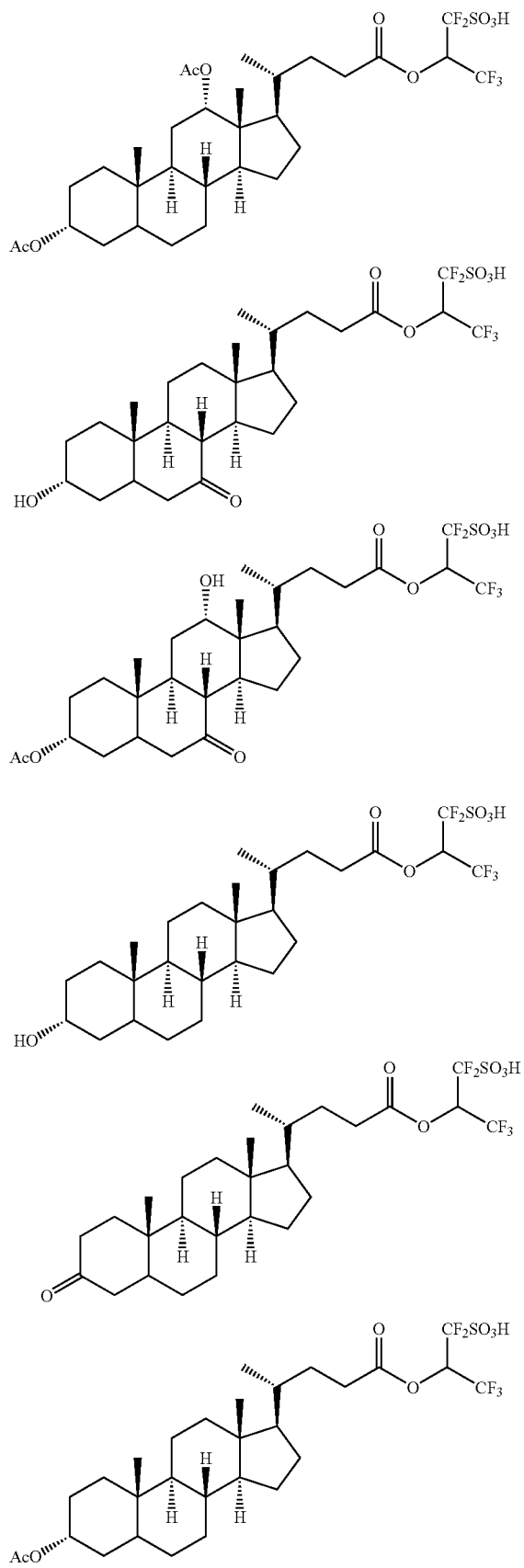
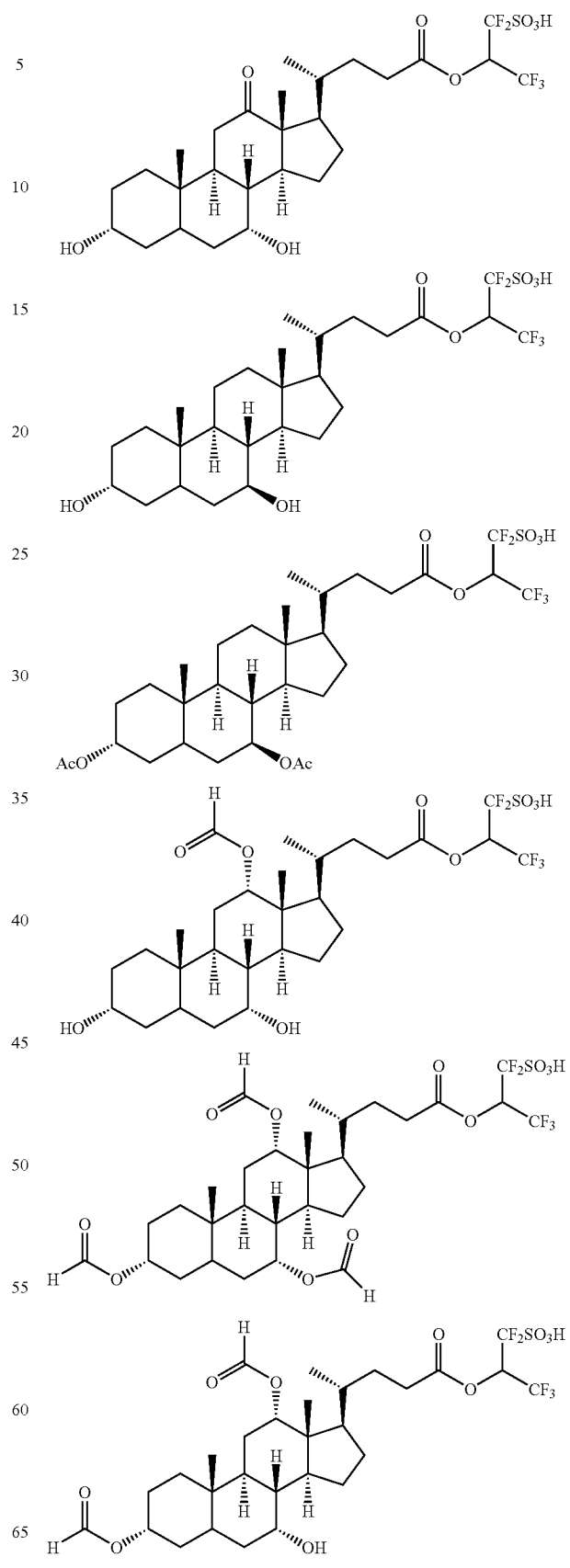

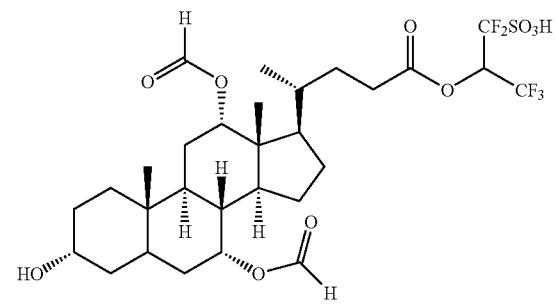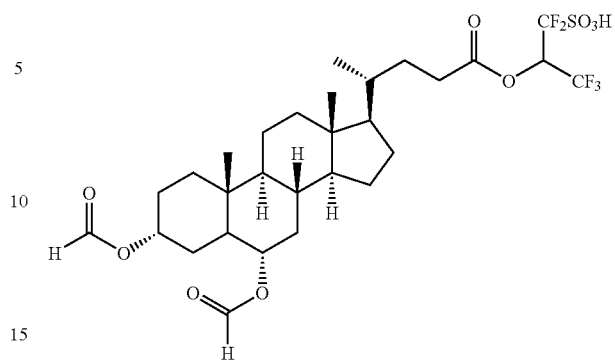

-continued
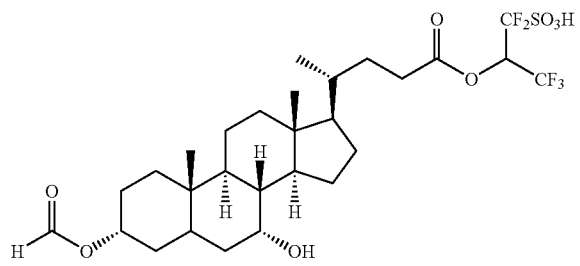
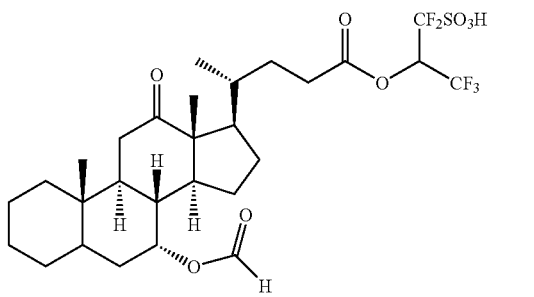

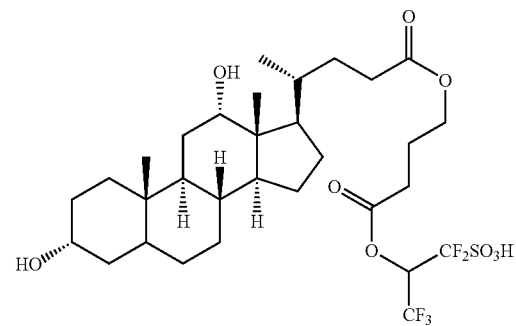
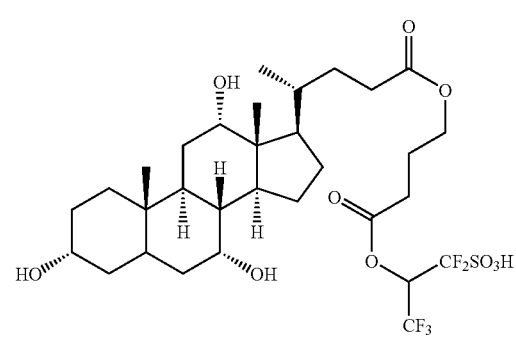
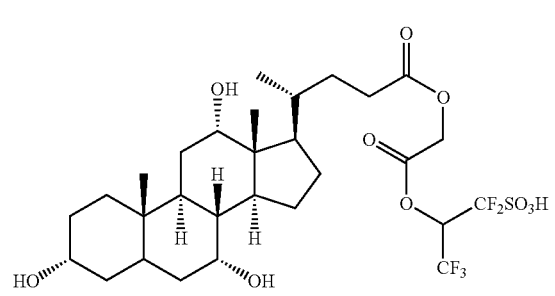
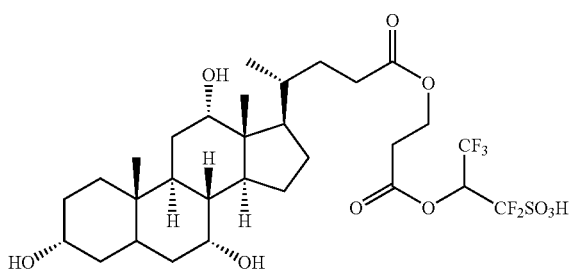
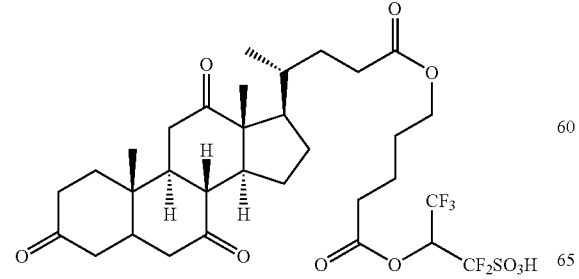
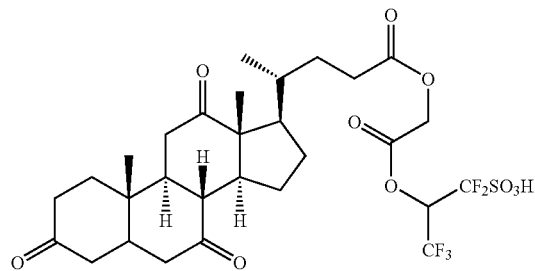
Of $R^1$, those groups of the formula (1d'), (1e') or (1f') shown below are preferred. In the structural formula, a bonding site is depicted by a broken line.
(1d')
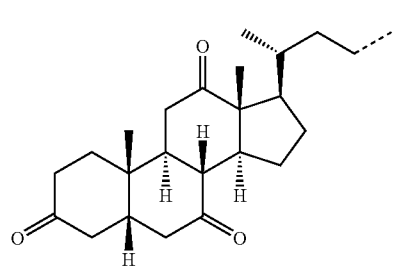
(1e')
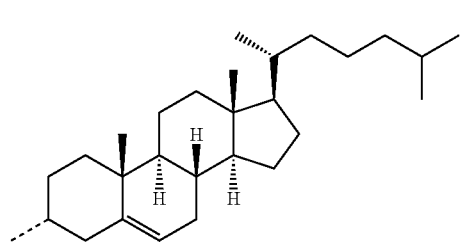

-continued (1f')

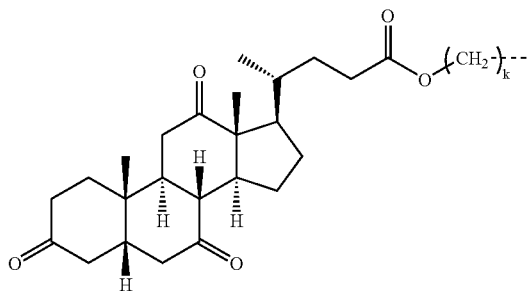

Note that k is an integer of 1 to 5.

Sulfonium Salt

The sulfonium salt of the invention has the general formula (2a) or (2c):

$$R^1\text{—COOCH}(CF_3)CF_2SO_3^{-R2}R^3R^4S^+ \quad (2a)$$

$$R^1\text{—O—COOCH}(CF_3)CF_2SO_3^{-}R^2R^3R^4S^+ \quad (2c)$$

wherein $R^1$ is a $C_{20}$-$C_{50}$ hydrocarbon group having a steroid structure, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom.

In formula (2a) or (2c), $R^1$ is as defined above. $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{10}$ aryl, aralkyl or aryloxoalkyl group, or any two or more of $R^2$, $R^3$ and $R^4$ may bond together to form a ring with the sulfur atom (in the formula). Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl, and thienyl; 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When two or more of $R^2$, $R^3$ and $R^4$ bond together to form a cyclic structure with the sulfur atom, divalent organic groups such as 1,4-butylene and 3-oxa-1,5-pentylene are exemplary of the cyclic structure-forming group. Also exemplified as the substituents of $R^2$, $R^3$ and $R^4$ are aryl groups having polymerizable substituent radicals such as acryloyloxy and methacryloyloxy radicals, and examples of such aryl groups are 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl groups.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and 4-tert-butoxycarbonylmethyloxyphenyldiphenylsulfonium. Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, (4-acryloyloxy-3,5-dimethylphenyl)diphenylsulfonium, and the like. For these polymerizable sulfonium cations, reference may be made to JP-A 4-230645 and JP-A 2005-84365. These polymerizable sulfonium salts may be used as a monomer in forming a polymer to be described later.

Another embodiment is a sulfonium salt having the general formula (3a) or (3c):

$$R^1\text{—COOCH}(CF_3)CF_2SO_3^{-}(R^5(O)_n)_m\text{Ph'S}^+\text{Ph}_2 \quad (3a)$$

$$R^1\text{—O—COOCH}(CF_3)CF_2SO_3^{-}(R^5(O)_n)_m\text{Ph'S}^+\text{Ph}_2 \quad (3c)$$

wherein $R^1$ is a $C_{20}$-$C_{50}$ hydrocarbon group having a steroid structure, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 (zero) or 1, Ph denotes phenyl, and Ph' denotes a phenyl group in which a number "m" of hydrogen atoms are substituted by $R^5(O)_n$— groups.

In formula (3a) or (3c), $R^1$ is as defined above. The substitution position of $R^5$—$(O)_n$—— group is not particularly limited, but is preferably 4- or 3-position on the phenyl group, and more preferably 4-position. Examples of groups represented by $R^5$ include methyl, ethyl, n-propyl, sec-propyl, cyclopropyl, n-butyl, sec-butyl, isobutyl, tert-butyl, n-pentyl, cyclopentyl, n-hexyl, cyclohexyl, n-octyl, n-decyl, n-dodecyl, trifluoromethyl, phenyl, 4-methoxyphenyl, and 4-tert-butylphenyl. In the case of n=1, acryloyl, methacryloyl, vinyl, and allyl are exemplary of $R^5$. The letter m is an integer of 1 to 5, and preferably 1, and n is 0 (zero) or 1.

Illustrative examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, (4-n-hexyloxy-3,5-dimethylphenyl)diphenylsulfonium, (4-methacryloyloxy-3,5-dimethylphenyl)diphenylsulfonium, and (4-acryloyloxy-3,5-dimethylphenyl)diphenylsulfonium.

Iodonium Salt

A further embodiment of the invention is a iodonium salt having the general formula (4a) or (4c):

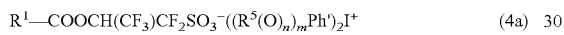

(4a)

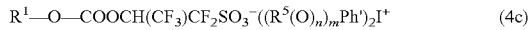

(4c)

wherein $R^1$ is a $C_{20}$-$C_{50}$ hydrocarbon group having a steroid structure; $R^5$ is a substituted or unsubstituted straight, branched or cyclic $C_1$-$C_{20}$ alkyl or alkenyl group, or a substituted or unsubstituted $C_6$-$C_{14}$ aryl group; m is an integer of 1 to 5, n is 0 (zero) or 1; and Ph' denotes a phenyl group in which a number "m" of hydrogen atoms are substituted by $R^5(O)_n$— groups.

In formula (4a) or (4c), $R^1$, $R^5$, n and m are as defined and illustrated above. The substitution position of $R^5$—$(O)_n$— group is not particularly limited, but is preferably 4- or 3-position on the phenyl group, and more preferably 4-position.

Illustrative examples of the iodonium cation include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with the bis(4-tert-butylphenyl)iodonium being preferred.

N-sulfonyloxyimide

A further embodiment of the invention is a N-sulfonyloxyimide compound having the general formula (5a) or (5c):

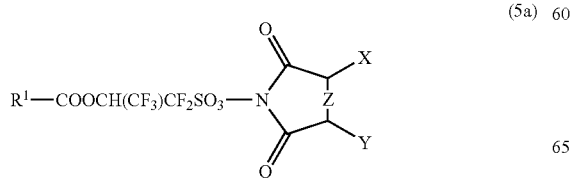

(5a)

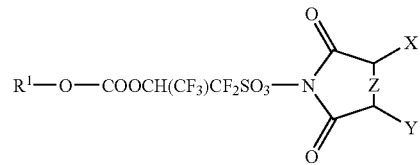

(5c)

wherein $R^1$ is a $C_{20}$-$C_{50}$ hydrocarbon group having a steroid structure, X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom.

In formula (5a) or (5c), $R^1$ is as defined above, X and Y are each independently hydrogen or a substituted or unsubstituted $C_1$-$C_6$ alkyl group, or X and Y may bond together to form a saturated or unsaturated, non-aromatic or aromatic $C_6$-$C_{12}$ ring with the carbon atoms to which they are attached, and Z is a single bond, double bond, methylene group or oxygen atom. Illustrative examples of the imide skeleton excluding the sulfonate moiety are given below. For the imide skeleton, reference may be made to JP-A 2003-252855.

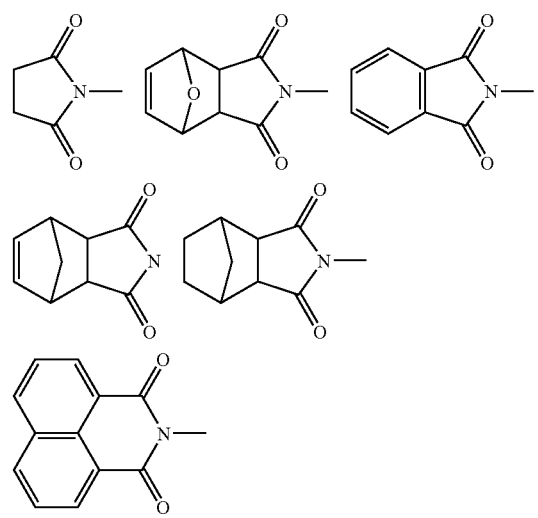

Oxime Sulfonate

A further embodiment of the invention is an oxime sulfonate compound having the general formula (6a) or (6c):

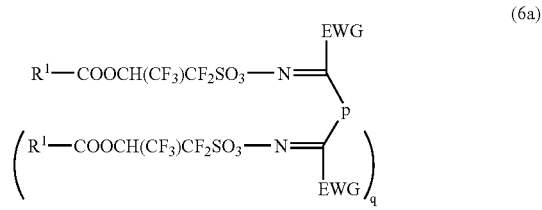

(6a)

-continued

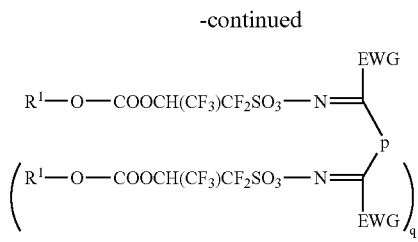

wherein $R^1$ is a $C_{20}$-$C_{50}$ hydrocarbon group having a steroid structure; q is 0 (zero) or 1; when q is 0, p is a substituted or unsubstituted $C_1$-$C_{20}$ alkyl group or a substituted or unsubstituted $C_6$-$C_{15}$ aryl group; when q is 1, p is a single bond, a substituted or unsubstituted $C_1$-$C_{20}$ alkylene group or a substituted or unsubstituted $C_6$-$C_{15}$ arylene group; EWG is a cyano, trifluoromethyl, perfluoroethyl, perfluoropropyl, 5H-perfluoropentyl, 6H-perfluorohexyl, nitro or methyl group.

In formula (6a) or (6c), $R^1$ is as defined above. When q is equal to 0, p is a substituted or unsubstituted $C_1$-$C_{20}$ alkyl group or a substituted or unsubstituted $C_6$-$C_{15}$ aryl group. When q is equal to 1, p is a single bond, a substituted or unsubstituted $C_1$-$C_{20}$ alkylene group or a substituted or unsubstituted $C_6$-$C_{15}$ arylene group. EWG is a cyano, trifluoromethyl, perfluoroethyl, perfluoropropyl, 5H-perfluoropentyl, 6H-perfluorohexyl, nitro or methyl group. When q is equal to 1, two EWG's may bond together to form a ring of 6 carbon atoms with the carbon atoms to which they are attached. The skeletons of the oxime sulfonates are described in U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004/074242.

Exemplary skeletons of oxime sulfonates excluding the sulfonate moiety are given below.

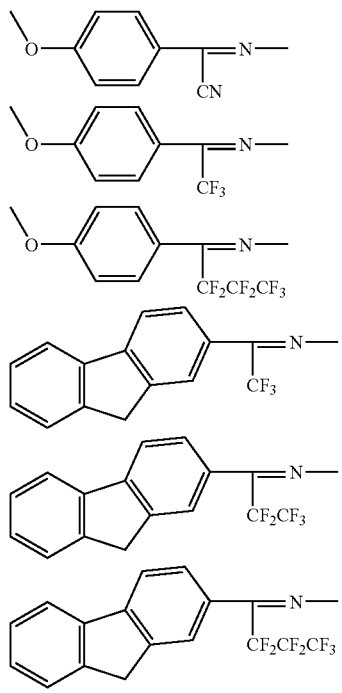

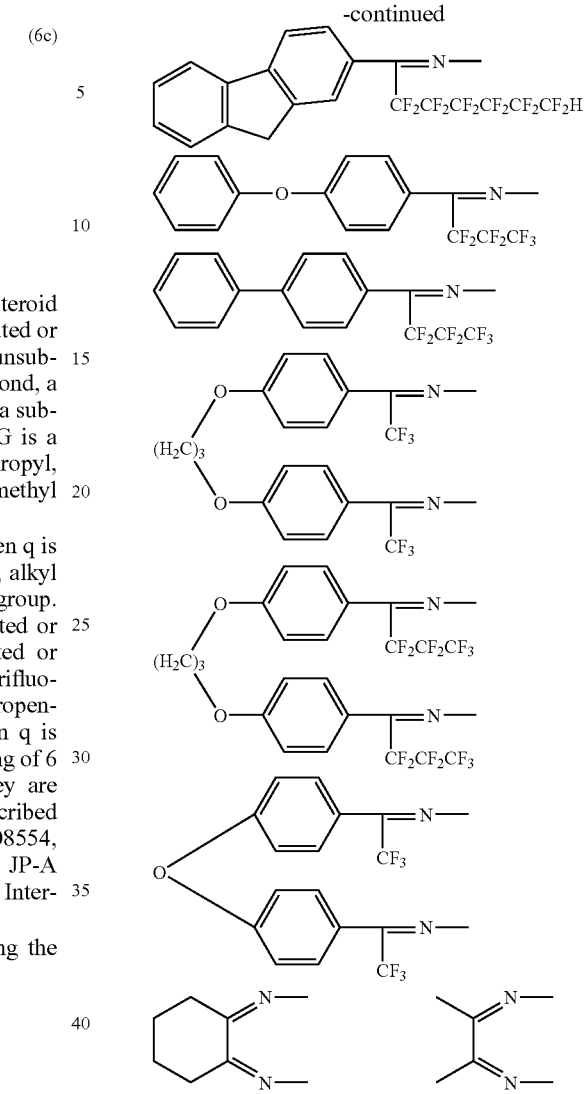

Described below is how to synthesize the sulfonium salts of formula (2a) or (2c) as typical examples of the foregoing photoacid generators capable of generating a sulfonic acid of formula (1a) or (1c).

A sulfonium salt having carboxylate and steroid structures as represented by formula (2a) may be synthesized by starting with triphenylsulfonium 1,1,3,3,3-pentafluoro-2-hydroxypropanesulfonate, synthesized as will be described later, and reacting it with an aliphatic carboxylic acid halide having a steroid structure under basic conditions.

Similarly, a sulfonium salt having carbonate and steroid structures as represented by formula (2c) may be synthesized by starting with triphenylsulfonium 1,1,3,3,3-pentafluoro-2-hydroxypropanesulfonate, synthesized as will be described later, and reacting it with a halo-formic acid ester having a steroid structure under basic conditions.

The sulfonium salts of formula (3a) or (3c) and the iodonium salts of formula (4a) or (4c) can be synthesized by the same method as described above.

The synthesis of the imide sulfonate of formula (5a) or (5c) or oxime sulfonate of formula (6a) or (6c) starts with an imide sulfonate or oxime sulfonate having a 1,1,3,3,3-pentafluoro-2-hydroxypropanesulfonate moiety and an aliphatic carboxylic acid halide having a steroid structure. By reacting them under basic conditions, an imide sulfonate or oxime sulfonate having carboxylate ester and steroid structures can be prepared.

Briefly noted herein is the synthesis of triphenylsulfonium 1,1,3,3,3-pentafluoro-2-hydroxypropane-sulfonate. First, an aliphatic or aromatic carboxylic acid ester of 1,1,3,3,3-pentafluoropropen-2-yl, typically 1,1,3,3,3-pentafluoropropen-2-yl benzoate, which was developed by Nakai et al. using 1,1,1,3,3,3-hexafluoro-2-propanol as the starting reactant, is reacted with sodium hydrogen sulfite or sodium sulfite in a solvent such as water or alcohol or a mixture thereof, forming a corresponding 1,1,3,3,3-pentafluoro-2-acyloxypropane-sulfonic acid salt or 1,1,3,3,3-pentafluoro-2-arenecarbonyloxypropanesulfonic acid salt. This salt is ion-exchanged with a suitable sulfonium salt, forming triphenylsulfonium 1,1,3,3,3-pentafluoro-2-acyloxypropanesulfonate or triphenylsulfonium 1,1,3,3,3-pentafluoro-2-arenecarbonyloxypropanesulfonate. The carboxylate moiety of the sulfonate is then subjected to hydrolysis with the aid of an alkali such as sodium hydroxide or potassium hydroxide, or solvolysis with the aid of an alcohol and base, yielding the target compound, triphenylsulfonium 1,1,3,3,3-pentafluoro-2-hydroxypropane-sulfonate.

Salts of sulfonium other than triphenylsulfonium and iodonium may be similarly synthesized.

The synthesis of an imide sulfonate or oxime sulfonate having a 1,1,3,3,3-pentafluoro-2-hydroxypropanesulfonate moiety is as follows. First, 1,1,3,3,3-pentafluoro-2-acyloxypropanesulfonate salt or 1,1,3,3,3-pentafluoro-2-arenecarbonyloxypropanesulfonate salt is reacted with a chlorinating agent such as thionyl chloride, phosphorus oxychloride or phosphorus pentachloride to form a corresponding sulfonyl chloride or sulfonic acid anhydride. This is further reacted with N-hydroxydicarboxylimide or oxime in a conventional way, forming 1,1,3,3,3-pentafluoro-2-acyloxypropane-sulfonate or 1,1,3,3,3-pentafluoro-2-arenecarbonyloxypropanesulfonate. This is followed by hydrolysis of the acyloxy or arenecarbonyloxy group, forming the desired intermediate, imide sulfonate or oxime sulfonate having a 1,1,3,3,3-pentafluoro-2-hydroxypropanesulfonate moiety.

The starting sulfonium and iodonium salts can be synthesized in accordance with the teachings of The Chemistry of Sulfonium Group Part 1, John-Wiley & Sons (1981), Advanced Photochemistry, Vol. 17, John-Wiley & Sons (1992), J. Org. Chem., 53, 5571-5573, 1958, JP-A 8-311018, JP-A 9-15848, JP-A 2001-122850, JP-A 7-25846, JP-A 2001-181221, JP-A 2002-193887, and JP-A 2002-193925. The onium cation having an acryloyloxy or methacryloyloxy group as the polymerizable substituent group can be synthesized by reacting (currently available) hydroxyphenyldiphenylsulfonium halide with acryloyl chloride or methacryloyl chloride under basic conditions according to the methods described in JP-A 4-230645 and JP-A 2005-84365.

For the synthesis of imide sulfonate or oxime sulfonate, reference should be made to the above-cited JP-A 2003-252855, U.S. Pat. No. 6,261,738, JP-A 9-95479, JP-A 9-208554, JP-A 9-230588, Japanese Patent No. 2,906,999, JP-A 9-301948, JP-A 2000-314956, JP-A 2001-233842, and International Publication 2004-074242.

As described above, a first embodiment of the present invention provides a photoacid generator for chemically amplified resist compositions which generates a sulfonic acid having formula (1a) or (1c) upon exposure to high-energy radiation. A second embodiment of the present invention provides a sulfonium salt, iodonium salt, dicarboxylimide sulfonate, and oxime sulfonate serving as photoacid generators in chemically amplified resist compositions. A third embodiment of the present invention provides a resist composition comprising a photoacid generator which generates a sulfonic acid having formula (1a) or (1c) upon exposure to high-energy radiation and a resin which changes its solubility in an alkaline developer liquid under the action of acid.

Resist Composition

The resist composition of the invention is typically embodied as (i) a chemically amplified positive resist composition comprising
    (A) a photoacid generator capable of generating a sulfonic acid having formula (1a) or (1c),
    (B) an organic solvent,
    (C) a base resin which changes its solubility in an alkaline developer liquid under the action of acid, and
    one or more optional components including (D) a quencher, (E) a photoacid generator other than (A), (F) an organic acid derivative and/or fluorinated alcohol, and (G) a dissolution inhibitor having a weight average molecular weight of up to 3,000, and further optionally, (H) a surfactant which is insoluble or substantially insoluble in water and soluble in alkaline developer and/or a surfactant which is insoluble or substantially insoluble in water and alkaline developer; and (ii) a chemically amplified negative resist composition comprising
    (A) a photoacid generator capable of generating a sulfonic acid having formula (1a) or (1c),
    (B) an organic solvent,
    (C') a base resin which is normally alkali soluble, but becomes substantially alkali insoluble under the action of a crosslinker,
    (I) a crosslinker which induces crosslinkage under the action of acid, and
    one or more optional components including (D) a quencher and (E) a photoacid generator other than (A), and further optionally, (H) a surfactant which is insoluble or substantially insoluble in water and soluble in alkaline developer and/or a surfactant which is insoluble or substantially insoluble in water and alkaline developer.

The PAG which generates a sulfonic acid having formula (1a) or (1c) as component (A) is as described above. More specifically, it is a compound having formula (2a), (2c), (3a), (3c), (4a), (4c), (5a), (5c), (6a) or (6c). In the resist composition, the PAG is specifically compounded in an amount of 0.1 to 10 parts, more specifically 1 to 7 parts by weight per 100 parts by weight of the base resin. Note that parts by weight per 100 parts by weight of the resin is often abbreviated as "phr".

Component B

The organic solvent used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone.

These solvents may be used alone or in combinations of two or more thereof. Of the above organic solvents, it is recommended to use diethylene glycol dimethyl ether, 1-ethoxy-2-propanol, PGMEA, cyclohexanone and mixtures thereof because the photoacid generator is most soluble therein.

An appropriate amount of the organic solvent used is about 200 to 3,000 parts, especially about 400 to 2,000 parts by weight per 100 parts by weight of the base resin.

Component C

The base resin used herein is one or more polymers selected from the group consisting of poly(meth)acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers. The base resin used herein may contain silicon atoms or fluorine atoms.

The base resins used as component (C) or (C') in the inventive compositions include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride and similar copolymers further containing vinyl ethers or (meth)acrylic acid esters, polynorbornene, ring-opening metathesis polymerized cycloolefins, and hydrogenated ring-opening metathesis polymerized cycloolefins, for ArF excimer laser resist use; and fluorinated forms of the foregoing polymers (for both KrF and ArF laser uses) for $F_2$ excimer laser resist use, although the base resins are not limited to these polymers. Understandably, the sulfonium salts and iodonium salts having polymerizable substituent groups according to the invention may be used as a monomer component in forming the base resin. Typical sulfonium and iodonium salts for such use are combinations of onium cations such as (4-acryloyloxyphenyl)diphenylsulfonium, (4-methacryloyloxyphenyl) diphenylsulfonium, (4-acryloyloxyphenyl)phenyliodonium, and (4-methacryloyloxyphenyl)phenyliodonium cations with anions such as 1-(difluorosulfomethyl)-2,2,2-trifluoroethyl hydrogen cyclohexanedicarboxylate. The base resins may be used alone or in admixture of two or more. In the case of positive resist compositions, it is a common practice to substitute acid labile groups for hydroxyl groups on phenols, carboxyl groups or fluorinated alkyl alcohols for reducing the rate of dissolution in unexposed regions.

The base resin (C) may comprise recurring units containing an acid labile group of the general formula (8) and recurring units of at least one type having the general formulae (9) to (11), shown below.

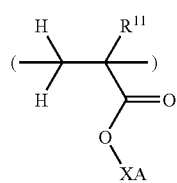
(8)

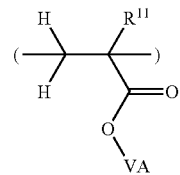
(9)

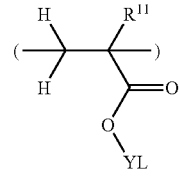
(10)

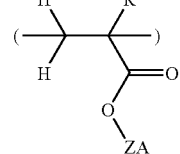
(11)

Herein, $R^{11}$ is a hydrogen atom, fluorine atom, methyl group or trifluoromethyl group, VA is a polar radical-containing substituent group of 1 to 20 carbon atoms, XA is an acid labile group, YL is a lactone structure-containing substituent group, and ZA is a hydrogen atom, fluoroalkyl group of 1 to 15 carbon atoms or fluoroalcohol-containing substituent group of 1 to 15 carbon atoms.

Under the action of an acid, a polymer comprising recurring units of formula (8) is decomposed to generate a carboxylic acid and turns into an alkali-soluble polymer. The acid labile groups represented by XA may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

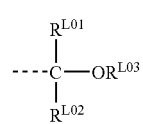
(L1)

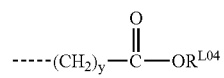
(L2)

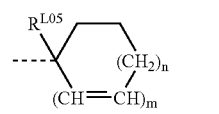
(L3)

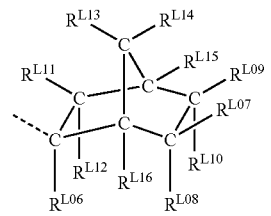
(L4)

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the straight, branched or cyclic alkyl groups are as exemplified above for $R^{L01}$ and $R^{L02}$, and examples of the substituted alkyl groups are shown below.

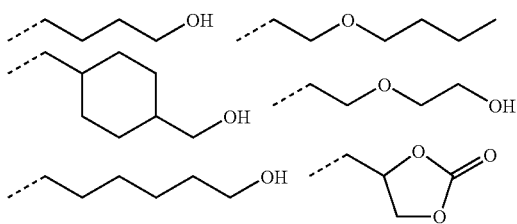

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached, and in this case, each group participating in ring formation is a straight or branched alkylene group of 1 to 18 carbon atoms, preferably 1 to 10 carbon atoms.

In formula (L2), $RL^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen s atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m is 0 or 1, n is 0, 1, 2 or 3, and 2m+n is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $RL^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). In this case, each group participating in ring formation is a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $RL^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

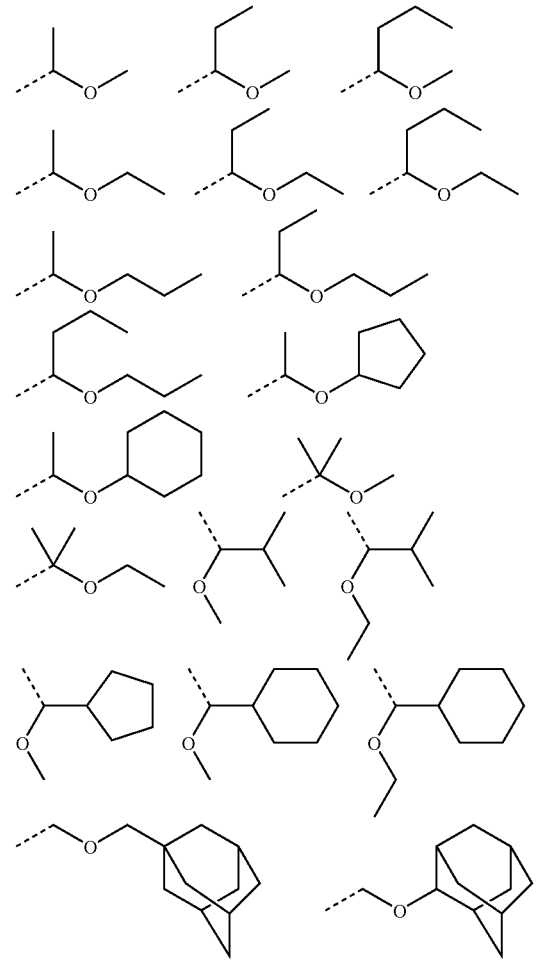

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are preferably groups of the following formulae (L4-1) to (L4-4).

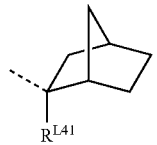
(L4-1)

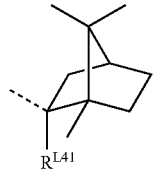
(L4-2)

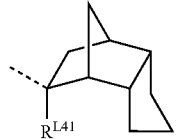
(L4-3)

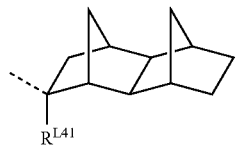
(L4-4)

In formulae (L4-1) to (L4-4), the broken line indicates a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

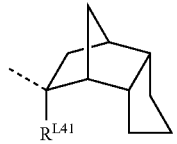
(L4-3-1)

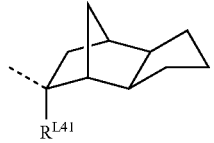
(L4-3-2)

Similarly, the general formula (L4-4) represents one or a mixture of two or more selected from groups having the following general formulas (L4-4-1) to (L4-4-4).

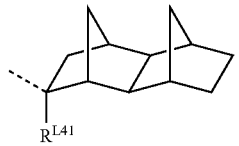
(L4-4-1)

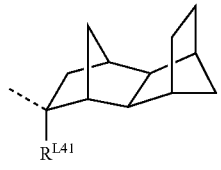
(L4-4-2)

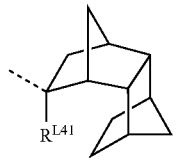
(L4-4-3)

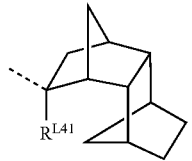
(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

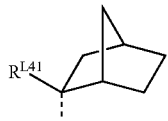 (L4-1-endo)
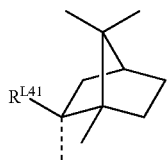 (L4-2-endo)
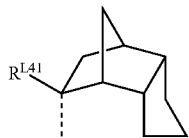 (L4-3-endo)
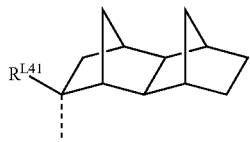 (L4-4-endo)
(See JP-A 2000-336121.)
Illustrative examples of the acid labile group of formula (L4) are given below.
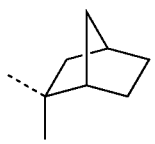
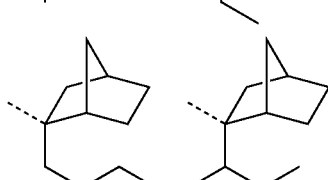
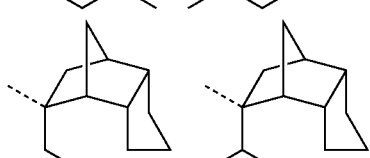
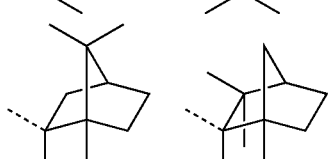
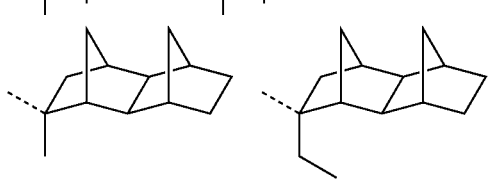
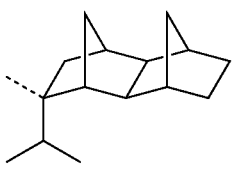
Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.
Illustrative, non-limiting examples of the recurring units of formula (8) are given below.
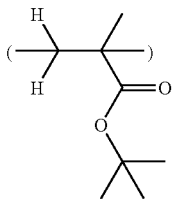 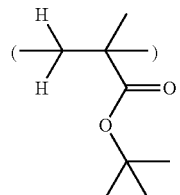
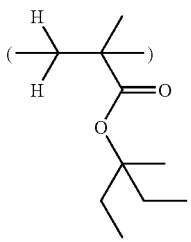 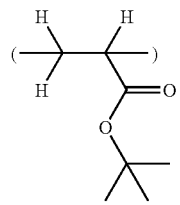
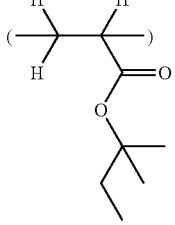 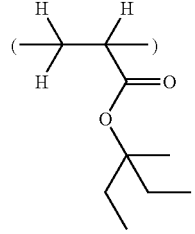
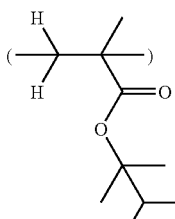 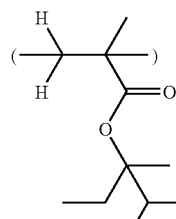
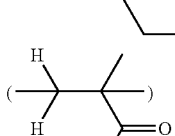 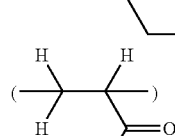
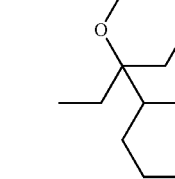 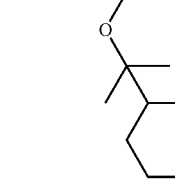

-continued
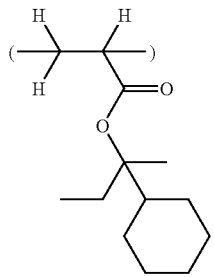 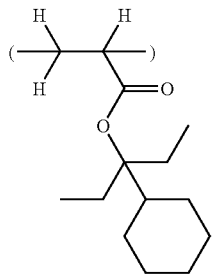
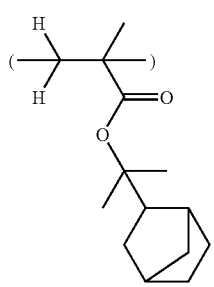 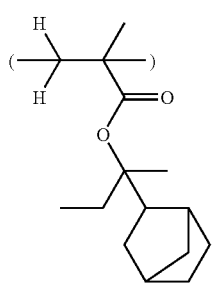
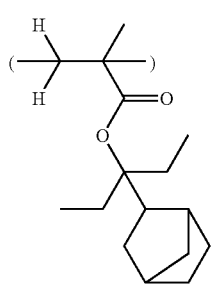 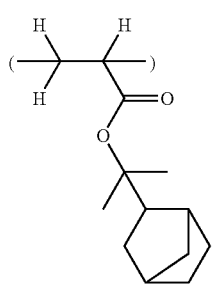
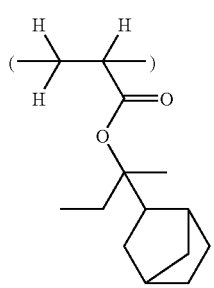 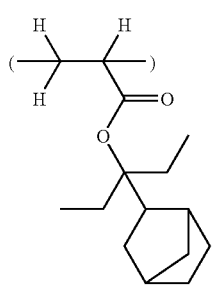
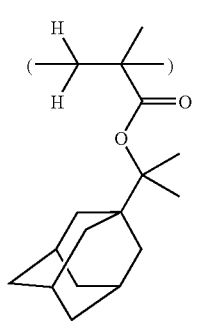 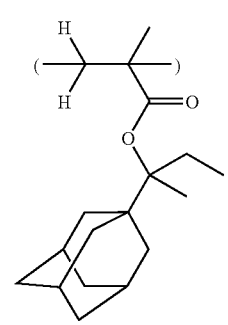
-continued
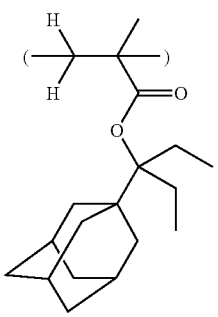 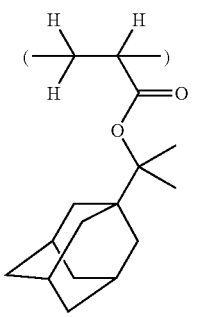
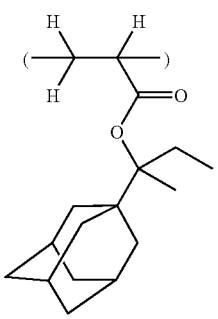 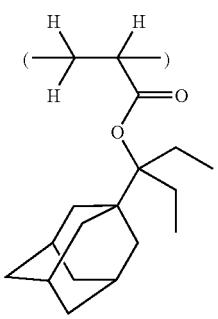
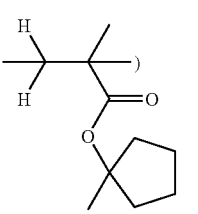 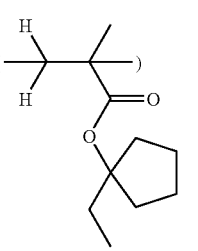
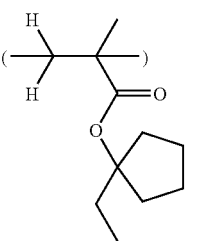 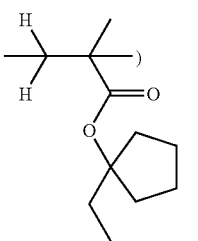
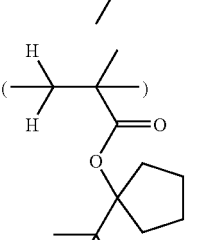 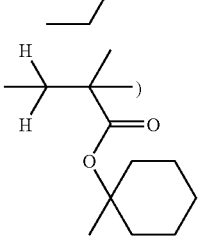
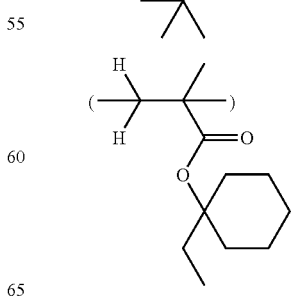 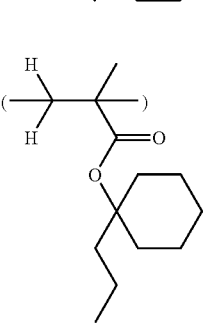

-continued
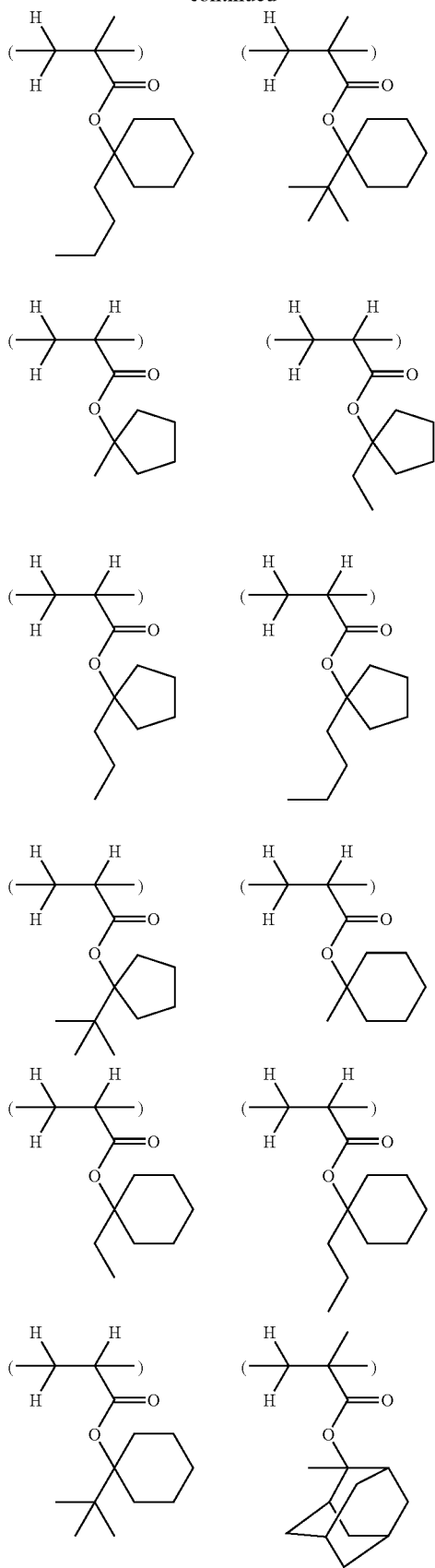
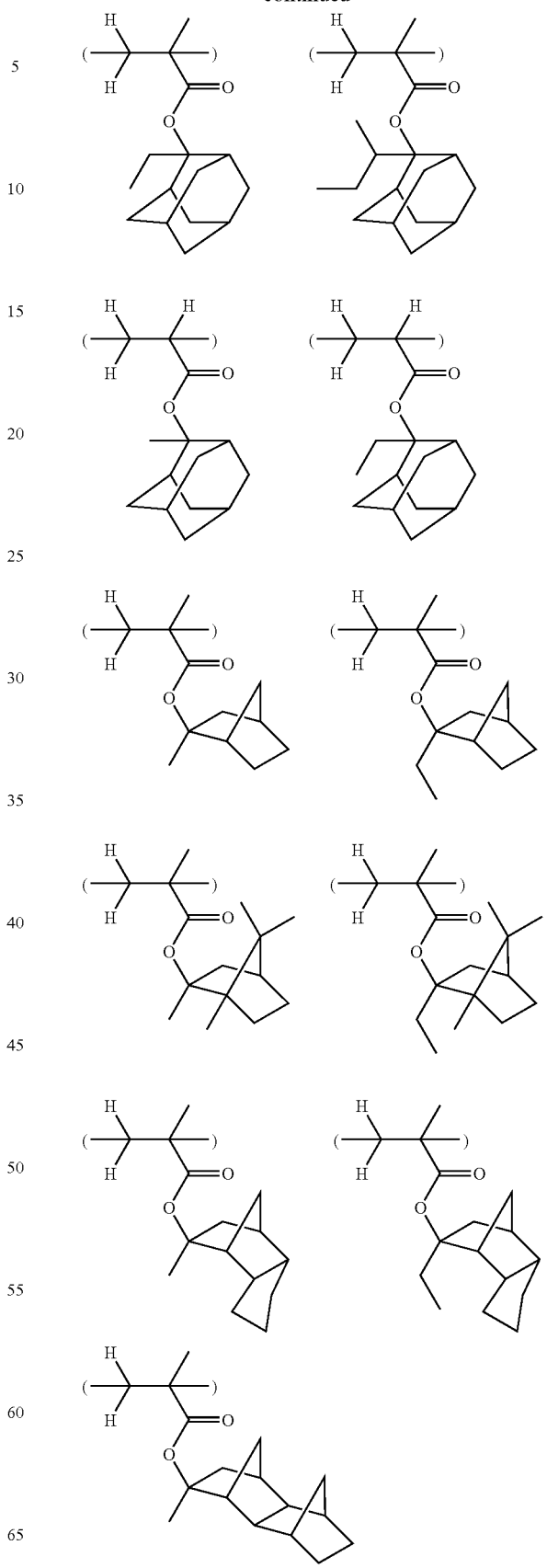

-continued
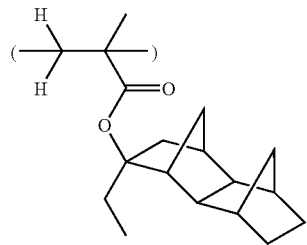
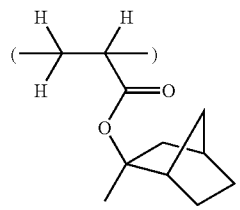
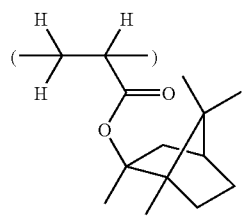
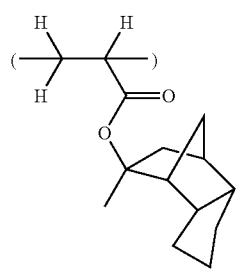
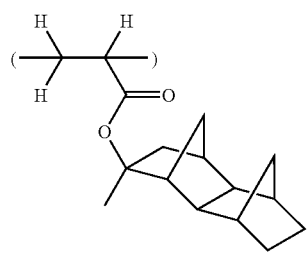
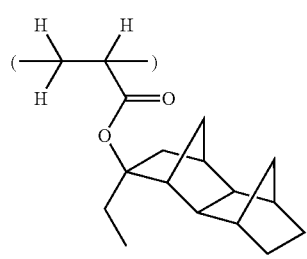
-continued
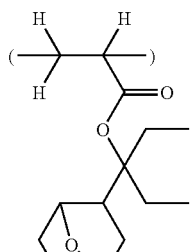
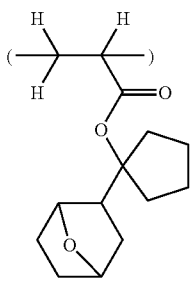
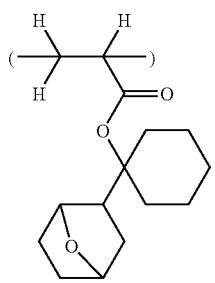
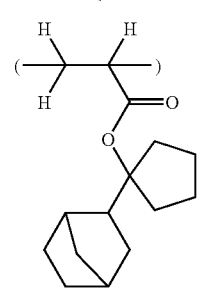
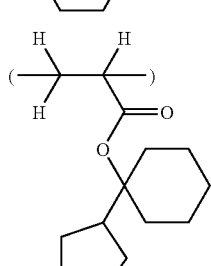
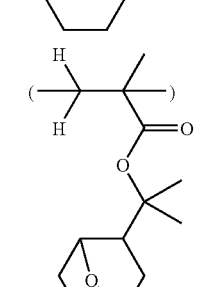
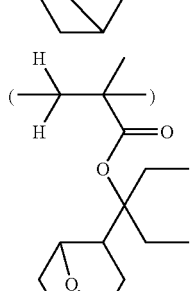

-continued

-continued
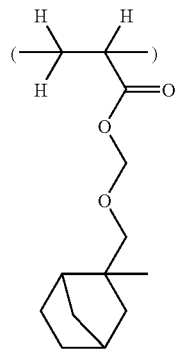
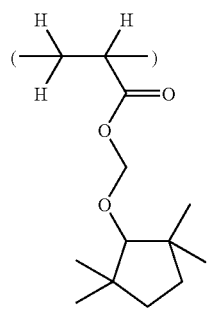
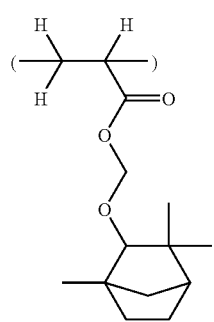
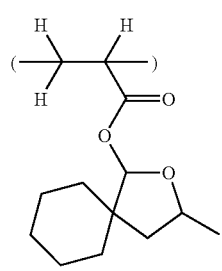
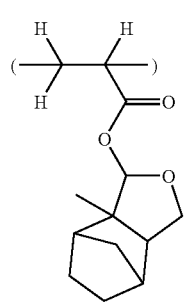
-continued
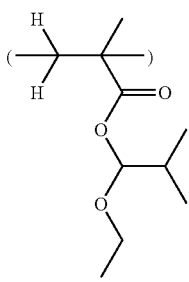
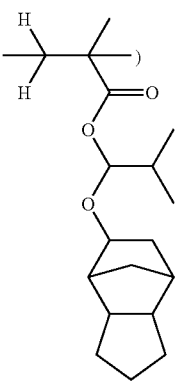
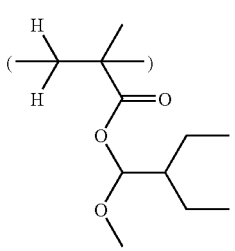
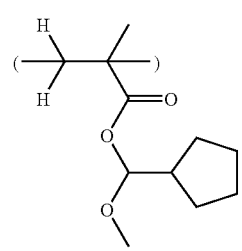
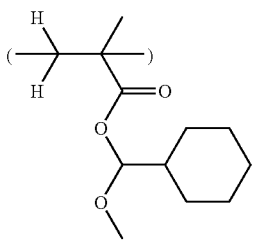
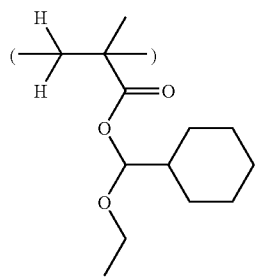
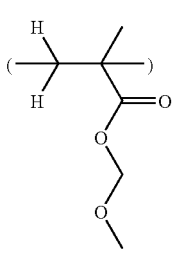
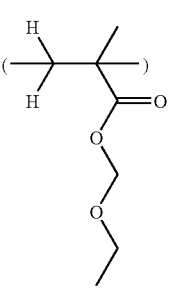
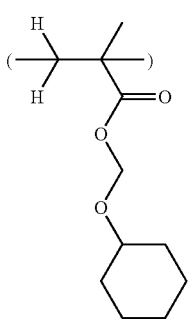
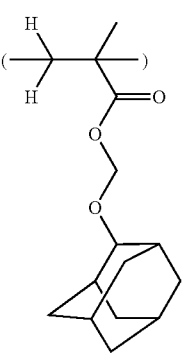

-continued
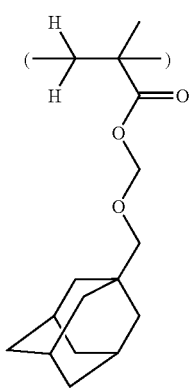 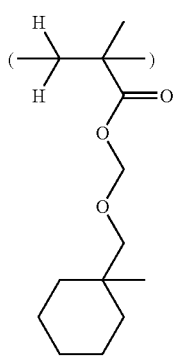 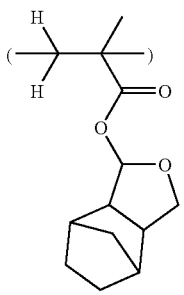 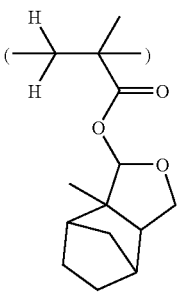
Illustrative, non-limiting examples of the recurring units of formula (9) are given below.
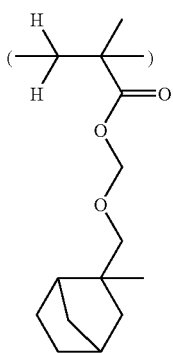 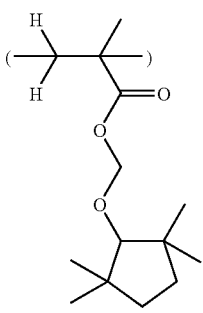 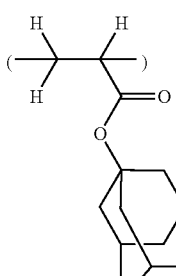 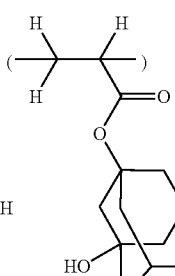
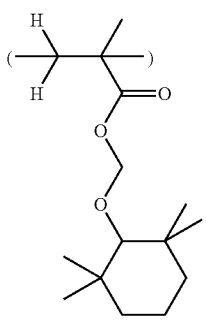 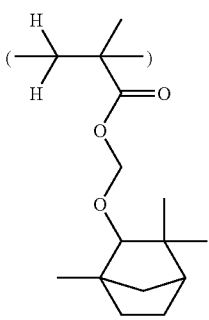 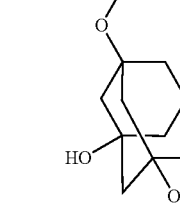 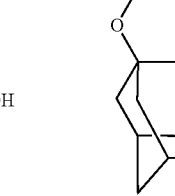
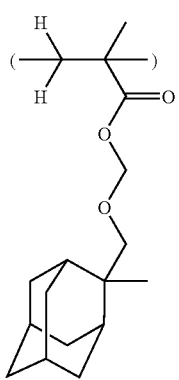 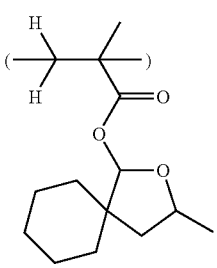 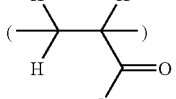 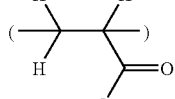
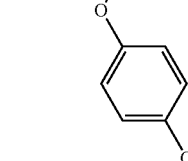 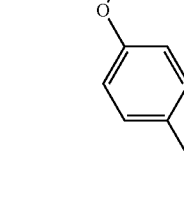

-continued
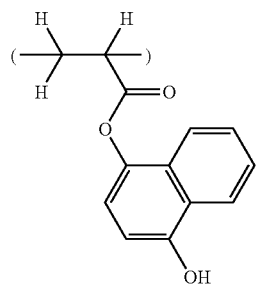
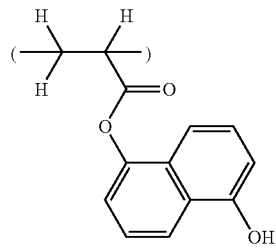
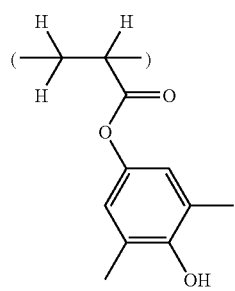
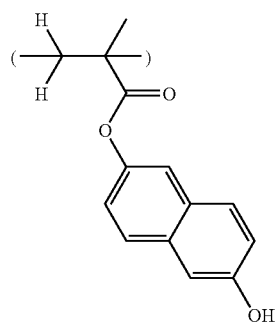
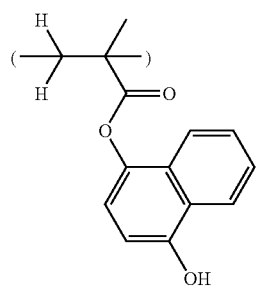
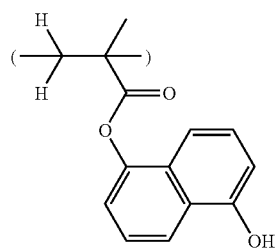
-continued
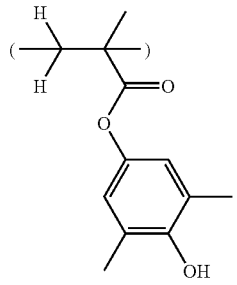
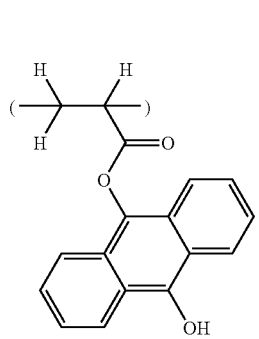
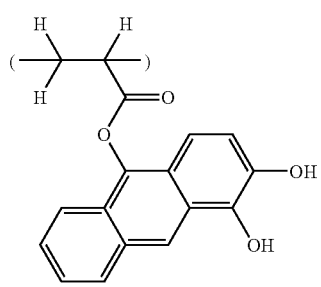
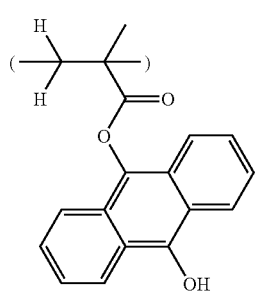
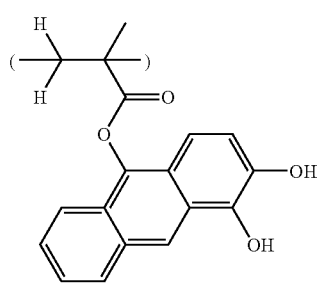

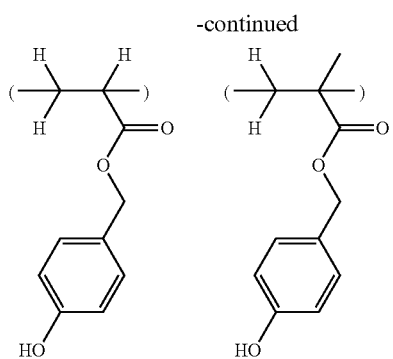
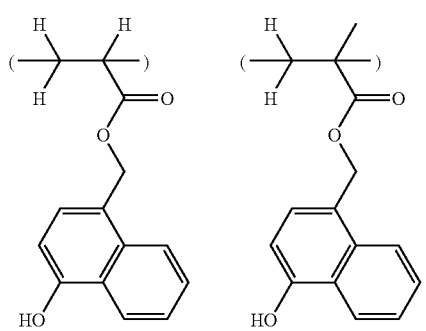
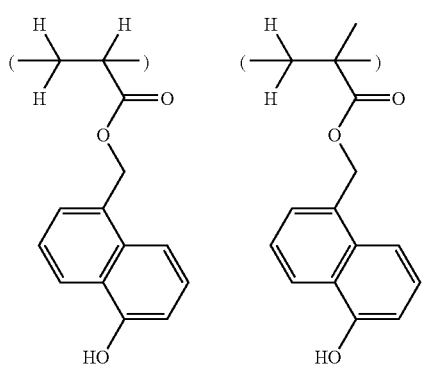

Illustrative, non-limiting examples of the recurring units of formula (10) are given below. In the following examples, recurring units having an acid labile group are included. While such recurring units having an acid labile group overlap those exemplified as the acid labile group of formula (L2), they may be utilized either as lactone units or as acid labile group-containing units.

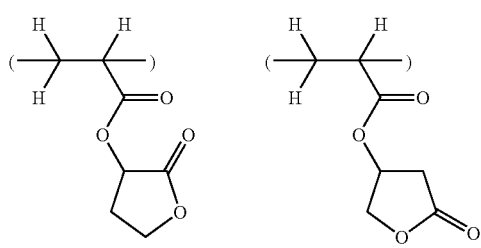
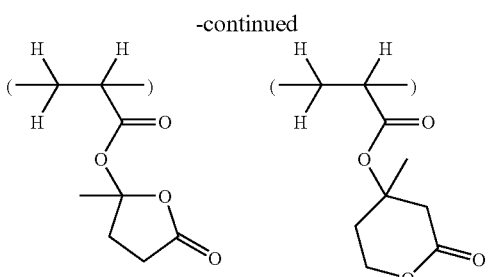
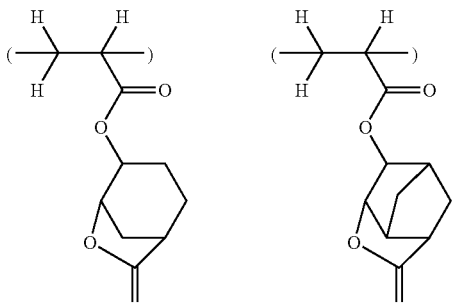
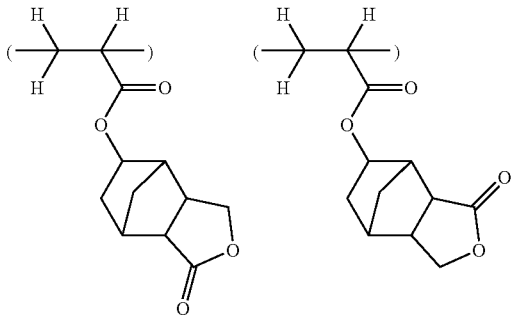
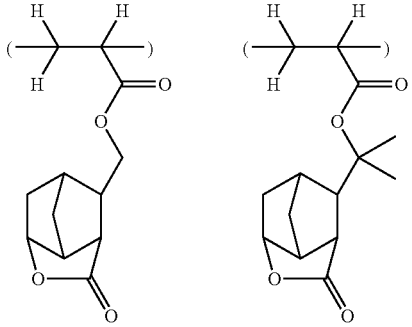
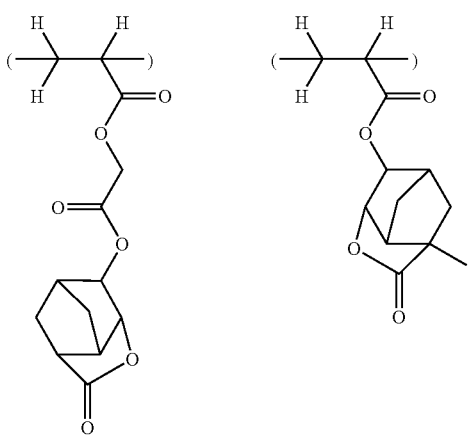

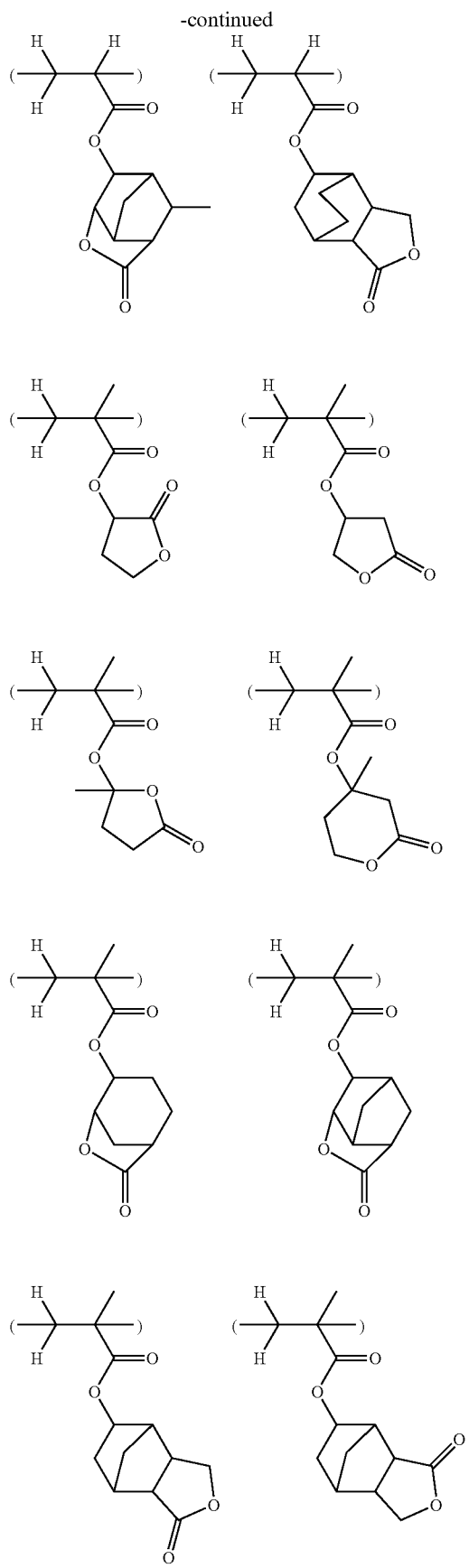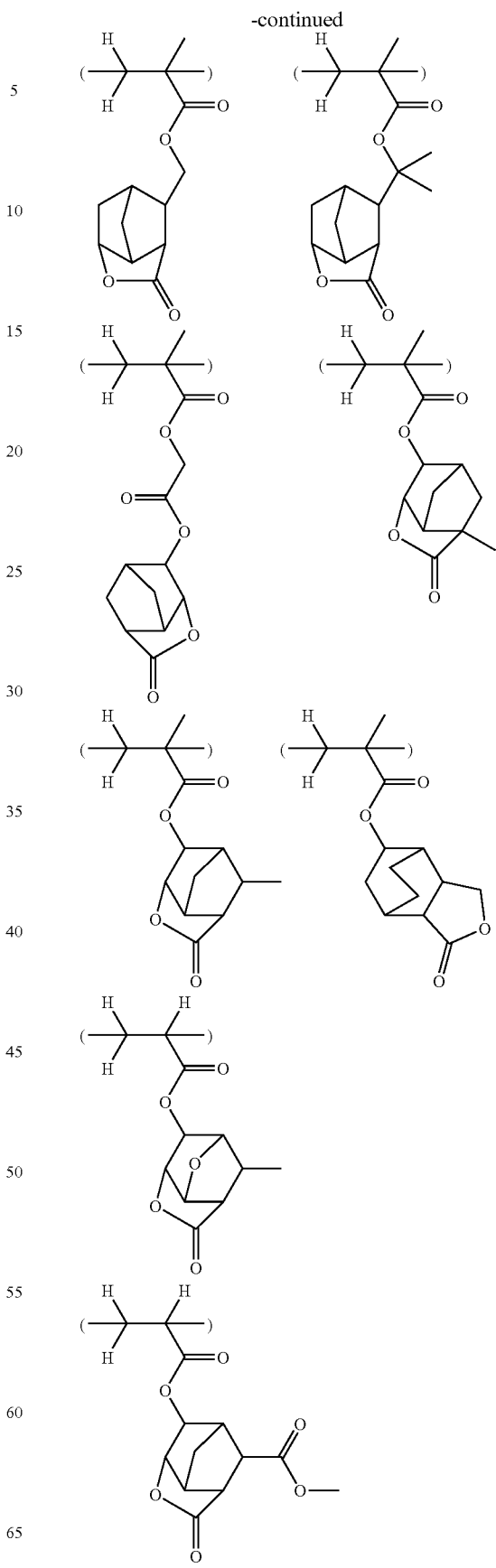

-continued
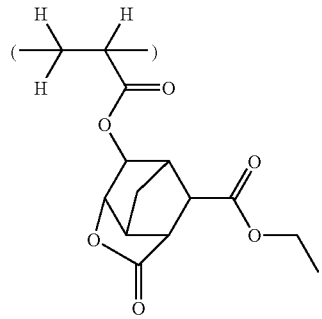
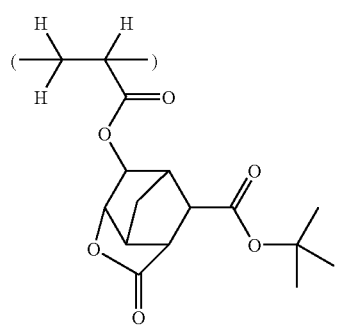
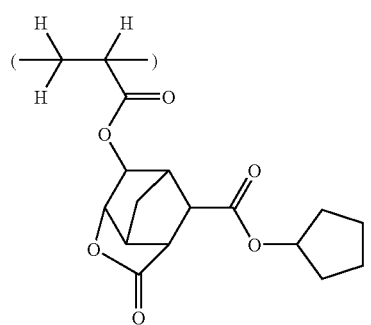
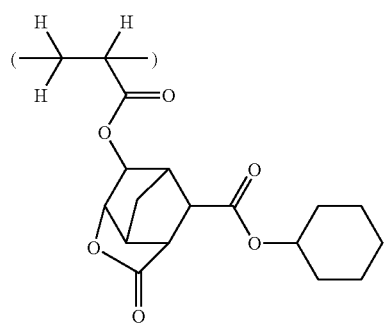
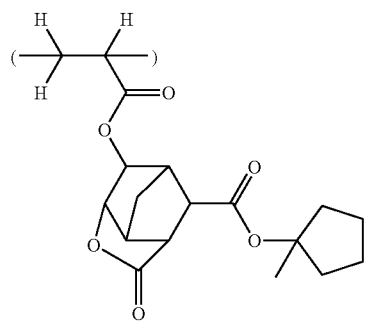
-continued
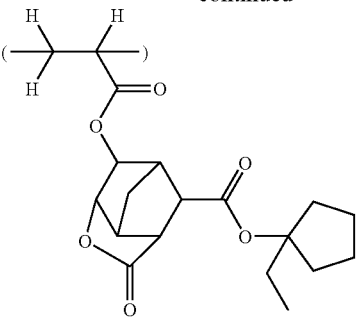
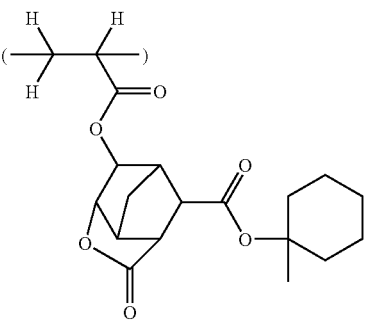
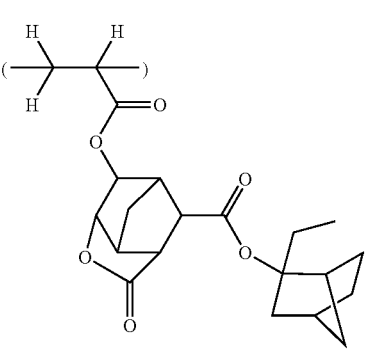
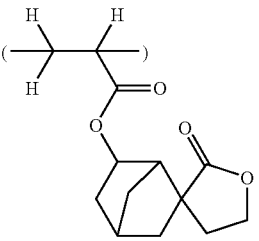
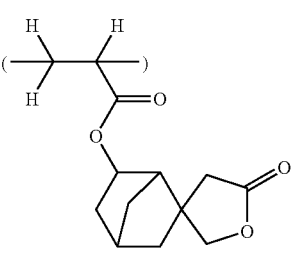

-continued
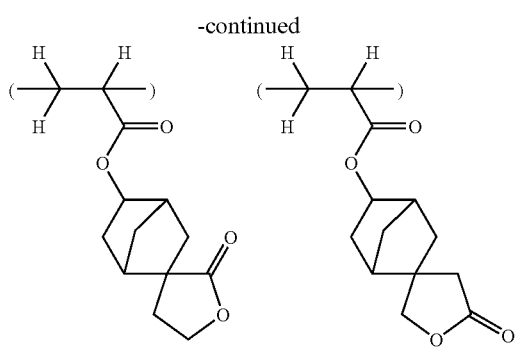
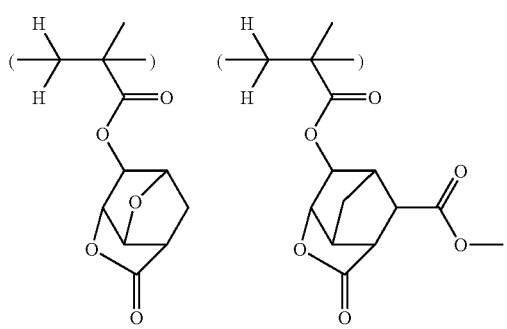
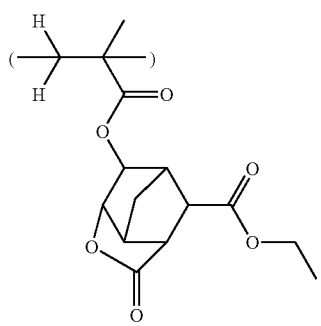
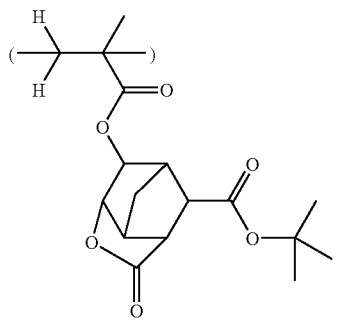
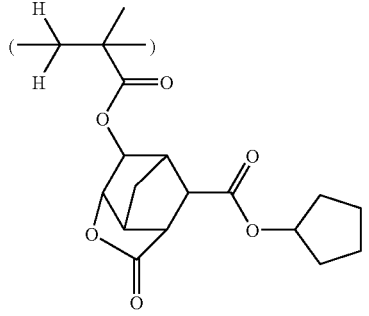
-continued
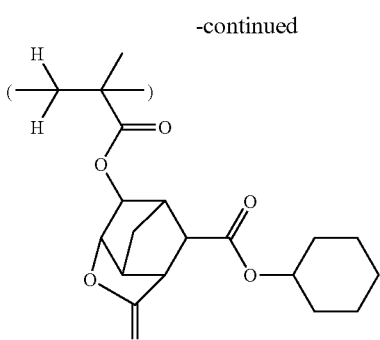
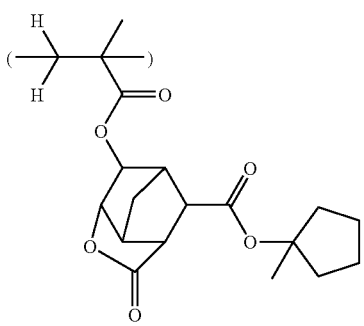
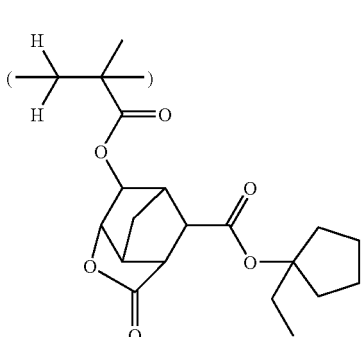

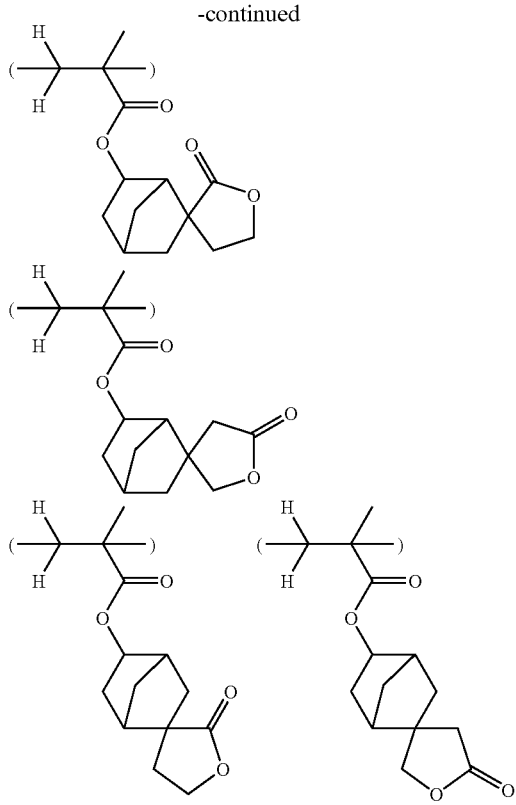

Also useful are recurring units of the following general formula (5L-1).

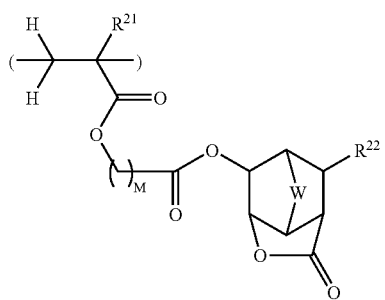

In formula (5L-1), $R^{21}$ is a hydrogen atom, fluorine atom, methyl group or trifluoromethyl group, with the methyl being preferred. $R^{22}$ is a hydrogen atom or $CO_2R^{23}$ wherein $R^{23}$ is hydrogen, halogen or a straight, branched or cyclic, monovalent hydrocarbon group of 1 to 15 carbon atoms, optionally containing an oxygen atom. W is $CH_2$, O or S. M is an integer of 1 to 3.

Illustrative examples of $R^{23}$ include hydrogen, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-methylcyclohexyl, 1-ethylcyclohexyl, 2-ethylhexyl, n-octyl, 2-methylbicyclo[2.2.1]heptan-2-yl, 2-ethylbicyclo[2.2.1]heptan-2-yl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, 4-methyltetracyclo[6.2.1.1$^{3,6}$.0$^{2,7}$]dodecan-4-yl, 4-ethyltetracyclo[6.2.1.1$^{3,6}$.0$^{2,7}$]dodecan-4-yl, methoxymethyl, ethoxymethyl, methoxyethyl, ethoxyethyl, methoxyethoxyethyl, and the groups shown below.

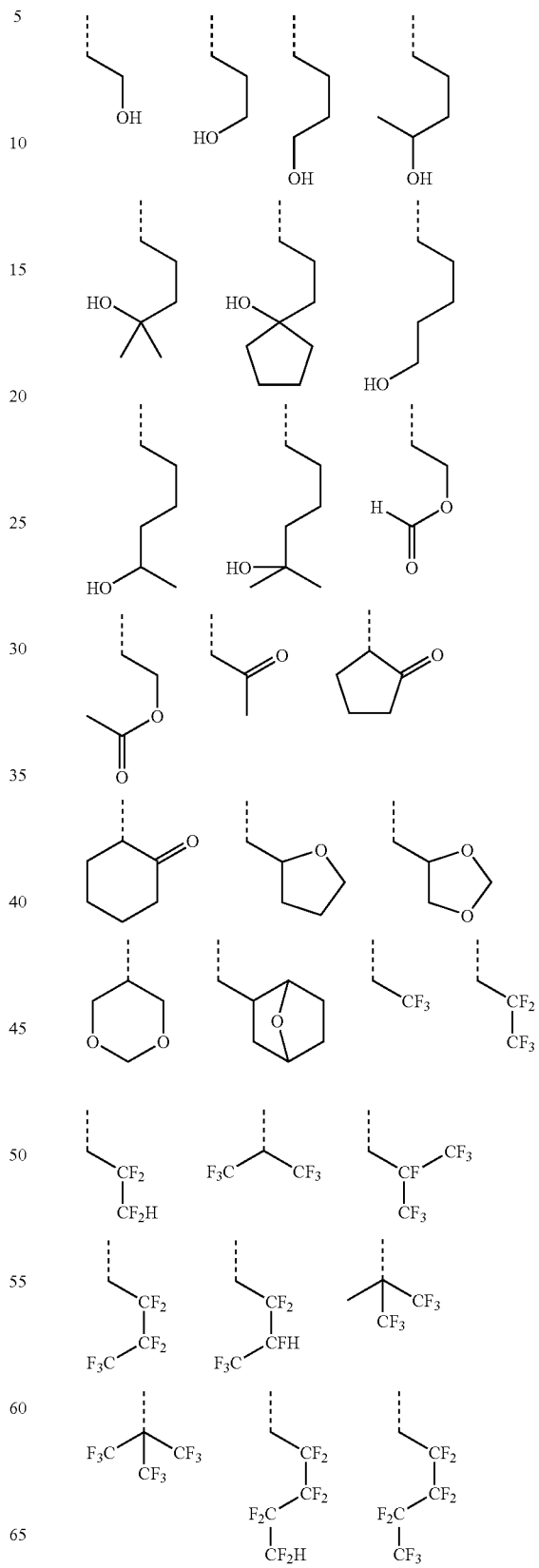

-continued

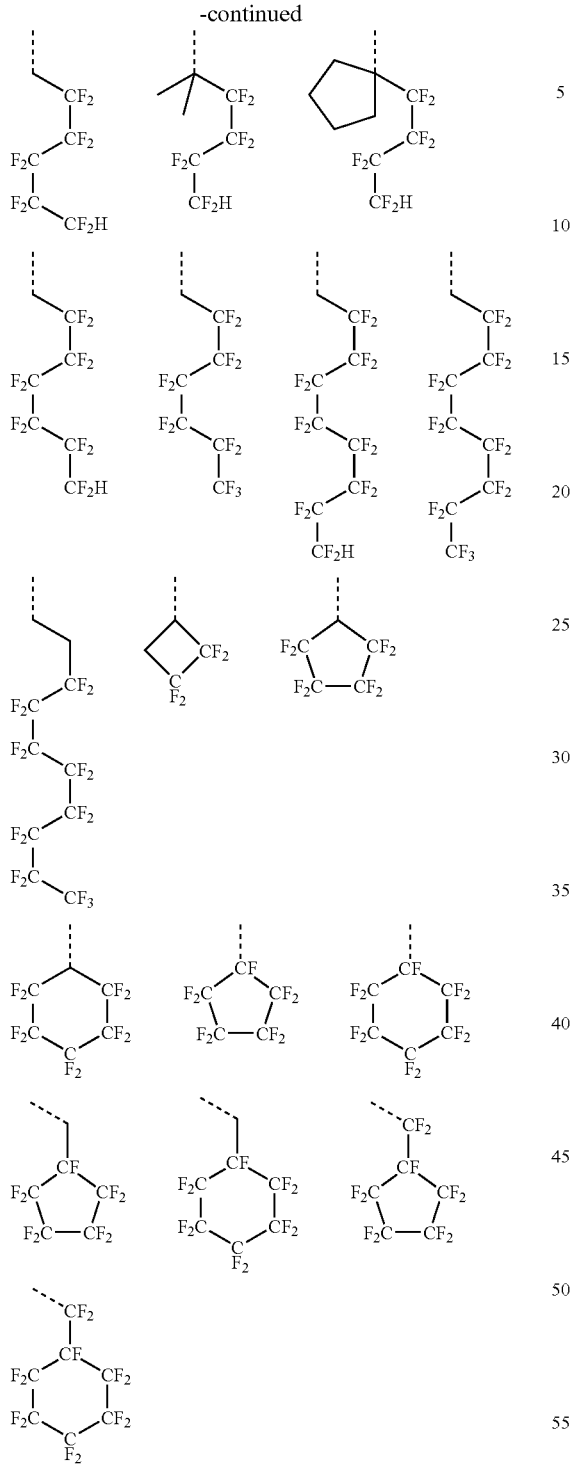

The broken line indicates a valence bond.

Of the above examples of the group $R^{23}$, preferred are methyl, 1-methylcyclopentyl, 1-ethylcyclopentyl, 1-methylcyclohexyl, 1-ethylcyclohexyl, 2-methyladamantan-2-yl, 2-ethyladamantan-2-yl, 8-methyltricyclo[5.2.1.0$^{2,6}$]decan-8-yl, 8-ethyltricyclo[5.2.1.0$^{2,6}$]decan-8-yl, and 4-ethyltetracyclo[6.2.1.1$^{3,6}$.0$^{2,7}$]dodecan-4-yl. A preferred example of W is $CH_2$.

Examples of suitable monomers from which the recurring units of formula (5L-1) are derived are given below.

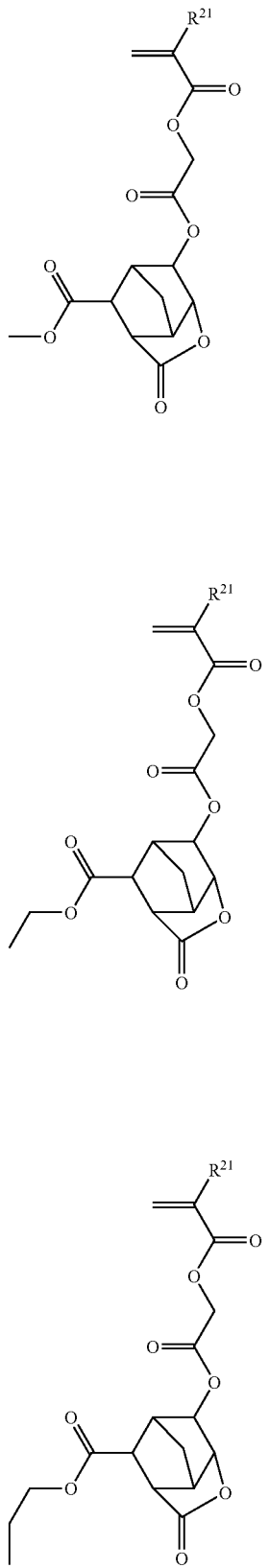

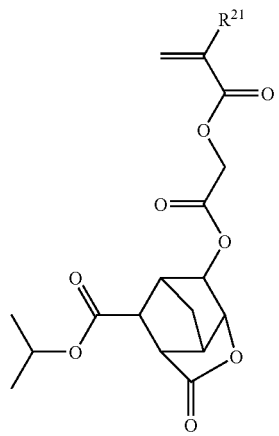
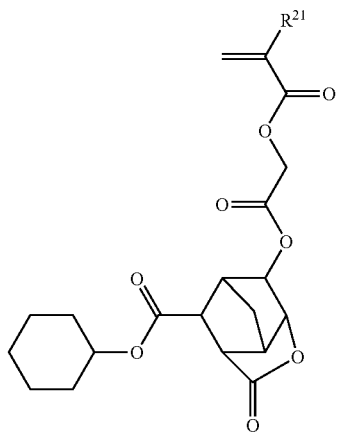
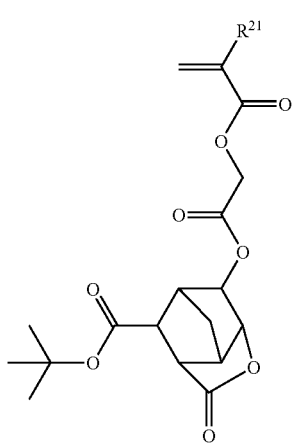
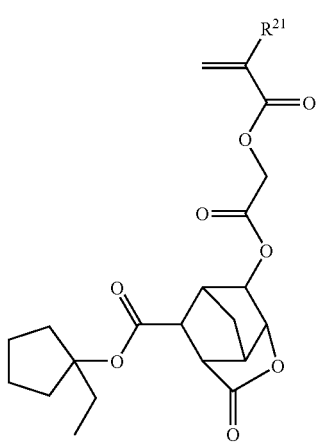
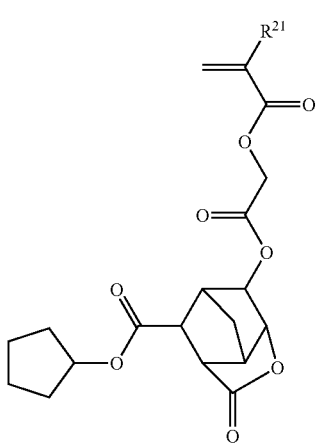
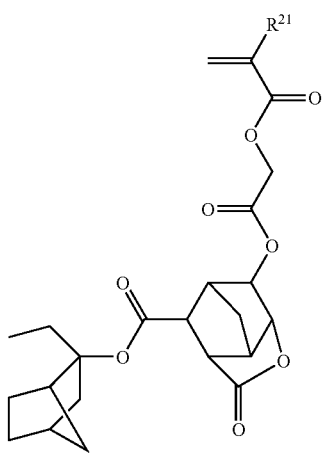

-continued
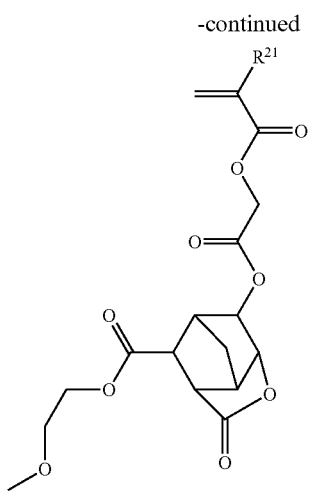
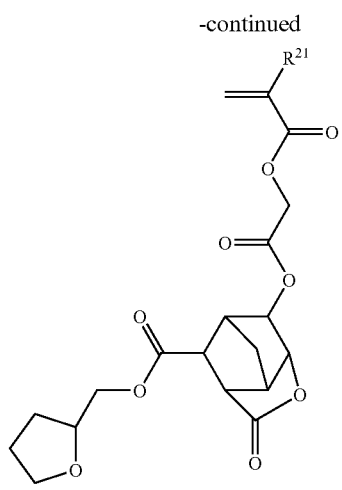
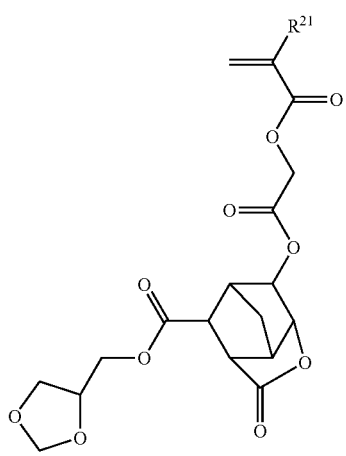
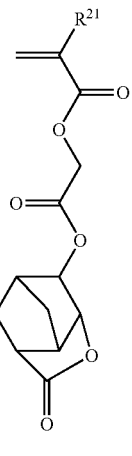
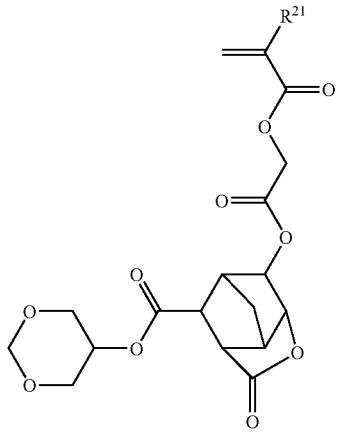
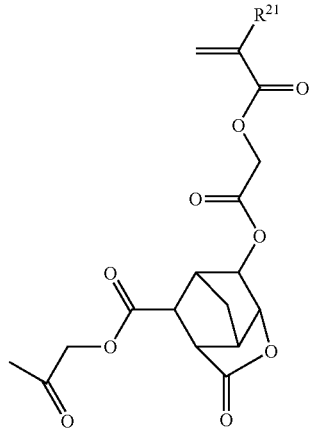

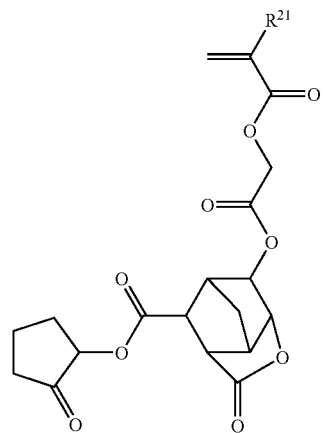
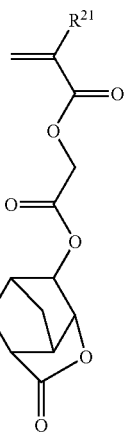
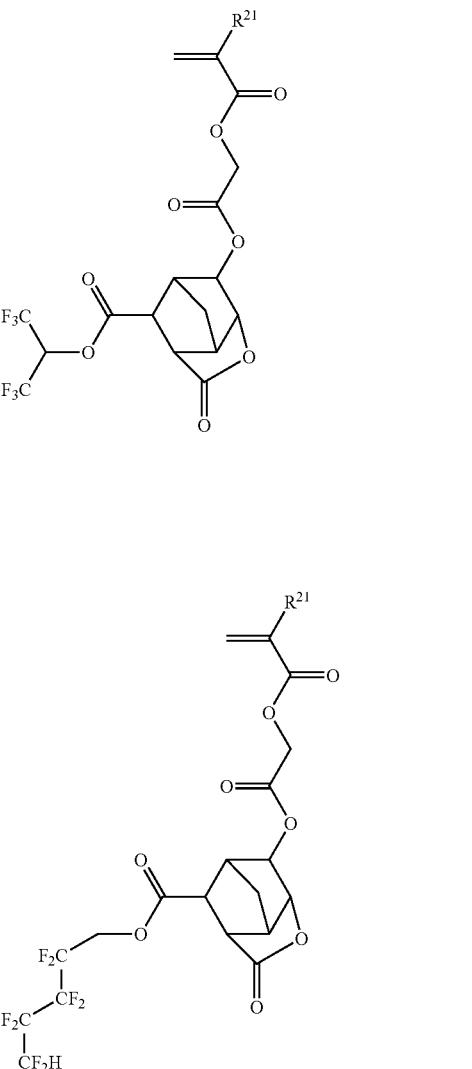
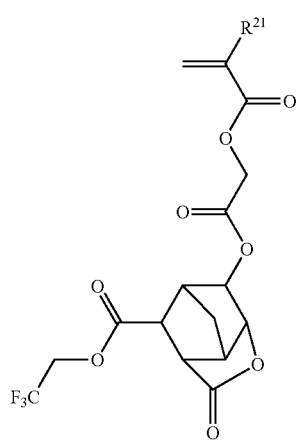
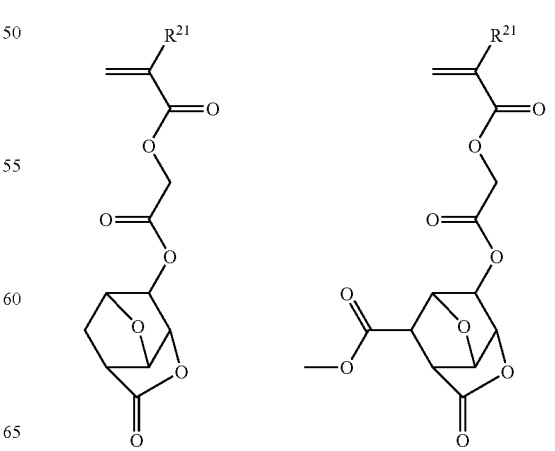

-continued
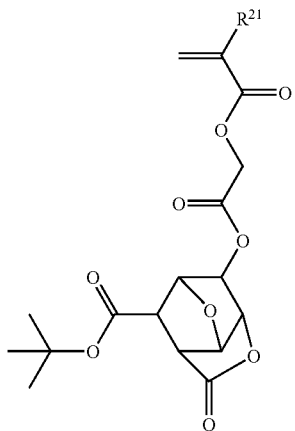
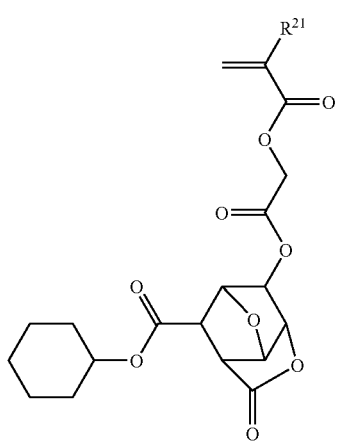
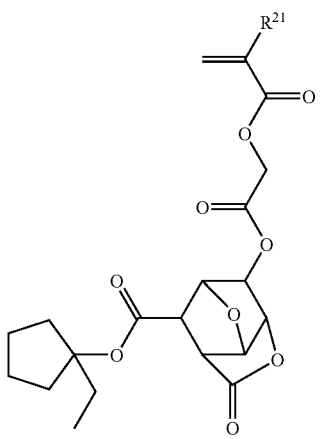
-continued
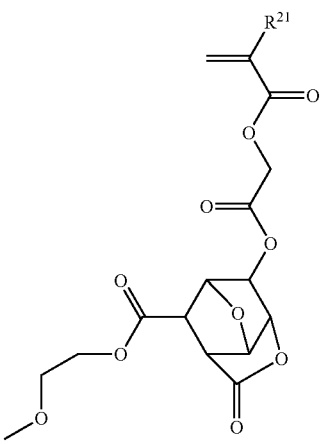
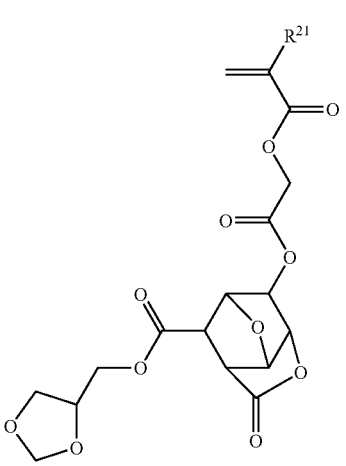
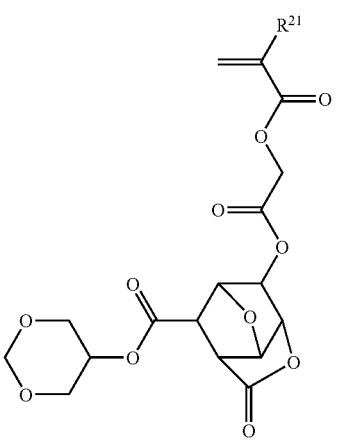

-continued
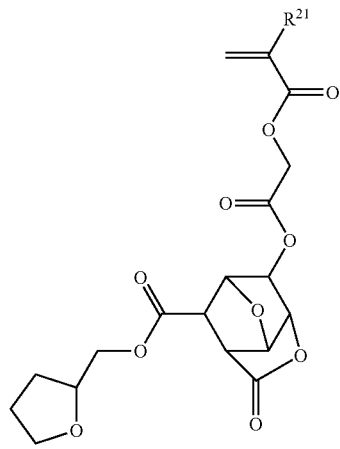
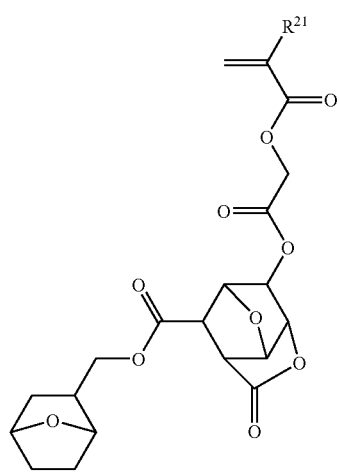
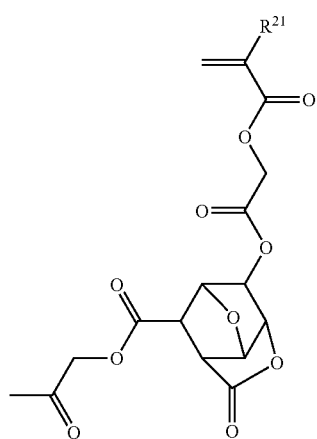
-continued
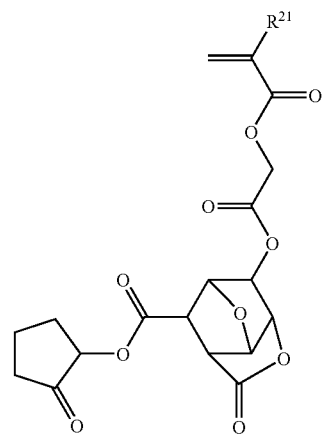
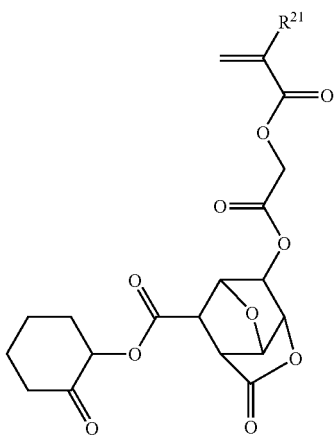
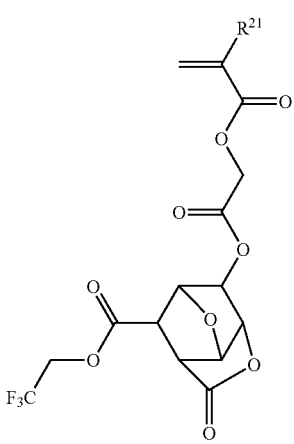

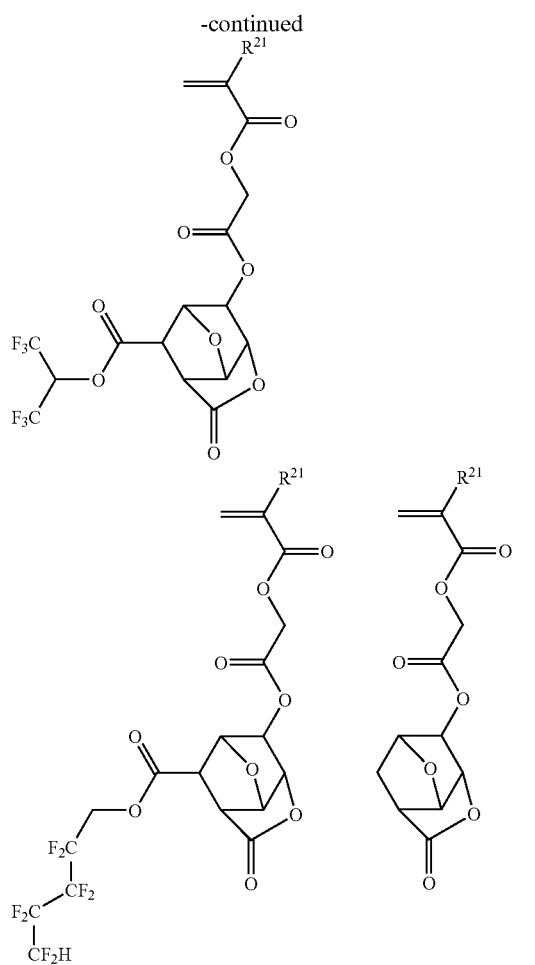

It is noted that the monomers from which the recurring units of formula (5L-1) wherein M=1 are derived are described in JP-A 2008-031298. The monomers with M=3 may be synthesized as are the monomers with M=1 except that the reactant, chloroacetyl chloride is replaced by chlorobutyric acid chloride.

Illustrative, non-limiting examples of the recurring units of formula (11) are given below.

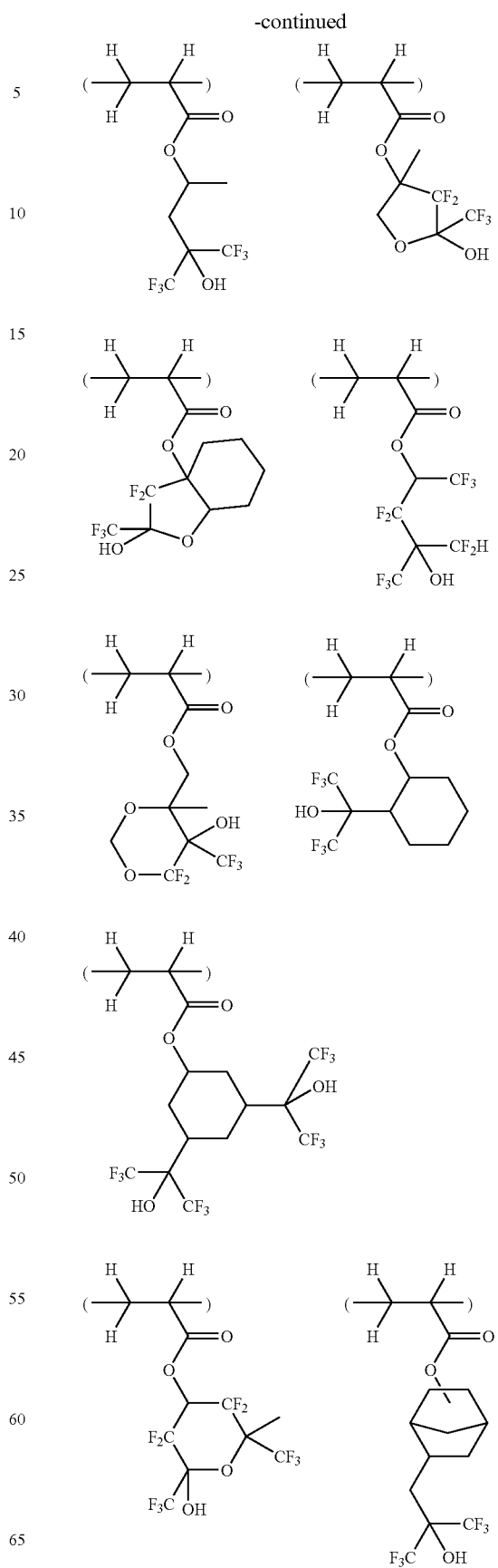

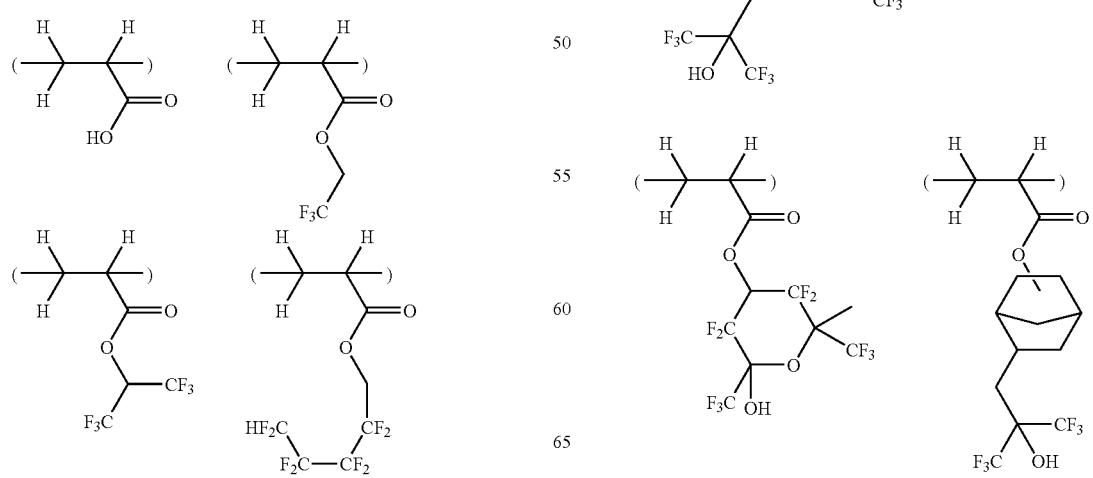

-continued
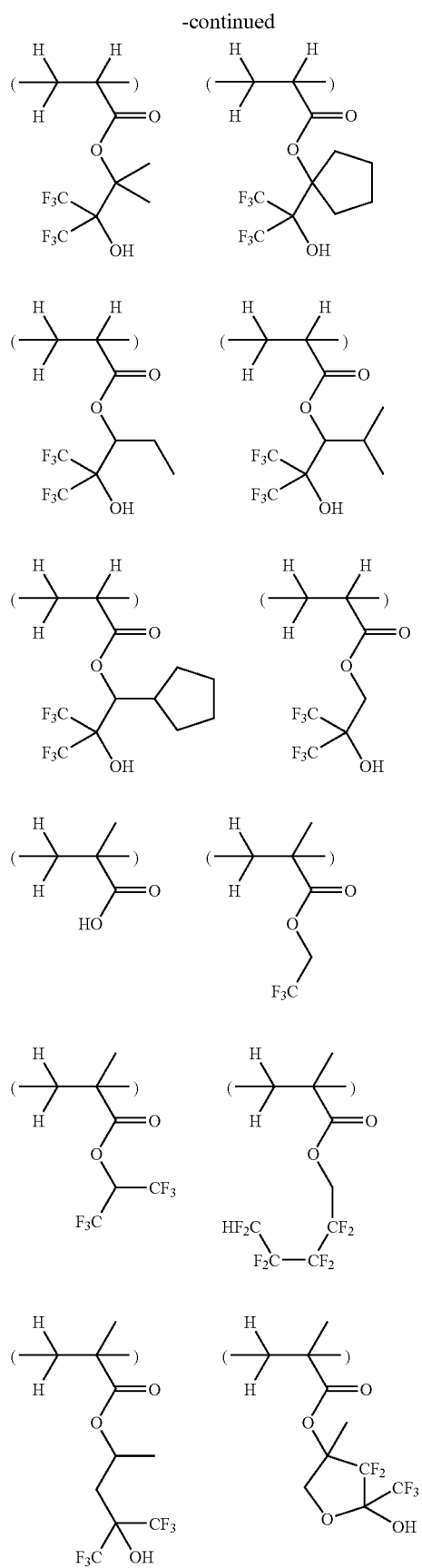
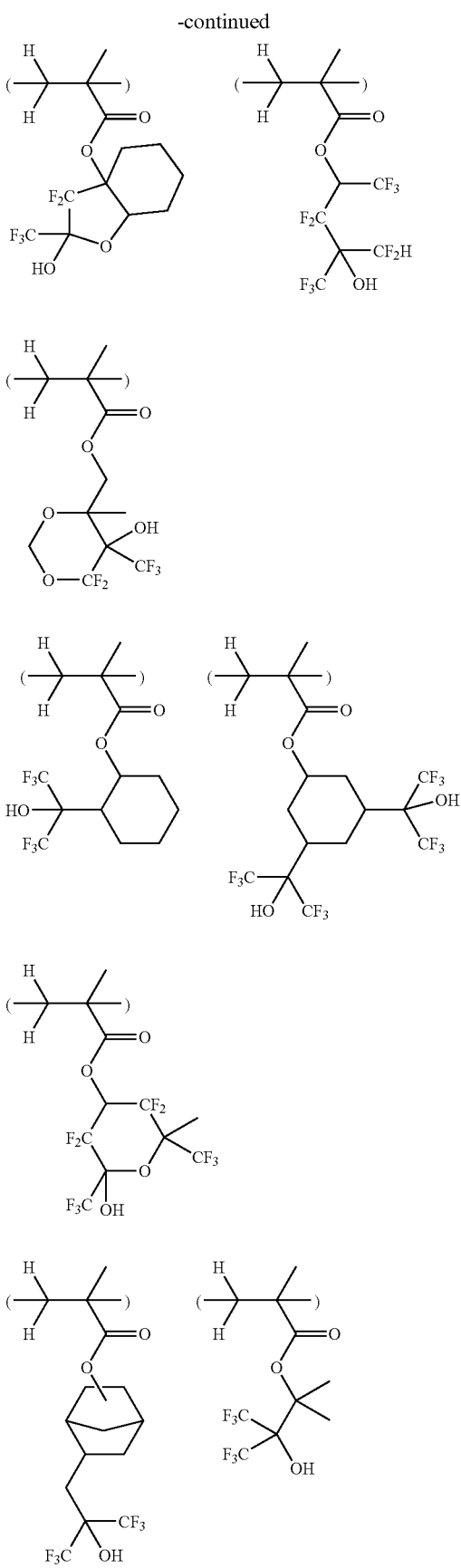

-continued

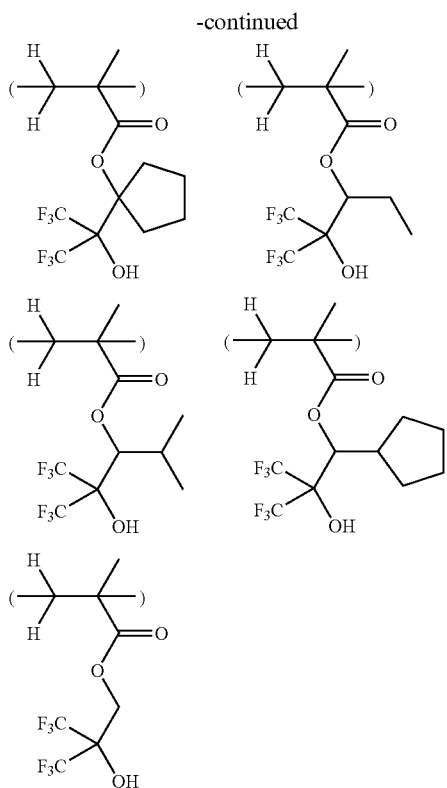

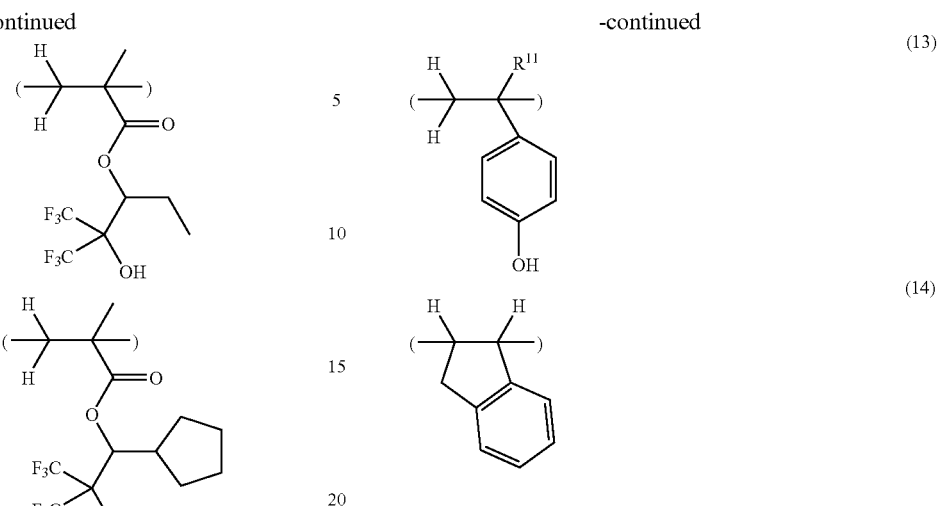

The polymer of the invention may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo[6.2.1.1$^{3,6}$.0$^{2,7}$]dodecene derivatives, and unsaturated acid anhydrides such as itaconic anhydride.

While the polymer used herein is applicable to the ArF lithography, it is also applicable to other lithography processes such as KrF, EB and EUV lithography.

In a further embodiment, the polymer used herein may comprise recurring units of at least one selected from the general formulae (12) to (14) and optionally, recurring units of at least one selected from the general formulae (8) to (11) described above.

Herein, $R^{11}$ and XA are as defined above, and G is an oxygen atom or carboxyl group (—C(=O)O—).

Under the action of an acid, a polymer comprising recurring units of formula (12) is decomposed to generate a phenolic hydroxyl group and/or carboxylic acid and turns into an alkali-soluble polymer. The acid labile groups represented by XA may be selected from a variety of such groups, for example, groups of the general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, which have been described above.

Illustrative, non-limiting examples of the recurring units of formula (12) are given below.

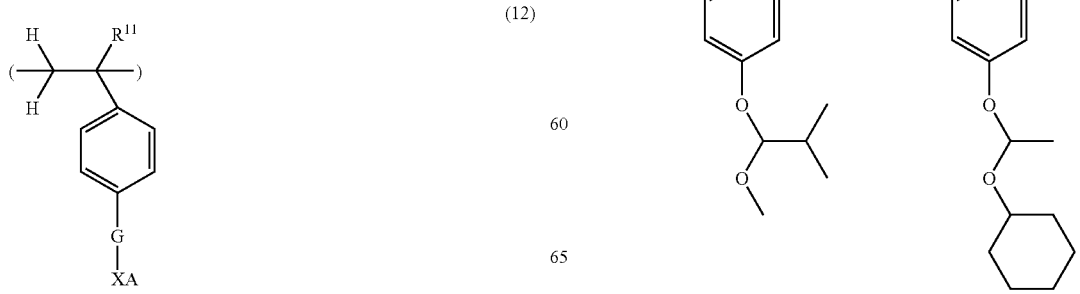

-continued

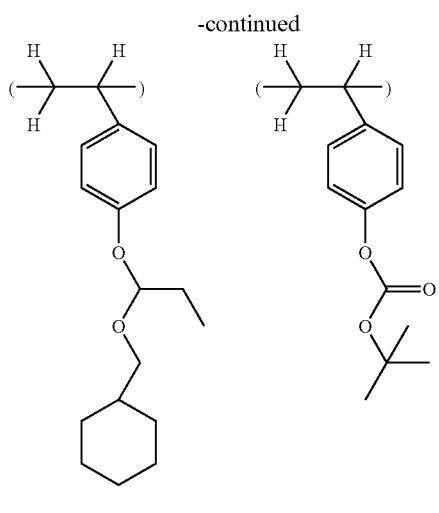

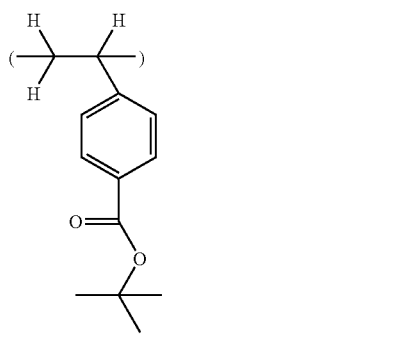

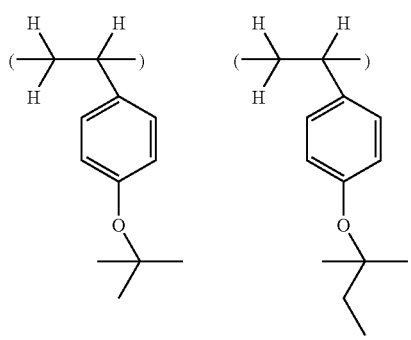

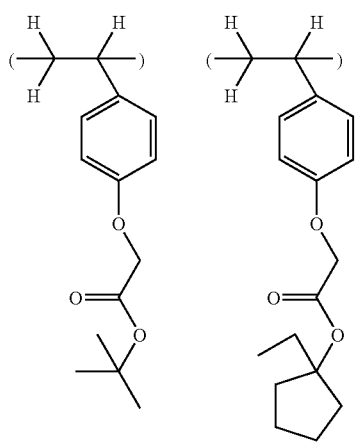

-continued

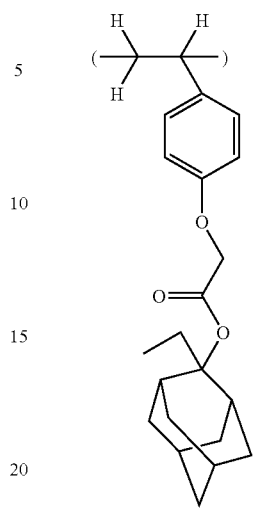

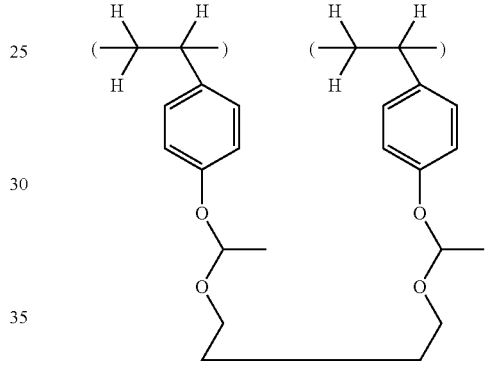

When the polymer contains recurring units having formulae (8) to (11) in addition to the recurring units of at least one type having formulae (12) to (14), the inclusion of recurring units having formula (8) is preferred.

Accordingly, the preferred base resin used herein is a polymer comprising recurring units having formula (8) and/or (12) and recurring units of at least one type selected from formulae (9), (10), (11), (13), and (14).

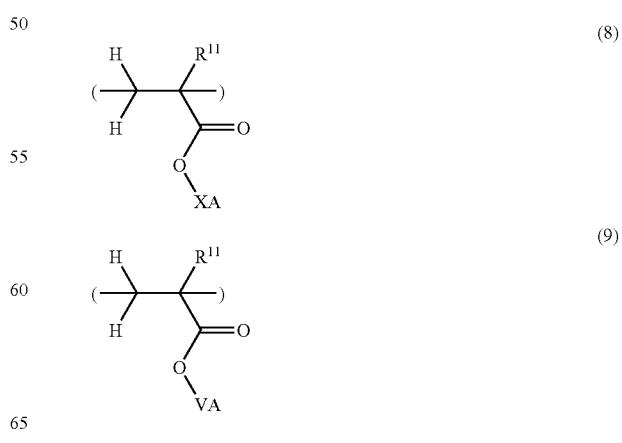

-continued

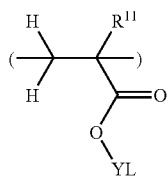
(10)

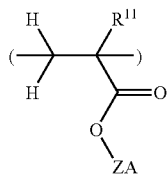
(11)

Herein, $R^{11}$ is hydrogen, fluorine, methyl or trifluoromethyl. VA is a polar radical-containing substituent group of 1 to 20 carbon atoms. Examples of VA include

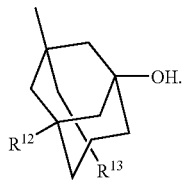

$R^{11}$ and $R^{13}$ are each independently hydrogen or hydroxyl. XA is an acid labile group, YL is a lactone structure-containing substituent group, and ZA is hydrogen, a $C_1$-$C_{15}$ fluoroalkyl group or fluoroalcohol-containing $C_1$-$C_{15}$ substituent group.

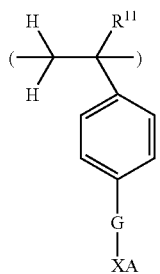
(12)

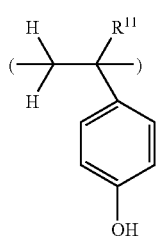
(13)

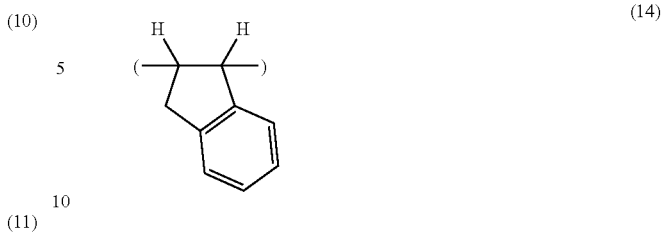
(14)

Herein $R^{11}$ and XA are as defined above, and G is an oxygen atom or carboxyl group (—C(=O)O—).

The polymer of the invention comprising recurring units of at least one type selected from formulae (12) to (14) may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[$6.2.1.1^{3,6}.0^{2,7}$]dodecene derivatives, and norbornadienes, and unsaturated acid anhydrides such as itaconic anhydride, as well as styrene, acenaphthylene. vinylnaphthalene, hydroxyvinylnaphthalene, and other monomers.

It is noted that the polymer used herein may have a weight average molecular weight (Mw) of about 1,000 to about 500,000, and preferably about 3,000 to about 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards or a light scattering method.

In the polymer used herein, the preferred proportion of respective recurring units derived from discrete monomers may fall, for example, in the range (molt) shown below, but is not limited thereto. The polymer may consist essentially of:

(I) from more than 1 mol % to 50 mol %, preferably 5 to 40 mol %, and more preferably 10 to 30 mol % of constituent units of one or more type having formula (8) and/or (12);

(II) from 50 mol % to 99 mol %, preferably 60 to 95 mol %, and more preferably 70 to 90 mol % of constituent units of one or more type selected from formulae (9a), (10) and (11) and/or formulae (13) and (14); and optionally, (III) from 0 mol % to 80 mol %, preferably 0 to 70 mol %, and more preferably 0 to 50 mol % of constituent units of one or more type derived from the additional monomer(s).

The polymer used herein may be prepared through copolymerization reaction of selected monomers. While various modes of copolymerization reaction may be used, the preferred modes are radical polymerization, anionic polymerization and coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (a) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

The polymer prepared by any mode of polymerization as described above may be used in a negative resist composition, provided that some or all acid labile groups on the polymer are deprotected. Alternatively, the polymer in which acid labile groups have been deprotected can be modified by introducing acid labile groups therein again whereby substituent groups different from the acid labile groups initially introduced during polymerization are introduced into the polymer.

For example, once a polymer is formed through radical polymerization of 4-ethoxyethoxystyrene, ethoxyethoxy groups are eliminated from the polymer using acetic acid, pyridinium tosylate or the like, whereupon the polymer may be converted into a copolymer with polyhydroxystyrene. The resultant copolymer may be used as a base resin in a negative resist composition. Alternatively, hydroxystyrene units in the resultant copolymer may be reacted with di-tert-butyl dicarbonate, tert-butyl chloroacetate, vinyl ethers or the like, whereby acid labile groups different from the acid labile groups (i.e., ethoxyethoxy groups) initially introduced during polymerization are introduced.

Hydrogenated products of ring-opening metathesis polymers (ROMP) may be synthesized by the method described in Examples of JP-A 2003-66612. Examples of such hydrogenated polymers include, but are not limited to, the following combinations of recurring units.

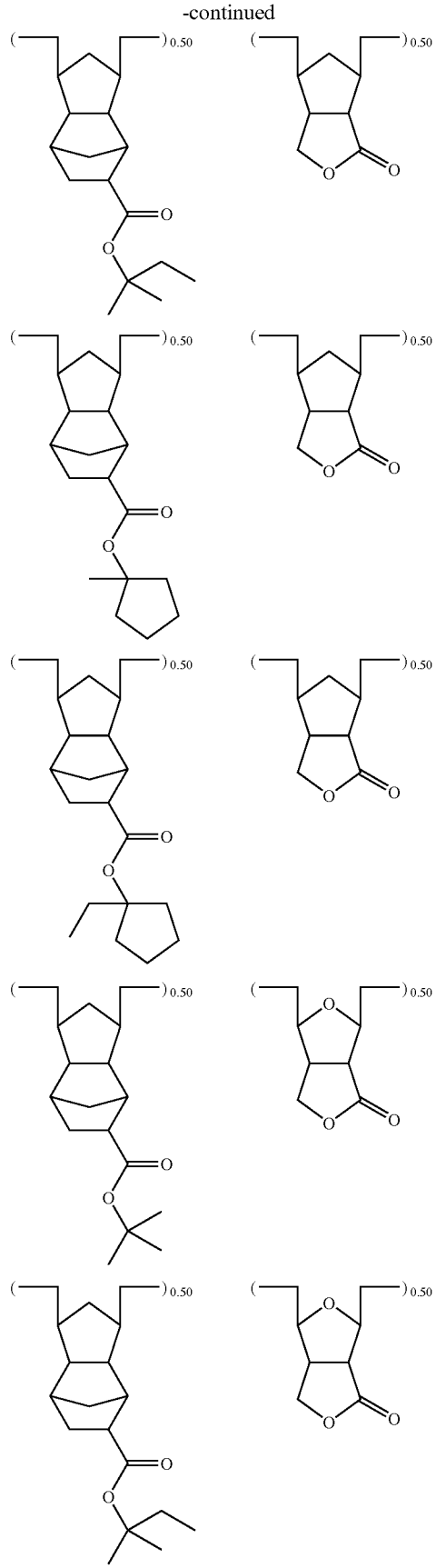

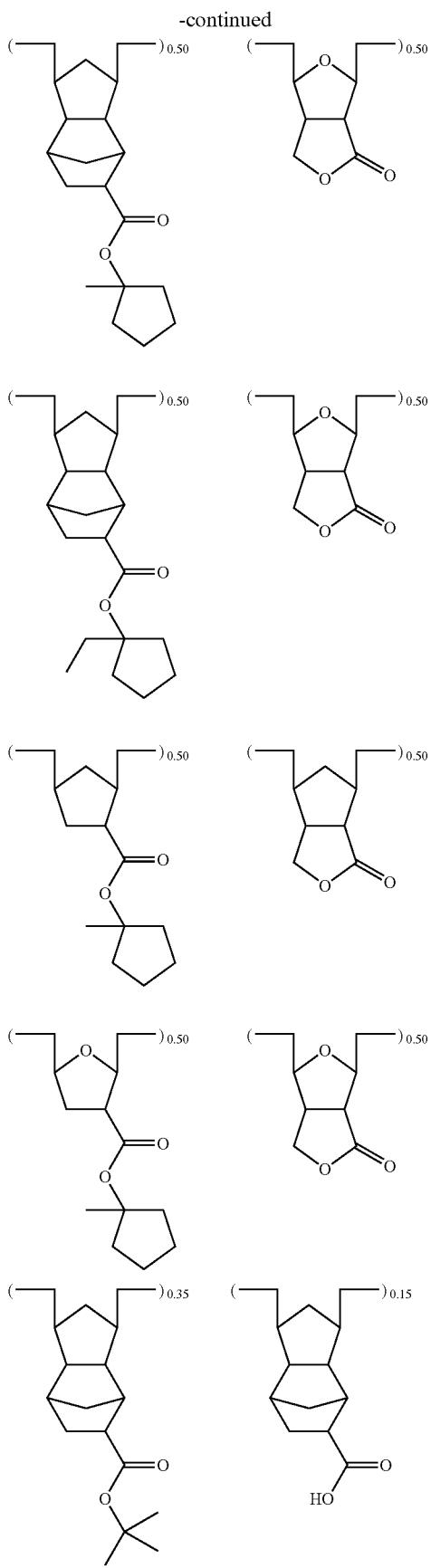
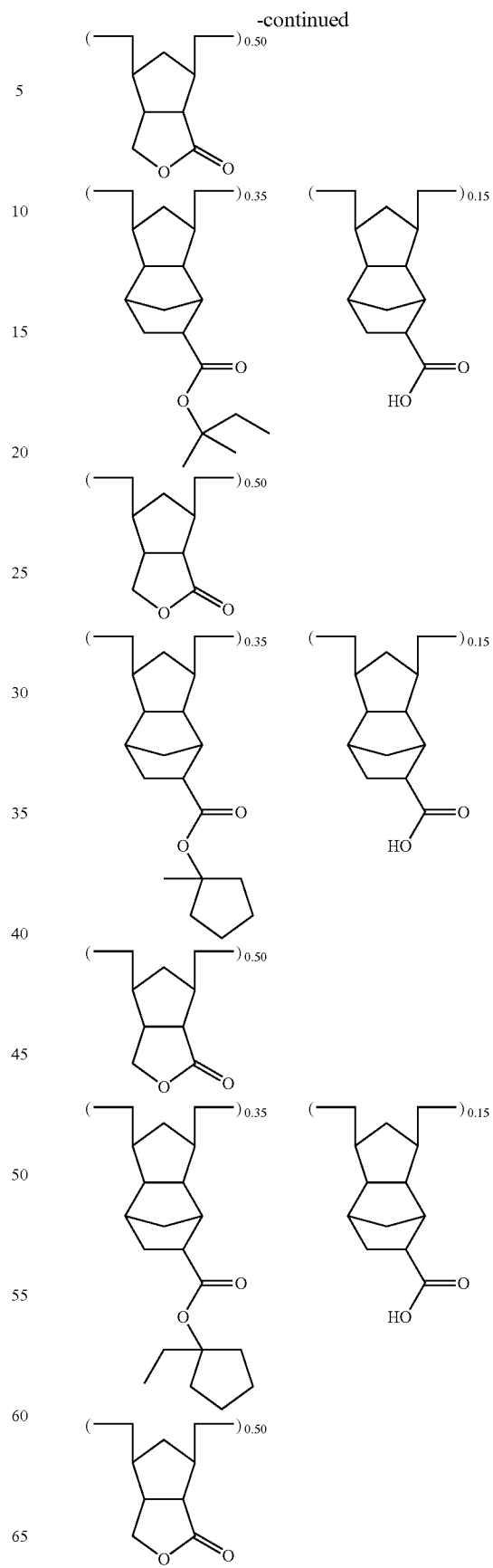

-continued

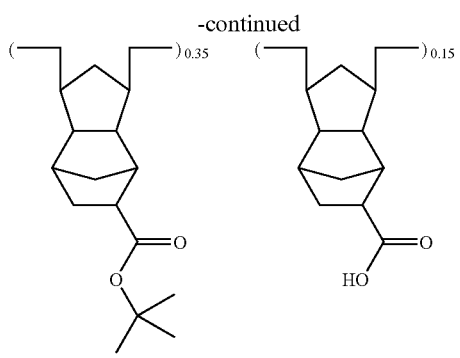
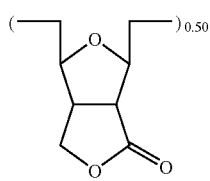
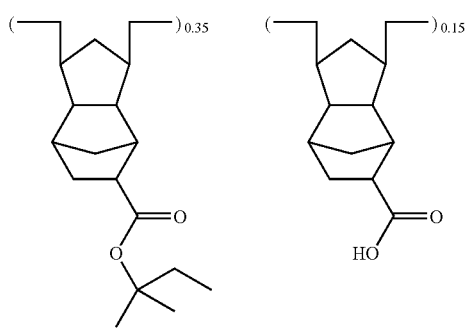
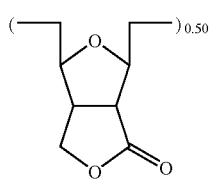
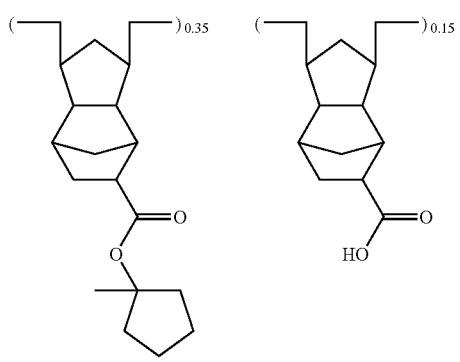
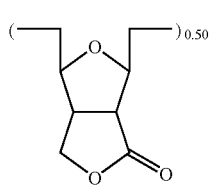

-continued

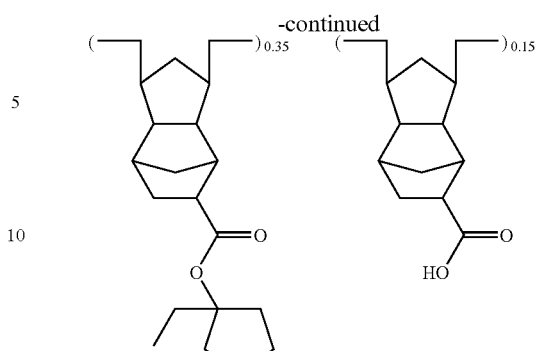
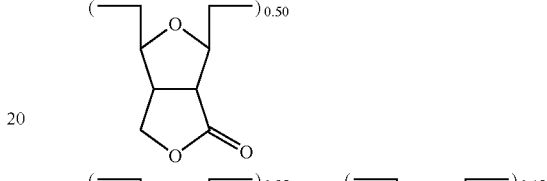
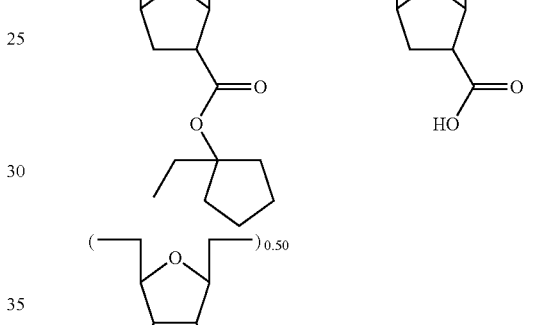
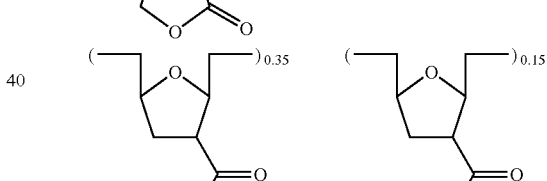
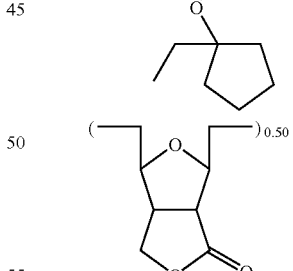

In the resist composition, the polymers may be added alone or in admixture of two or more. The use of plural polymers allows for easy adjustment of resist properties.

Component D

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Amine compounds of the following general formula (B)-1 are suitable.

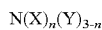
(B)-1

In the formula, n is equal to 1, 2 or 3. The side chain X is independently selected from groups of the following general formulas (X)-1 to (X)-3. The side chain Y is independently hydrogen or a straight, branched or cyclic $C_1$-$C_{20}$ alkyl group in which some or all hydrogen atoms may be substituted by fluorine atoms and which may contain an ether or hydroxyl group. Two or three X may bond together to form a ring.

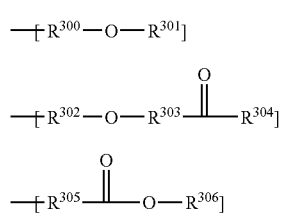

(X)-1

(X)-2

(X)-3

Herein $R^{300}$, $R^{302}$ and $R^{305}$ are independently straight or branched $C_1$-$C_4$ alkylene groups; $R^{301}$ and $R^{304}$ are independently hydrogen or straight or branched or cyclic $C_1$-$C_{50}$ alkyl groups in which some or all hydrogen atoms may be substituted by fluorine atoms and which may contain at least one hydroxyl group, ether group, ester group or lactone ring; $R^{303}$ is a single bond or a straight or branched $C_1$-$C_4$ alkylene group; $R^{306}$ is a straight, branched or cyclic $C_1$-$C_{50}$ alkyl group in which some or all hydrogen atoms may be substituted by fluorine atoms and which may contain at least one hydroxyl group, ether group, ester group or lactone ring.

Also useful are one or more of cyclic structure-bearing amine compounds having the following general formula (B)-2.

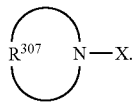
(B)-2

Herein X is as defined above, and $R^{307}$ is a straight or branched $C_2$-$C_{20}$ alkylene group in which some or all hydrogen atoms may be substituted by fluorine atoms and which may contain one or more carbonyl, ether, ester or sulfide groups.

Also, one or more of cyano-bearing amine compounds having the following general formulae (B)-3 to (B)-6 may be used.

(B)-3

(B)-4

(B)-5

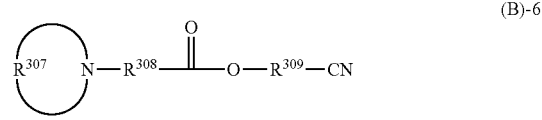
(B)-6

Herein, X, $R^{307}$ and n are as defined in formula (B)-1, and $R^{308}$ and $R^{309}$ are each independently a straight or branched $C_1$-$C_4$ alkylene group.

Also included are amine compounds having an imidazole structure and a polar functional group, represented by the general formula (B)-7.

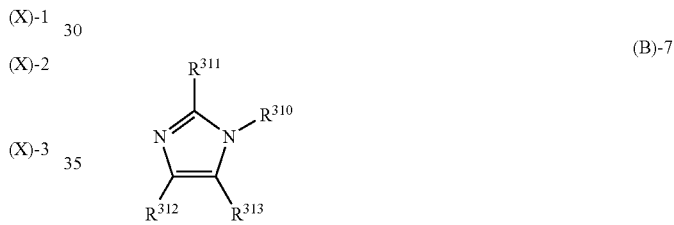
(B)-7

Herein, $R^{310}$ is a straight, branched or cyclic $C_2$-$C_{50}$ alkyl group in which some or all hydrogen atoms may be substituted by fluorine atoms and which may have at least one polar functional group selected from among ester, acetal, cyano, hydroxyl, carbonyl, ether, sulfide, carbonate, and other groups. $R^{311}$, $R^{312}$ and $R^{313}$ are each independently a hydrogen atom, a straight, branched or cyclic $C_1$-$C_{10}$ alkyl group, aryl group or aralkyl group.

Also included are amine compounds having a benzimidazole structure and a polar functional group, represented by the general formula (B)-8.

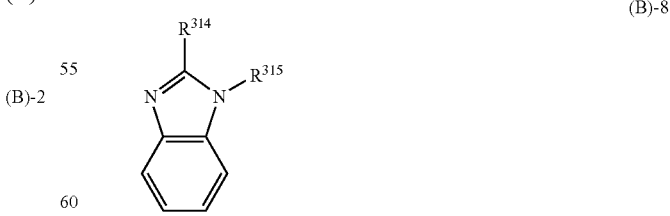
(B)-8

Herein, $R^{314}$ is a hydrogen atom, a straight, branched or cyclic $C_1$-$C_{50}$ alkyl group, aryl group or aralkyl group. $R^{315}$ is a straight, branched or cyclic $C_1$-$C_{50}$ alkyl group in which some or all hydrogen atoms may be substituted by fluorine atoms and which may have at least one polar functional group selected from among ester, acetal, cyano, hydroxyl, carbonyl, ether, sulfide, carbonate and other groups.

Further included are heterocyclic nitrogen-containing compounds having a polar functional group, represented by the general formulae (B)-9 and (B)-10.

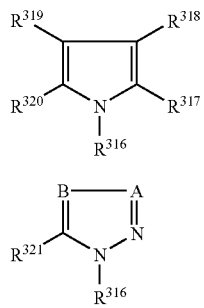

(B)-9

(B)-10

Herein, A is a nitrogen atom or $=C-R^{322}$. B is a nitrogen atom or $=C-R^{323}$. $R^{316}$ is a straight, branched or cyclic $C_2$-$C_{50}$ alkyl group in which some or all hydrogen atoms may be substituted by fluorine atoms and which may have at least one polar functional group selected from among ester, acetal, cyano, hydroxyl, carbonyl, ether, sulfide, carbonate and other groups. $R^{317}$, $R^{318}$, $R^{319}$ and $R^{320}$ are each independently a hydrogen atom, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring with the carbon atoms to which they are attached. $R^{321}$ is a hydrogen atom, a straight, branched or cyclic $C_1$-$C_{10}$ alkyl group or aryl group. $R^{322}$ and $R^{323}$ each are a hydrogen atom, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are amine compounds having an aromatic carboxylic acid ester structure, represented by the general formulae (B)-11 to (B)-14.

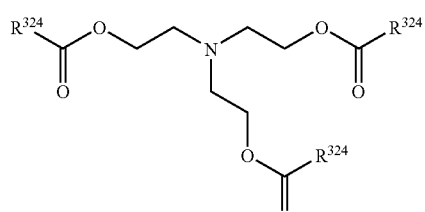

(B)-11

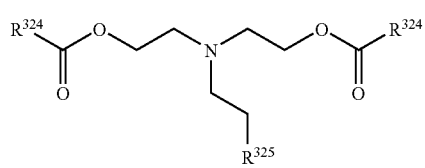

(B)-12

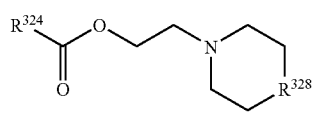

(B)-13

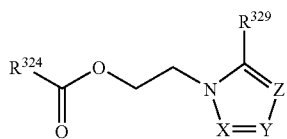

(B)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or $-O(CH_2CH_2O)_n-$ group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_1C_{20}$ aromatic ring or $C_2$-$C_{20}$ hetero-aromatic ring with the carbon atoms to which they are attached.

Further included are amine compounds of 7-oxanorbornane-2-carboxylic ester structure, represented by the general formula (B)-15.

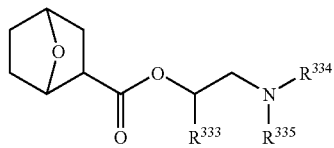

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$ may bond together to form a heterocyclic or heteroaromatic ring of 2 to 20 carbon atoms with the nitrogen atom to which they are attached.

Illustrative examples of the quencher used herein include the following, but are not limited thereto.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N'-dimethylmethylenediamine, N,N'-dimethylethylenediamine, and dimethyltetraethylenepentamine. Examples of suitable tertiary aliphatic amines include trimethylamine, triethylamine, tri-n-propylamine, triisopropylamine, tri-n-butylamine, truisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazane derivatives, pyrroline derivatives (e.g., pyrroline and 2-methyl-l-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). A suitable nitrogen-containing compound with sulfonyl group is 3-pyridinesulfonic acid. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethyletha-nolamine, truisopropanolamine, 2,21-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl) pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

Illustrative examples of suitable tertiary amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxy-carbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, tris(2-benzoyloxyethyl)amine, tris[2-(4-methoxybenzoyloxy)ethyl]amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)

ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and β-(diethylamino)-67-valerolactone.

Illustrative examples of the cyclic structure-bearing amine compounds include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]imidazole, 1-[2-[(2-methoxyethoxy)methoxy]ethyl]benzimidazole, 1-[2-[(2-methoxyethoxy)methoxy]ethyl]-2-phenylbenzimidazole, 1-[2-[2-[(2-methoxyethoxy)ethoxy]ethyl]pyrrolidine, 1-[2-[2-[(2-methoxyethoxy)ethoxylethyl]piperidine, 4-[2-[2-[(2-methoxyethoxy)ethoxy]ethyl]morpholine, 1-[2-[2-[(2-methoxyethoxy)ethoxy]ethyl]imidazole, 1-[2-[2-[(2-methoxyethoxy)ethoxy]ethyl]benzimidazole, 1-[2-[2-[(2-methoxyethoxy)ethoxy]ethyl]-2-phenylbenzimidazole, 1-[2-[2-[(2-butoxyethoxy)ethoxy]ethyl]pyrrolidine, 1-[2-[2-[(2-butoxyethoxy)ethoxy]ethyl]piperidine, 4-[2-[2-[(2-butoxyethoxy)ethoxy]ethyl]morpholine, 1-[2-[2-[(2-butoxyethoxy)ethoxylethyl]imidazole, 1-[2-[2-[(2-butoxyethoxy)ethoxy]ethyl]benzimidazole, 1-[2-[2-[(2-butoxyethoxy)ethoxy]ethyl]-2-phenylbenzimidazole, 1-[2-[2-[2-[(2-methoxyethoxy)ethoxy]ethoxylethyl]pyrrolidine, 1-[2-[2-[2-[(2-methoxyethoxy)ethoxy]ethoxy]ethyl]piperidine, 4-[2-[2-[2-[(2-methoxyethoxy)ethoxy]ethoxy]ethyl]morpholine, 1-[2-[2-[2-[(2-methoxyethoxy)ethoxy]ethoxy]ethyl]imidazole, 1-[2-[2-[2-[(2-methoxyethoxy)ethoxy]ethoxy]ethyl]benzimidazole, 1-[2-[2-[2-[(2-methoxyethoxy)ethoxy]ethoxy]ethyl]-2-phenyl-benzimidazole, 4-[2-[2-[2-[(2-butoxyethoxy)ethoxy]ethoxy]ethyl]morpholine, 2-(1-pyrrolidinyl)ethyl acetate, 2-piperidinoethyl acetate, 2-morpholinoethyl acetate, 2-(1-imidazolyl)ethyl acetate, 2-(1-benzimidazoyl)ethyl acetate, 2-(2-phenyl-1-benzimidazolyl)ethyl acetate, 2-methoxyethyl morpholinoacetate, 2-(1-pyrrolidinyl)ethyl 2-methoxyacetate, 2-piperidinoethyl 2-methoxyacetate, 2-morpholinoethyl 2-methoxyacetate, 2-(1-imidazolyl)ethyl 2-methoxyacetate, 2-(1-benziiidazolyl)ethyl 2-methoxyacetate, 2-(2-phenyl-1-benzimidazolyl)ethyl 2-methoxyacetate, 2-(1-pyrrolidinyl)ethyl 2-(2-methoxyethoxy)acetate, 2-piperidinoethyl 2-(2-methoxyethoxy)acetate, 2-morpholinoethyl 2-(2-methoxyethoxy)acetate, 2-(1-imidazolyl)ethyl 2-(2-methoxyethoxy)acetate, 2-(1-benzimidazolyl)ethyl 2-(2-methoxyethoxy)acetate, 2-(2-phenyl-1-benzimidazolyl)ethyl 2-(2-methoxyethoxy)acetate, 2-(1-pyrrolidinyl)ethyl 2-[2-(2-methoxyethoxy)ethoxy]acetate, 2-piperidinoethyl 2-[2-(2-methoxyethoxy)ethoxy]acetate, 2-morpholinoethyl 2-[2-(2-methoxyethoxy)ethoxy]acetate, 2-(1-imidazolyl) ethyl 2-[2-(2-methoxyethoxy]ethoxylacetate, 2-(1-benzimidazolyl)ethyl 2-[2-(2-methoxyethoxy)ethoxy]acetate, 2-(2-phenyl-1-benzimidazolyl)ethyl 2-[2-(2-methoxyethoxy)-ethoxy]acetate, 2-morpholinoethyl butyrate. 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl behenate, 2-morpholinoethyl cholate, 2-morpholinoethyl tris(O-acetyl)cholate, 2-morpholinoethyl tris(O-formyl)cholate, 2-morpholinoethyl dehydrocholate, 2-morpholinoethyl cyclopentanecarboxylate, 2-morpholinoethyl cyclohexanecarboxylate, 2-(1-pyrrolidinyl)ethyl 7-oxanorbornane-2-carboxylate, 2-piperidinoethyl 7-oxanorbornane-2-carboxylate, 2-morpholinoethyl 7-oxanorbornane-2-carboxylate, 2-(1-imidazolyl)ethyl 7-oxanorbornane-2-carboxylate, 2-(1-benzimidazolyl)ethyl 7-oxanorbornane-2-carboxylate, 2-(2-phenyl-1-benzimidazolyl)ethyl 7-oxanorbornane-2-carboxylate, 2-morpholinoethyl adamantanecarboxylate, 2-(1-pyrrolidinyl)ethyl formate, 2-piperidinoethyl propionate, 2-morpholinoethyl acetoxyacetate, 2-(1-pyrrolidinyl)ethyl methoxyacetate, 2-(1-pyrrolidinyl)ethyl benzoate, 2-piperidinoethyl benzoate, 2-morpholinoethyl benzoate, 2-(1-imidazolyl)ethyl benzoate. 2-(1-benzimidazolyl)ethyl benzoate, 2-(2-phenyl-1-benzimidazolyl)ethyl benzoate, 2-(1-pyrrolidinyl)ethyl 4-methoxybenzoate, 2-piperidinoethyl 4-methoxybenzoate, 2-morpholinoethyl 4-methoxybenzoate, 2-(1-imidazolyl)ethyl 4-methoxybenzoate, 2-(1-benzimidazolyl)ethyl 4-methoxybenzoate, 2-(2-phenyl-1-benzimidazolyl)ethyl 4-methoxybenzoate, 2-(1-pyrrolidinyl)ethyl 4-phenylbenzoate, 2-piperidinoethyl 4-phenylbenzoate, 2-morpholinoethyl 4-phenylbenzoate, 2-(1-imidazolyl)ethyl 4-phenylbenzoate, 2-(1-benzimidazolyl)ethyl 4-phenylbenzoate, 2-(2-phenyl-1-benzimidazolyl)ethyl 4-phenylbenzoate, 2-(1-pyrrolidinyl)ethyl 1-naphthalenecarboxylate, 2-piperidinoethyl 1-naphthalenecarboxylate, 2-morpholinoethyl 1-naphthalenecarboxylate, 2-(1-imidazolyl)ethyl 1-naphthalenecarboxylate, 2-(1-benzimidazolyl)ethyl 1-naphthalenecarboxylate, 2-(2-phenyl-1-benzimidazolyl)ethyl 1-naphthalenecarboxylate, 2-(1-pyrrolidinyl)ethyl 2-naphthalenecarboxylate, 2-piperidinoethyl 2-naphthalenecarboxylate, 2-morpholinoethyl 2-naphthalenecarboxylate, 2-(1-imidazolyl)ethyl 2-naphthalenecarboxylate, 2-(1-benzimidazolyl)ethyl 2-naphthalenecarboxylate, 2-(2-phenyl-1-benzimidazolyl)ethyl 2-naphthalenecarboxylate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)

propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, and ethyl 1-pyrrolidinylacetate.

Examples of the cyano-bearing amine compounds include 3-(dethylamino)propiononitrile, N,N-bis(2-hydroxyethyl)-3-aminopropionitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropionitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiono-nitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl)aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The quenchers may be used alone or in admixture of two or more. The quencher is preferably formulated in an amount of 0.001 to 5 parts, and especially 0.01 to 3 parts by weight, per 100 parts by weight of the base resin. Less than 0.001 phr of the quencher may achieve no addition effect whereas more than 5 phr may lead to too low a sensitivity.

Component B

In one preferred embodiment, the resist composition further contains (E) an auxiliary photoacid generator other than the photoacid generator corresponding to formula (1a) or (1b). It may be any compound capable of generating an acid upon exposure to high-energy radiation. Suitable auxiliary photoacid generators include sulfonium salts, iodonium salts, N-sulfonyloxydicarboxyimide, and oxime-O-arylsulfonate photoacid generators. Exemplary auxiliary photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy) naphthalene-2-sulfonate, 4-(p-toluenesulfonyloxy) naphthalene-1-sulfonate, 5-(p-toluenesulfonyloxy) naphthalene-1-sulfonate, 8-(p-toluenesulfonyloxy) naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo

[6.2.1.1³,⁶.0²,⁷]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris (substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations include diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethyloyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1³,⁶.0²,⁷]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris (substituted alkylsulfonyl)methide is tris(trifluoromethylsulfonyl)methide. Iodonium salts based on combination of the foregoing examples are included.

N-sulfonyloxydicarboxyimide photoacid generators include combinations of imide skeletons with sulfonates. Exemplary imide skeletons are succinimide, naphthalenedicarboximide, phthalimide, cyclohexyldicarboximide, 5-norbornene-2,3-dicarboximide, and 7-oxabicyclo[2.2.1]-5-heptene-2,3-dicarboximide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1³,⁶.0²,⁷]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Also useful are O-arylsulfonyl oxime and O-alkylsulfonyl oxime (oxime sulfonate) photoacid generators. They include oxime sulfonate compounds having an electron-withdrawing group (e.g., trifluoromethyl) for increased stability, as represented by the formula (Ox-1):

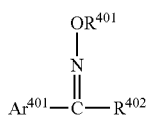

(Ox-1)

wherein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is a substituted or unsubstituted aromatic or hetero-aromatic group.

Examples include 2-[2,2,3,3,4,4,5,5-octafluoro-1-(nonafluorobutylsulfonyloxy-imino)pentyl]fluorene, 2-[2,2,3,3,4,4-pentafluoro-1-(nonafluorobutylsulfonyloxy-imino)butyl]fluorene, 2-[2,2,3,3,4,4,5,5,6,6-decafluoro-1-(nonafluorobutylsulfonyl-oxyimino)hexyl]fluorene, 2-[2,2,3,3,4,4,5,5-octafluoro-1-(nonafluorobutylsulfonyloxy-imino)pentyl]-4-biphenyl, 2-[2,2,3,3,4,4-pentafluoro-1-(nonafluorobutylsulfonyloxy-imino)butyl]-4-biphenyl, and 2-[2,2,3,3,4,4,5,5,6,6-decafluoro-1-(nonafluorobutyl-sulfonyloxyimino)hexyl]-4-biphenyl.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Among others, acid generators having the general formula (E)-1 are preferred.

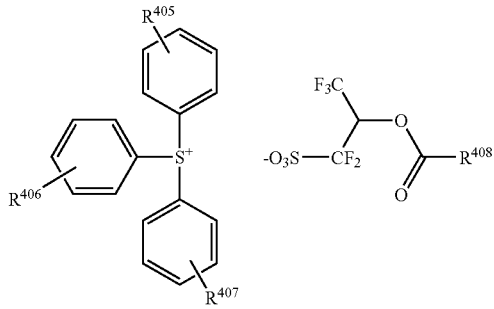

(E)-1

Herein $R^{405}$, $R^{406}$, and $R^{407}$ are each independently hydrogen or a straight, branched or cyclic, monovalent $C_1$-$C_{20}$ hydrocarbon group, typically an alkyl or alkoxy group, which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{408}$ is a straight, branched or cyclic, monovalent $C_7$-$C_{30}$ hydrocarbon group which may contain a heteroatom, examples of which are exemplified below, but are not limited thereto.

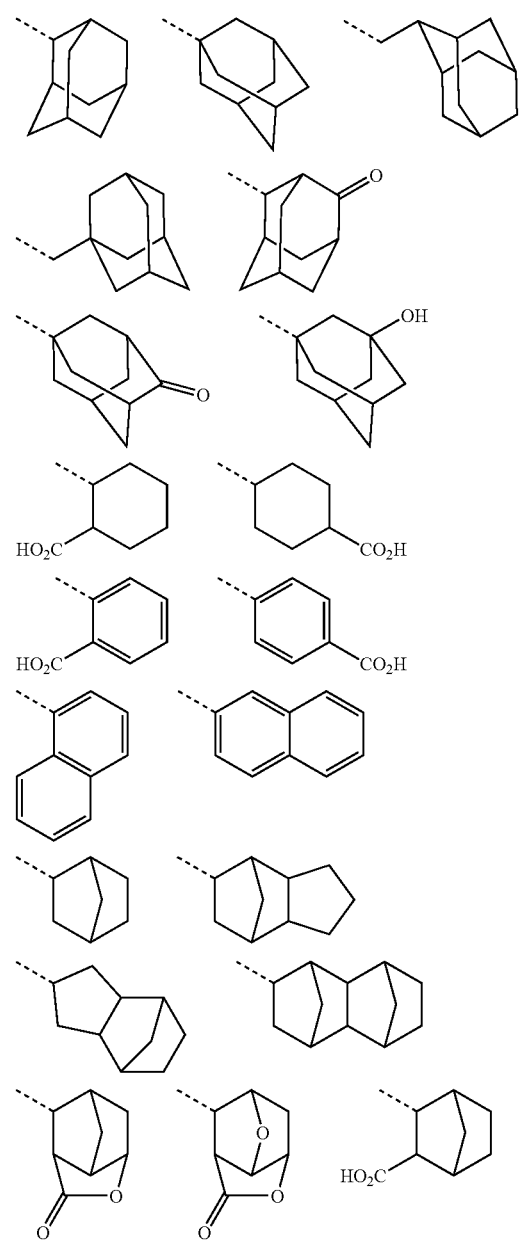

-continued
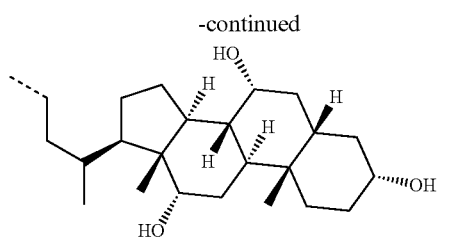
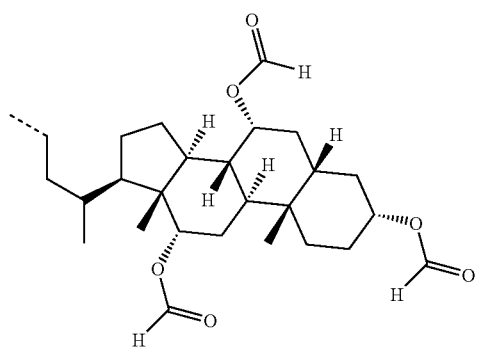
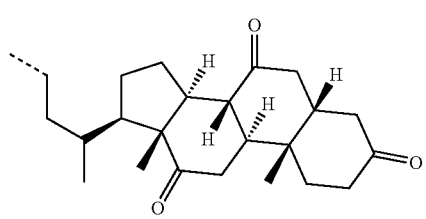
Illustrative examples of acid generators (E)-1 are shown below.
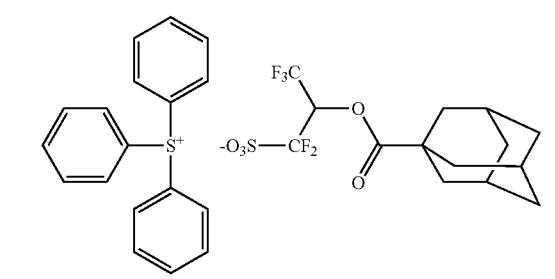
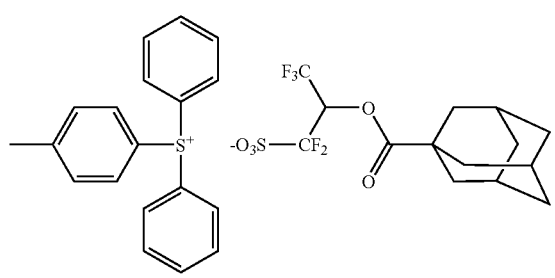
-continued
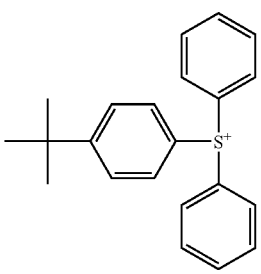
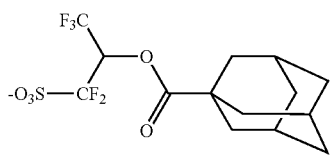
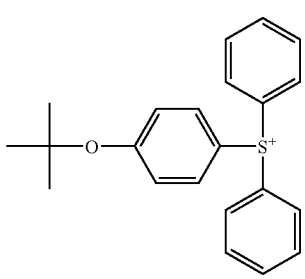
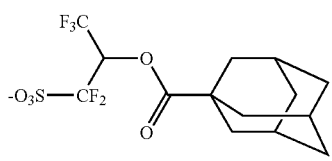
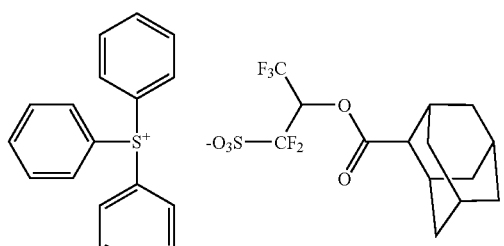
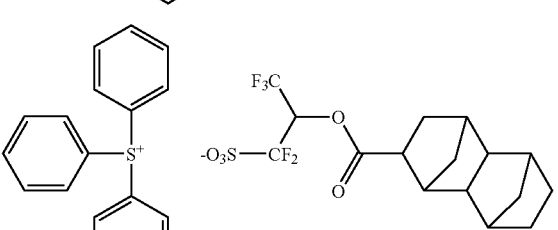
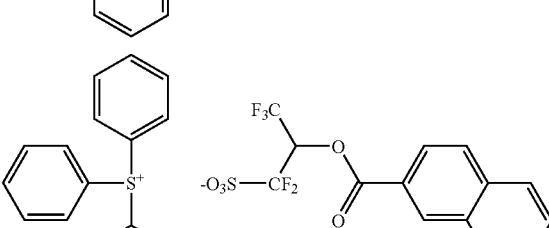
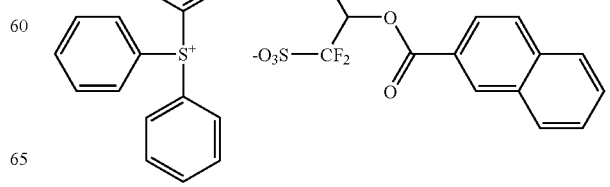

-continued
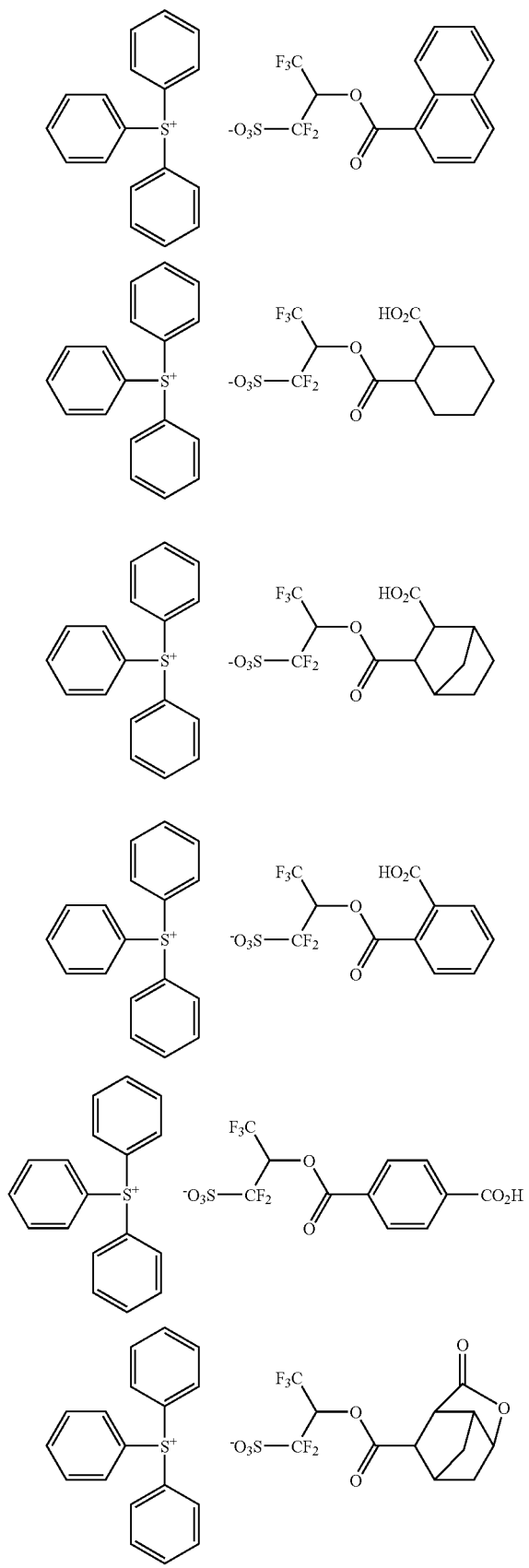
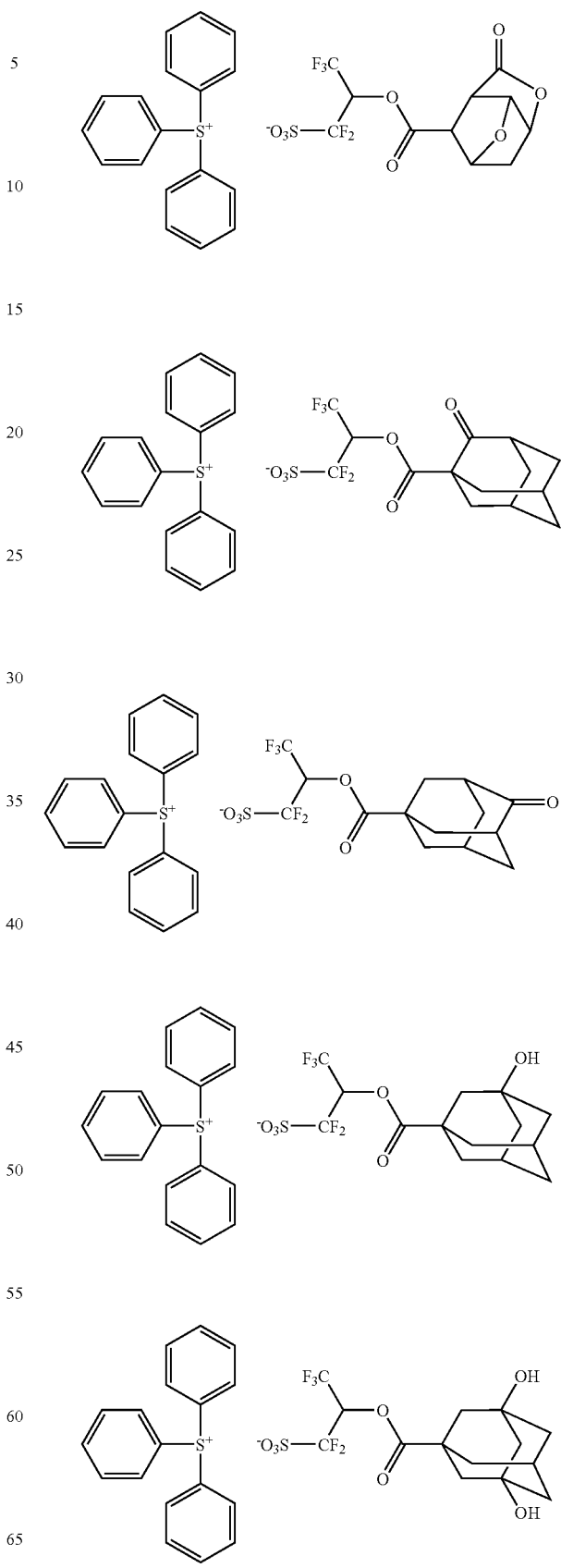

-continued

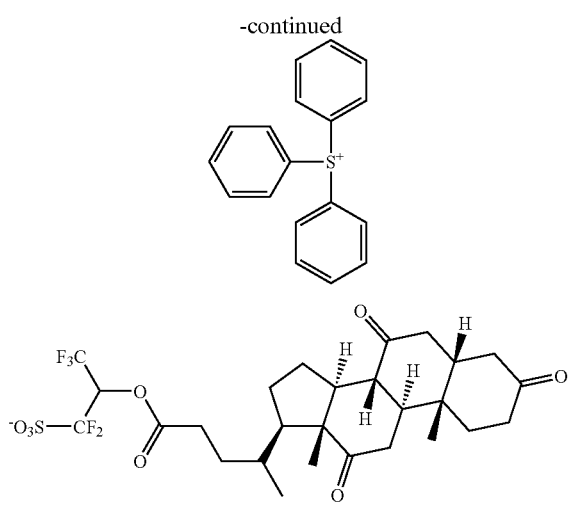

In the chemically amplified resist composition, the auxiliary photoacid generator (E) may be added in any desired amount as long as the objects of the invention are not compromised. An appropriate amount of the photoacid generator (E), when added, is 0.1 to 10 parts, and more preferably 0.1 to 5 parts by weight per 100 parts by weight of the base resin in the composition. Too high a proportion of the photoacid generator (E) may give rise to problems of degraded resolution and foreign matter upon development and resist film peeling. The photoacid generators (E) may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component F

Component (F) is an organic acid derivative and/or a fluorinated alcohol. Illustrative, non-limiting, examples of the organic acid derivatives include phenol, cresol, catechol, resorcinol, pyrogallol, phloroglucin, bis(4-hydroxyphenyl)methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

The fluorinated alcohol is an alcohol which is substituted with fluorine atoms except a-position. Those compounds terminated with 1,1,1,3,3,3-hexafluoro-2-propanol are desirable although the fluorinated alcohols are not limited thereto. Illustrative examples of the desirable fluorinated alcohols are given below.

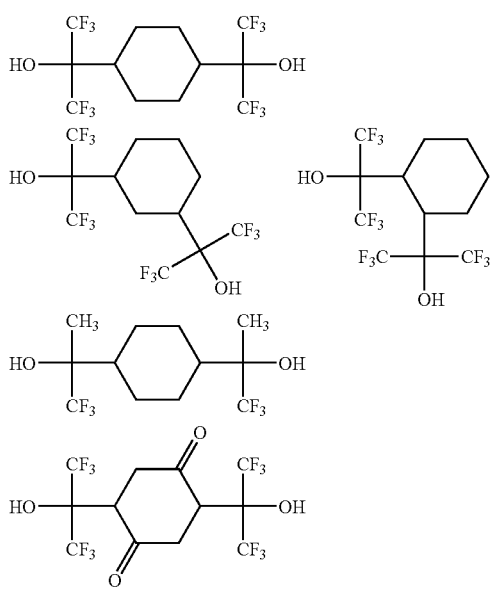

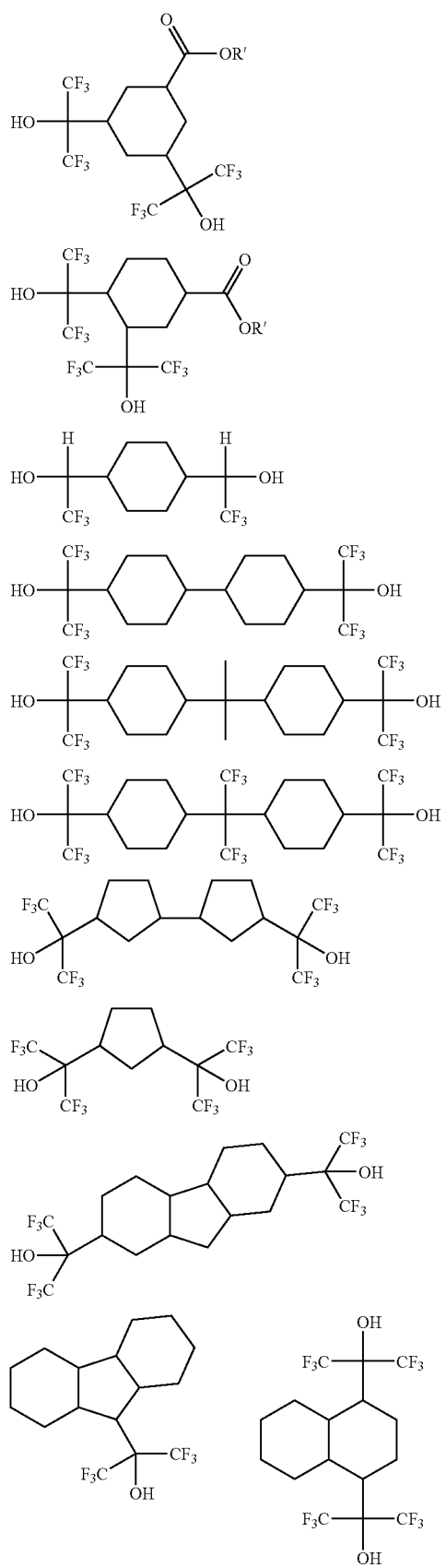
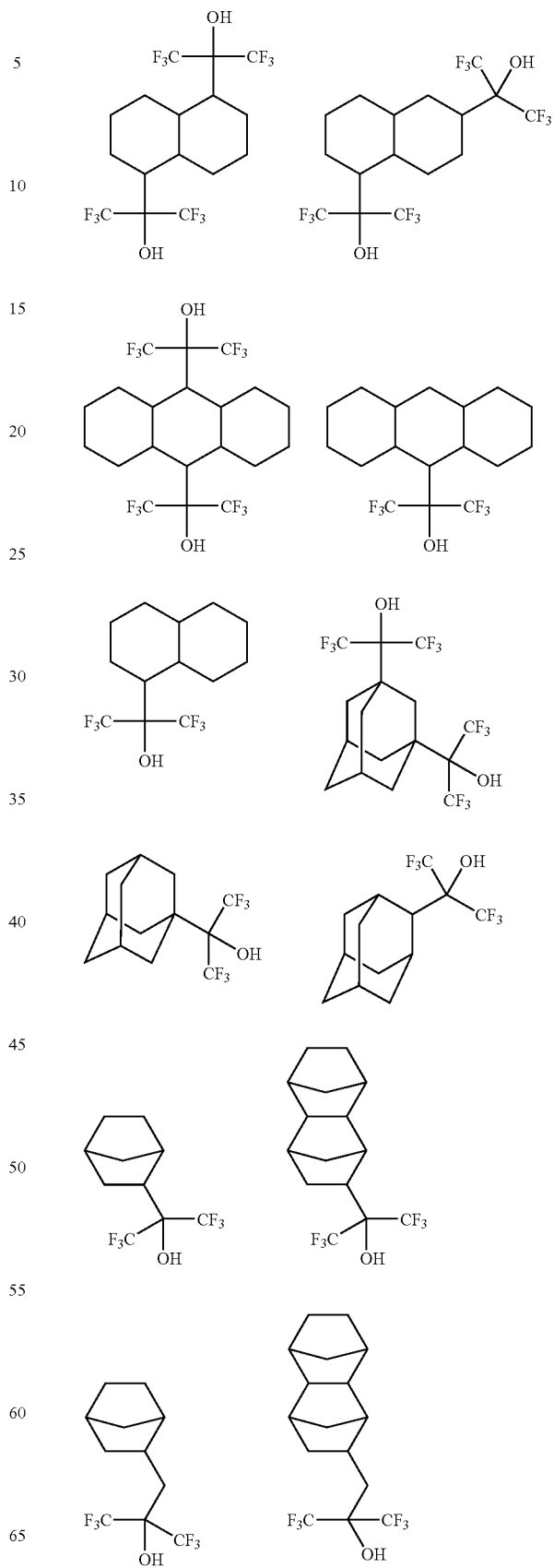

-continued
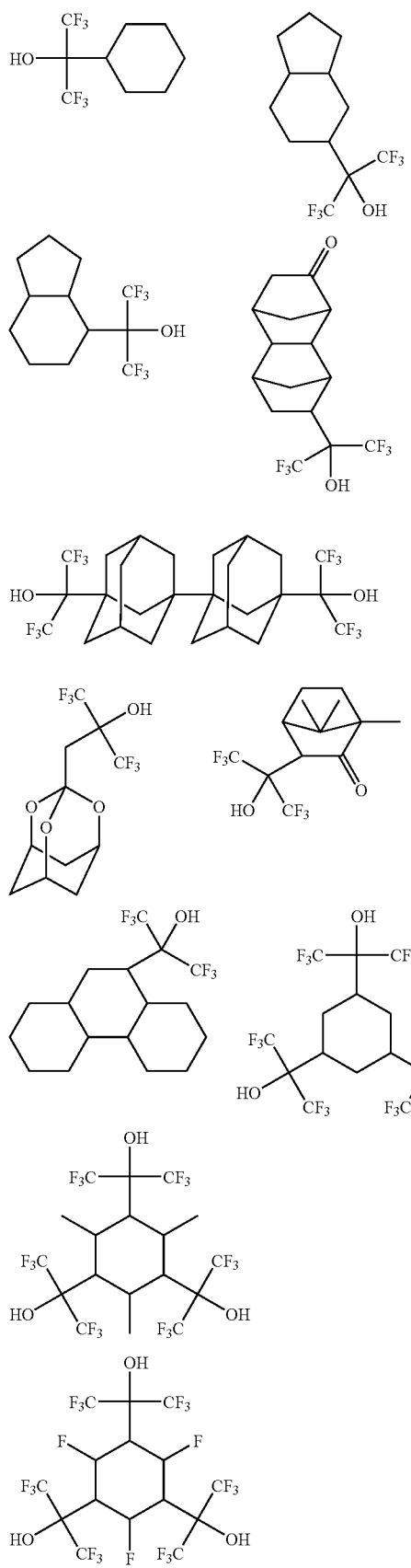
-continued
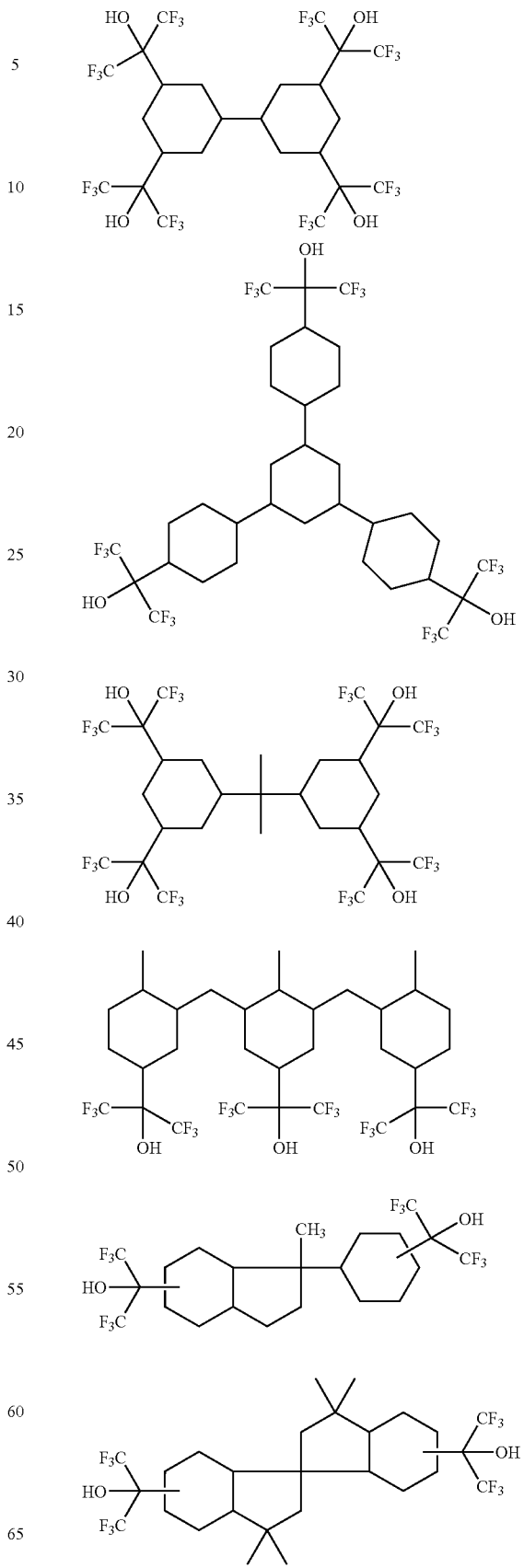

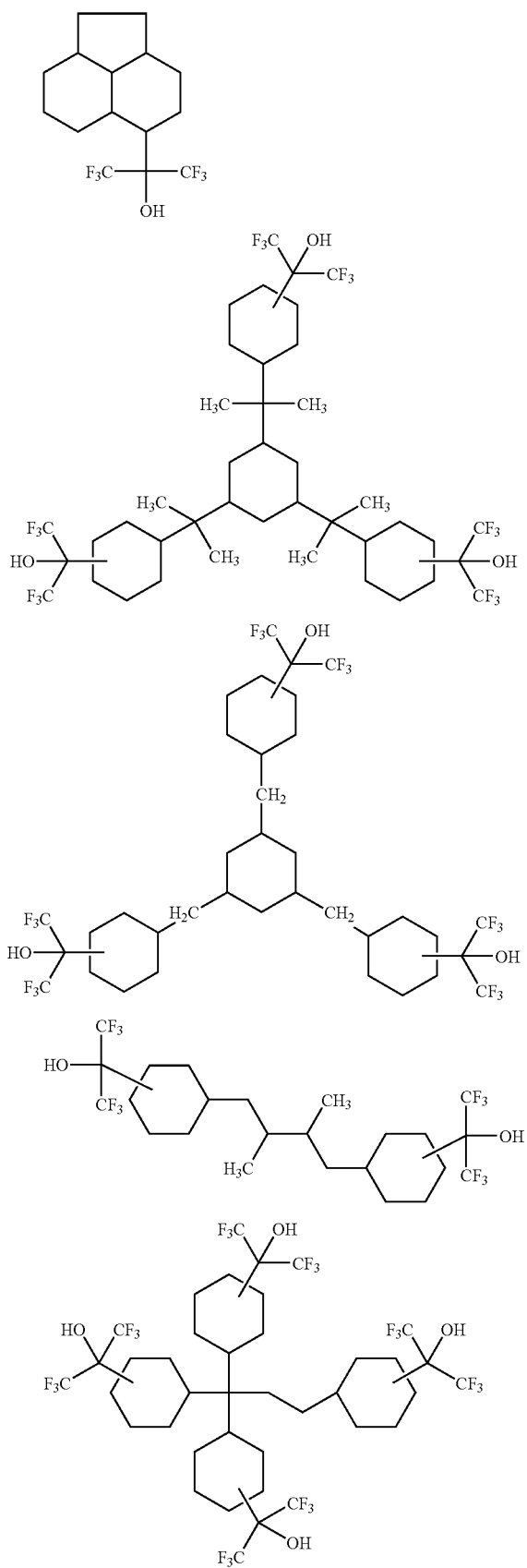

In the chemically amplified resist composition of the invention, the organic acid derivative or fluorinated alcohol is preferably formulated in an amount of up to 5 parts, and especially up to 1 part by weight, per 100 parts by weight of the base resin. More than 5 phr may result in too low a resolution. Depending on the combination of the other components in the resist composition, the organic acid derivative and fluorinated alcohol may be omitted.

Component G

In one preferred embodiment, the resist composition further contains (G) a compound with a weight average molecular weight of up to 3,000 which changes its solubility in an alkaline developer under the action of an acid, that is, a dissolution inhibitor. Typically, a compound obtained by substituting acid labile substituents for some or all hydrogen atoms of hydroxyl groups on a phenol or carboxylic acid derivative having a low molecular weight of up to 2,500 or fluorinated alcohol is added as the dissolution inhibitor.

Examples of the phenol or carboxylic acid derivative having a weight average molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, thymolphthalein, cholic acid, deoxycholic acid, and lithocholic acid. Examples of the fluorinated alcohol include compounds terminated with 1,1,1,3,3,3-hexafluoro-2-propanol as described above. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)

phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis (4-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)valerate, tert-butyl 4,4-bis(4'-(2"-tetrahydrofuranyloxy)phenyl)valerate, tert-butyl 4,4-bis(4l-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1"-ethoxyethoxy)phenyl)valerate, tert-butyl 4,4-bis (4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy) phenyl)methane, 1,1,2-tris(4'-(2"-tetrahydropyranyloxy) phenyl)ethane, 1,1,2-tris(4l-(2"-tetrahydrofuranyloxy) phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'l-ethoxypropyloxy)phenyl)ethane, tert-butyl cholate, tert-butyl deoxycholate, and tert-butyl lithocholate. The compounds described in JP-A 2003-107706 are also useful.

In the resist composition of the invention, an appropriate amount of the dissolution inhibitor (G) is up to 20 parts, and especially up to 15 parts by weight per 100 parts by weight of the base resin. With more than 20 phr of the dissolution inhibitor, the resist composition becomes less heat resistant because of an increased content of monomer components.

Component C'

The base resin used in the negative working resist composition is (C') a base resin which is normally alkali soluble, but becomes substantially alkali insoluble under the action of a crosslinker. It is preferably a precursor resin which will be substituted with acid labile groups to form the base resin (C).

Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methyl-styrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer (to be protected with acid labile groups). Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isobornyl, and cyclohexyl. It is also possible to introduce acid-decomposable substituent groups such as tert-butoxycarbonyl and relatively acid-undecomposable substituent groups such as tert-butyl and tert-butoxycarbonylmethyl.

In the resist composition, the resin (C') is blended in any desired amount, preferably of 65 to 99 parts by weight, especially 65 to 98 parts by weight per 100 parts by weight of the solids (inclusive of that resin).

Component I

Formulated in the negative resist composition is an acid crosslinker (F) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N-tetramethoxymethylurea, and hexamethoxymethylmelamine.

In the chemically amplified resist composition, an appropriate amount of the acid crosslinker (I) is, though not limited thereto, 1 to 20 parts, and especially 5 to 15 parts by weight per 100 parts by weight of the base resin. The crosslinkers may be used alone or in admixture of two or more.

Component H

In the chemically amplified resist composition of the invention, (H) a surfactant for improving coating characteristics may be added as an optional component.

Illustrative, non-limiting, examples of the surfactant (H) include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, $R^{08}$, $R^{30}$, $R^{90}$ and $R^{94}$ (Dai-Nippon Ink & Chemicals, Inc.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1).

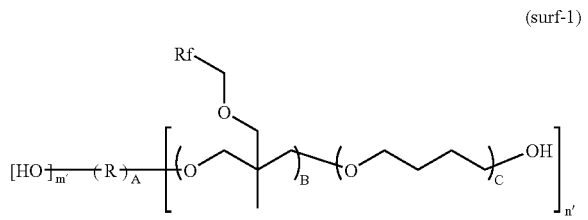

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

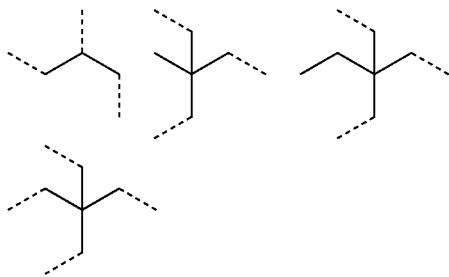

Herein the broken line denotes a valence bond. These formulae are partial structures derived from glycerol, trimethylol ethane,-trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20 and KH-30, and oxetane ring-opened polymers of formula (surf-1) are preferred. These surfactants may be used alone or in admixture.

In the chemically amplified resist composition of the invention, the surfactant is preferably formulated in an amount of up to 2 parts, and especially up to 1 part by weight, per 100 parts by weight of the base resin.

In one embodiment wherein the immersion lithography using water is applied to the resist composition of the invention, particularly in the absence of a resist protective film, the resist composition may have added thereto another surfactant having a propensity to align on the resist surface after spin coating for achieving a function of minimizing water penetration or leaching. The preferred other surfactant is a polymeric surfactant which is insoluble in water, but soluble in alkaline developer, and especially which is water repellent and enhances water slippage. Suitable polymeric surfactants are shown below.

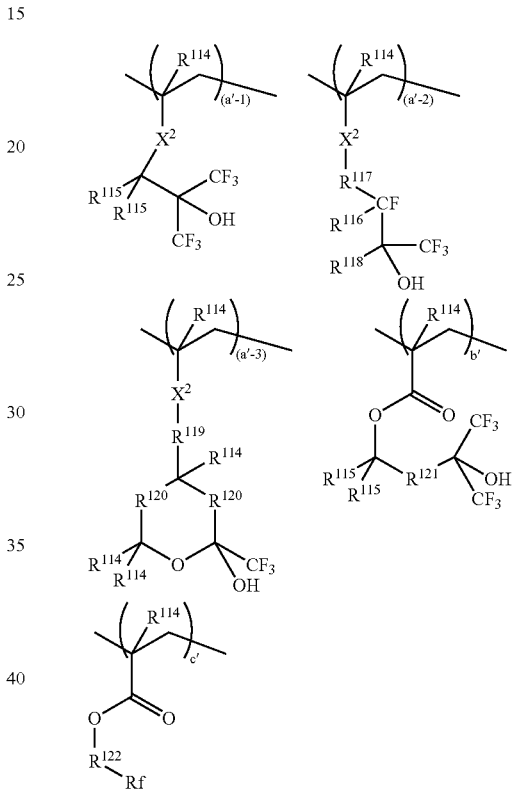

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a non-aromatic ring of 3 to 6 carbon atoms with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range: $0 \leq (a'\text{-}1) < 1$, $0 \leq (a'\text{-}2) < 1$, $0 \leq (a'\text{-}3) < 1$, $0 < (a'\text{-}1) + (a'\text{-}2) + (a'\text{-}3) < 1$, $0 \leq b' < 1$, $0 \leq c' < 1$, and $0 < (a'\text{-}1) + (a'\text{-}2) + (a'\text{-}3) + b' + c' \leq 1$.

In the chemically amplified resist composition of the invention, the polymeric surfactant is preferably formulated in an amount of 0.001 to 20 parts, and more preferably 0.01 to 10 parts by weight, per 100 parts by weight of the base resin. Reference should also be made to JP-A 2007-297590.

In the chemically amplified resist composition of the invention, a UV absorber may be added. Those UV absorbers described in JP-A 11-190904 are useful, but the UV absorber is not limited thereto. Exemplary UV absorbers are diaryl sulfoxide derivatives such as bis(4-hydroxyphenyl) sulfoxide, bis(4-tert-butoxyphenyl) sulfoxide, bis(4-tert-butoxycarbonyloxyphenyl) sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazido group-containing compounds such as complete or partial ester compounds between naphthoquinone-1,2-diazido-5-sulfonic acid chloride and 2,3,4-trihydroxybenzophenone and complete or partial ester compounds between naphthoquinone-1, 2-diazido-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

It is noted that optional components may be added in ordinary amounts as long as the objects of the invention are not compromised.

Any well-known lithography may be used to form a resist pattern from the chemically amplified resist composition of the invention. The composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for 1 to 10 minutes, preferably 80 to 140° C. for 1 to 5 minutes. The resulting resist film is generally 0.1 to 2.0 μm thick. Through a photomask having a desired pattern, the resist film is then exposed to radiation, preferably having an exposure wavelength of up to 300 nm, such as UV, deep-UV, electron beam, EUV, x-ray, excimer laser light, γ-ray and synchrotron radiation. The preferred light source is a beam from an excimer laser, especially KrF excimer laser, deep UV of 245-255 nm wavelength and ArF excimer laser. The exposure dose is preferably in the range of about 1 to 200 mJ/cm², more preferably about 10 to 100 mJ/cm². The film is further baked on a hot plate at 60 to 150° C. for 1 to 5 minutes, preferably 80 to 140° C. for 1 to 3 minutes (post-exposure baking=PEB).

Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray technique. In this way, a desired resist pattern is formed on the substrate. It is appreciated that the resist composition of the invention is best suited for micro-patterning using such actinic radiation as deep UV with a wavelength of 254 to 193 nm, vacuum UV with a wavelength of 157 nm, electron beam, x-ray, excimer laser light, γ-ray and synchrotron radiation. With any of the above-described parameters outside the above-described range, the process may sometimes fail to produce the desired pattern.

In the practice of the invention, the immersion lithography process involving using ArF excimer laser of 193 nm wavelength and feeding a liquid such as water, glycerin or ethylene glycol between the substrate and the projection lens is advantageously applicable.

EXAMPLE

Synthesis Examples, Examples and Comparative Examples are given below for further illustrating the invention, but they are not to be construed as limiting the invention.

Synthesis Example 1-1

Synthesis of triphenylsulfonium chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was aged for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was aged for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 1-2

Synthesis of 4-tert-butylphenyldiphenylsulfonium bromide

The target compound was obtained by following the procedure of Synthesis Example 1-1 aside from using 4-tert-butylbromobenzene instead of the chlorobenzene in Synthesis Example 1-1 and increasing the amount of water for extraction.

Synthesis Example 1-3

Synthesis of 4-tert-butoxyphenyldiphenylsulfonium chloride

The target compound was obtained by following the procedure of Synthesis Example 1-1 aside from using 4-tert-butoxychlorobenzene instead of the chlorobenzene in Synthesis Example 1-1, using dichloromethane containing 5 wt % of triethylamine as the solvent, and increasing the amount of water for extraction.

Synthesis Example 1-4

Synthesis of tris(4-methylphenyl)sulfonium chloride

The target compound was obtained by following the procedure of Synthesis Example 1-1 aside from using bis(4-methylphenyl) sulfoxide instead of the diphenyl sulfoxide and 4-chlorotoluene instead of the chlorobenzene in Synthesis Example 1-1, and increasing the amount of water for extraction.

Synthesis Example 1-5

Synthesis of tris(4-tert-butylphenyl)sulfonium bromide

The target compound was obtained by following the procedure of Synthesis Example 1-1 aside from using bis(4-tert-butylphenyl) sulfoxide instead of the diphenyl sulfoxide and 4-tert-butylbromobenzene instead of the chlorobenzene in Synthesis Example 1-1, and increasing the amount of water for extraction.

Synthesis Example 1-6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling, and a mixture of 35 g of acetic anhydride and 95 g of conc. sulfuric acid was added dropwise at a temperature below 30° C. The resulting solution was aged for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water three times. The washed organic layer was concentrated in vacuum, obtaining a crude target product. The product was used in the subsequent reaction without further purification.

Synthesis Example 1-7

Synthesis of dimethylphenylsulfonium hydrogen sulfate

At room temperature, 6.2 g (0.05 mole) of thioanisol and 6.9 g (0.055 mole) of dimethyl sulfate were stirred for 12 hours. 100 g of water and 50 ml of diethyl ether were added to the reaction solution. The aqueous layer was taken out, which was an aqueous solution of the target compound, dimethylphenylsulfonium hydrogen sulfate.

Synthesis Example 1-8

Synthesis of phenacyltetrahydrothiophenium bromide 88.2 g (0.44 mole) of phenacyl bromide and 39.1 g (0.44 mole) of tetrahydrothiophene were dissolved in 220 g of nitromethane, which was stirred for 4 hours at room temperature. 800 g of water and 400 g of diethyl ether were added to the reaction solution. The aqueous layer was taken out, which was an aqueous solution of the target compound, phenacyltetrahydrothiophenium bromide.

Synthesis Example 1-9

Synthesis of sodium 2-benzoyloxy-1,1,3,3,3-pentafluoro-propane-1-sulfonate 10.0 g of 1,1,3,3,3-pentafluoro-2-propan-2-yl benzoate, which had been synthesized by a conventional technique, was dispersed in 72 g of water, after which 12.0 g of sodium hydrogen sulfite was added. The mixture was allowed to react at 100° C. for 14 hours. It was allowed to cool down and combined with toluene, followed by separatory operation to separate a water layer. A saturated sodium chloride aqueous solution was added to the water layer whereupon white crystals settled out. The crystals were collected by filtration, washed with a small volume of saturated sodium chloride aqueous solution and then dried in vacuum, obtaining the target compound, sodium 2-benzoyloxy-1,1,3,3,3-pantafluoropropane-1-sulfonate. White crystals, 5.85 g (yield 43%).

Synthesis-Example 1-10

Synthesis of triphenylsulfonium 2-benzoyloxy-1,1,3,3,3-pentafluoropropane-1-sulfonate To 50 g of dichloromethane were added an amount (corresponding to 0.011 mole) of the triphenylsulfonium chloride aqueous solution of Synthesis Example 1-1 and 3.6 g (0.01 mole) of sodium 2-benzoyloxy-1,1,3,3,3-pentafluoro-propane-1-sulfonate synthesized in Synthesis Example 1-9, followed by stirring. The organic layer was separated and washed with 50 g of water three times. The organic layer was concentrated and 25 g of diethyl ether was added to the residue for crystallization. The crystals were filtered and dried, obtaining the target compound. White crystals, 4.5 g (yield 75%).

Synthesis Example 1-11

Synthesis of triphenylsulfonium 2-hydroxy-1,1,3,3,3-pentafluoropropane-1-sulfonate (PAG1)

In 72 g of methanol was dissolved 34.4 g of triphenylsulfonium 2-benzoyloxy-1,1,3,3,3-pentafluoropropane-1-sulfonate synthesized in Synthesis Example 1-10. While the solution was stirred under ice cooling, 54.0 g of 5% sodium hydroxide aqueous solution was added dropwise at a temperature below 10° C. It was aged at the temperature for 4 hours. At a temperature below 10° C., 6.8 g of 12N hydrochloric acid was added to quench the reaction. The methanol was distilled off in vacuum, after which 270 g of dichloromethane was added to the residue. The organic layer was washed with 40 g of water three times. The organic layer was concentrated, after which 60 g of diethyl ether was added to the residue for crystallization. The crystals were filtered and dried, obtaining the target compound. White crystals, 24.3 g (yield 85%). The target compound, designated PAG1, had the following structure.

PAG 1

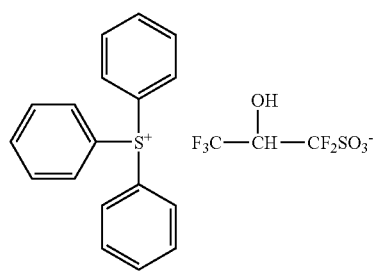

Synthesis Examples 1-12 to 1-18

Target compounds were synthesized as in Synthesis Examples 1-10 and 1-11 except that the sulfonium or iodonium salts prepared in Synthesis Examples 1-2 to 1-8 were used. The resulting onium salts PAG2 to PAG8 are shown below.

PAG 2

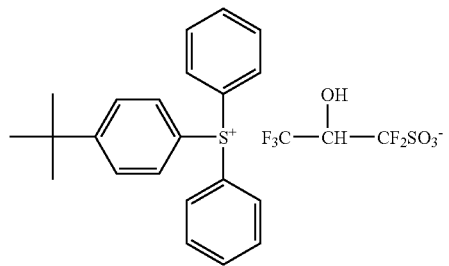

PAG 3

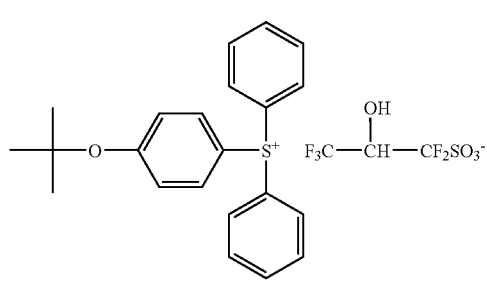

-continued

PAG 4

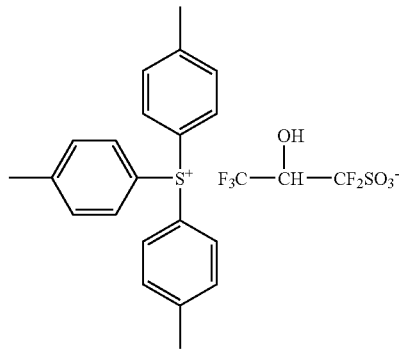

PAG 5

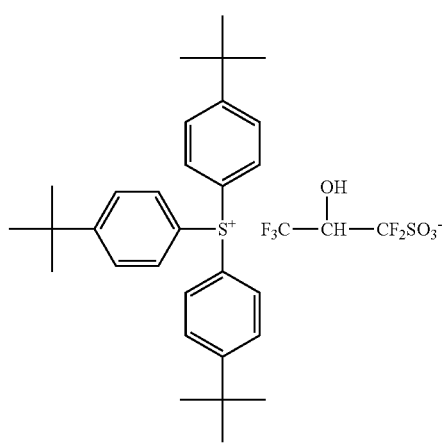

PAG 6

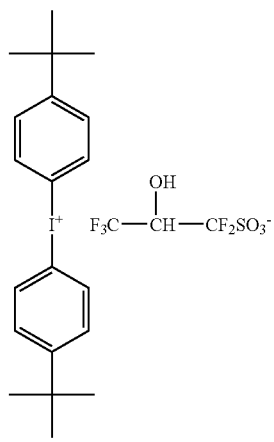

PAG 7

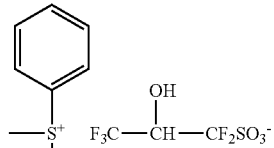

PAG 8

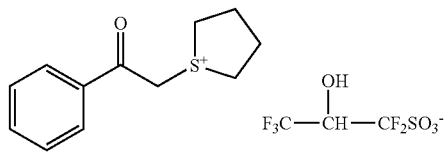

Synthesis Example 1-19

Synthesis of triphenylsulfonium 1-difluorosulfomethyl-2,2,2-trifluoroethyl 3,7,12-trioxocholanoate (PAG-A)

To a mixed suspension of 4.9 g (0.01 mole) of triphenylsulfonium 2-hydroxy-1,1,3,3,3-pentafluoropropane-1-sulfonate of Synthesis Example 1-11 and 4.21 g (0.01 mole) of dehydrocholic acid chloride in 20 g of dichloromethane, a mixture of 1.0 g (0.01 mole) of triethylamine, 0.24 g (0.002 mole) of N,N-dimethylaminopyridine and 5 g of dichloromethane was added dropwise. The reaction mixture was stirred at room temperature for 2 hours. Thereafter, a dilute hydrochloric acid solution prepared from 2 g of 12N hydrochloric acid and 20 g of water was added to the reaction mixture, whereupon the organic layer was separated. The organic layer was then washed with 20 g of water, after which dichloromethane was distilled off in vacuum. 30 g of methyl isobutyl ketone and 20 g of a 0.2% sodium hydroxide aqueous solution were added to the residue, whereupon the organic layer was separated. The organic layer was then washed with 20 g of water, after which methyl isobutyl ketone was distilled off in vacuum. Ether was added to the residue for purification by recrystallization. Filtration and drying gave the target compound. White crystals, 4.0 g (yield 43%). The target compound had the structure shown below.

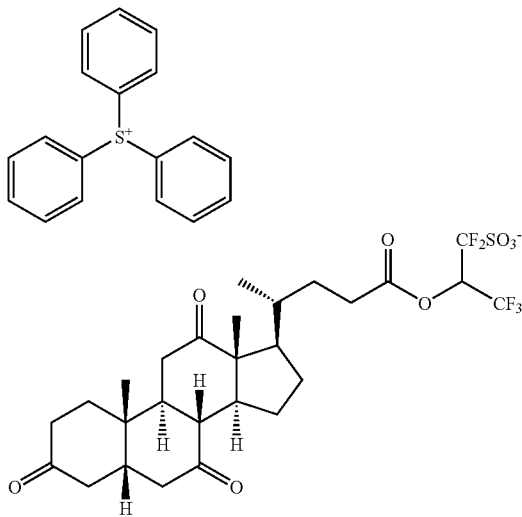

Figure 2:
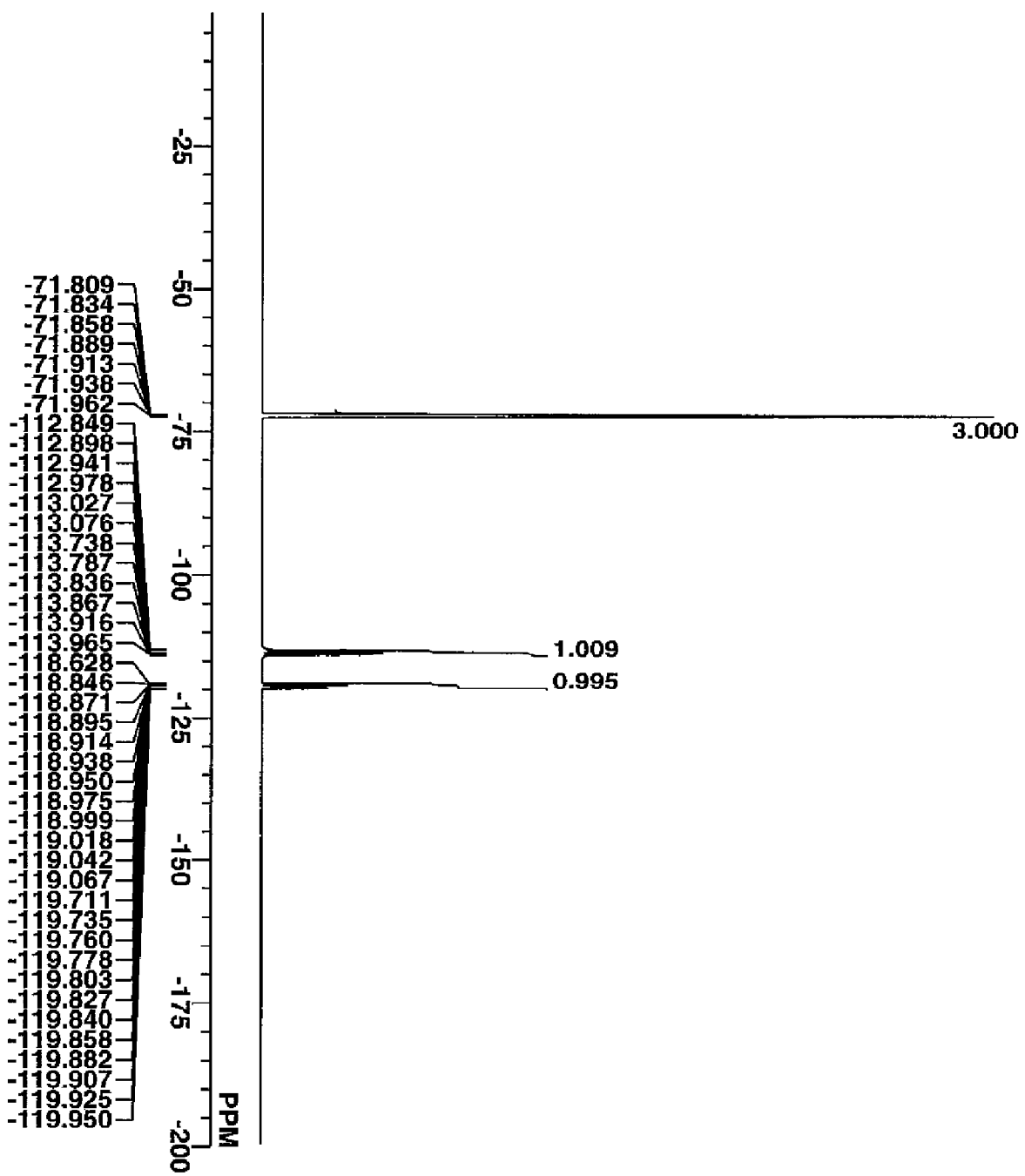
FIG. 2 is a diagram showing the $^{19}$F-NMR/DMSO-$d_6$ spectrum of PAG-A in Synthesis Example 1-19.

The target compound was analyzed by spectroscopy. The data of infrared (IR) absorption spectroscopy and time-of-flight mass spectrometry (TOFMS) are shown below. The NMR spectra, $^1$H-NMR and $^{19}$F-NMR in DMSO-$d_6$ are shown in FIGS. 1 and 2. In $^1$H-NMR analysis, minute amounts of residual solvents (diethyl ether, water) were observed.

IR spectra (KBr, cm$^{-1}$) 3465, 2969, 2875, 1770, 1708, 1477, 1448, 1380, 1332, 1265, 1251, 1216, 1184, 1168, 1120, 1070, 995, 750, 684, 642, 503 TOFMS (MALDI) Positive M$^+$263 (corresponding to $(C_6H_5)_3S^+$) Negative M$^-$613 (corresponding to $CF_3CH(OCO—C_{23}H_{33}O_3)CF_2SO_3^-$)

By repeating the same procedure as in Synthesis Example 1-19 except that one of PAG2 to PAG8 was used instead of PAG1, triphenylsulfonium 2-hydroxy-1,1,3,3,3-pentafluoropropane-1-sulfonate, a series of compounds can be synthesized in which the cation moiety of PAG-A is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium or phenacyltetrahydrothiophenium.

Synthesis Example 1-20

Synthesis of 3,7,12-triformyloxycholanoic acid chloride

By a standard technique using cholic acid and formalin, 3,7,12-triformyloxycholanoic acid was synthesized. It was then chlorinated using oxalyl chloride. The crude product thus obtained was used in the subsequent step of esterification without purification.

Synthesis Example 1-21

Synthesis of triphenylsulfonium 1-difluorosulfomethyl-2,2,2-trifluoroethyl 3,7,12-triformyloxycholanoate (PAG-B)

Synthesis was carried out as in Synthesis Example 1-19 except that 3,7,12-triformyloxycholanoic acid chloride synthesized in Synthesis Example 1-20 was used instead of the dehydrocholic acid chloride in Synthesis Example 1-19 and a dilute hydrochloric acid solution prepared from 0.2 g of 12N hydrochloric acid and 10 g of water was used as the quenching dilute hydrochloric acid. The crude product was purified by reprecipitation from diethyl ether. The oily matter was vacuum evaporated to dryness, yielding the target compound as an amorphous material (8.0 g, yield 83%).

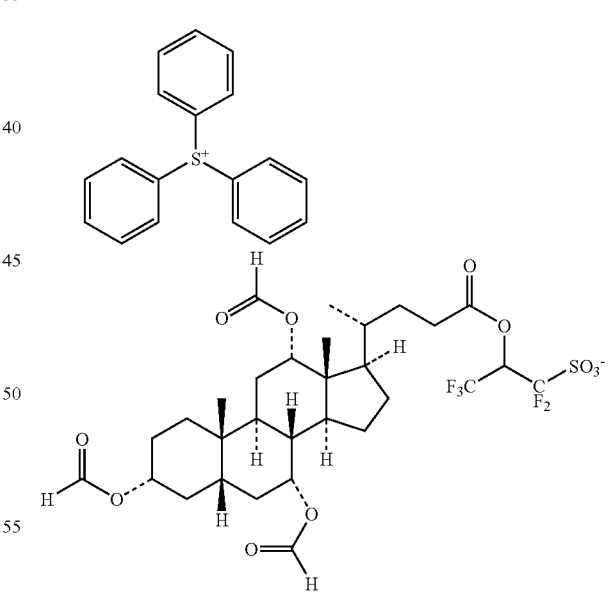

Figure 3:
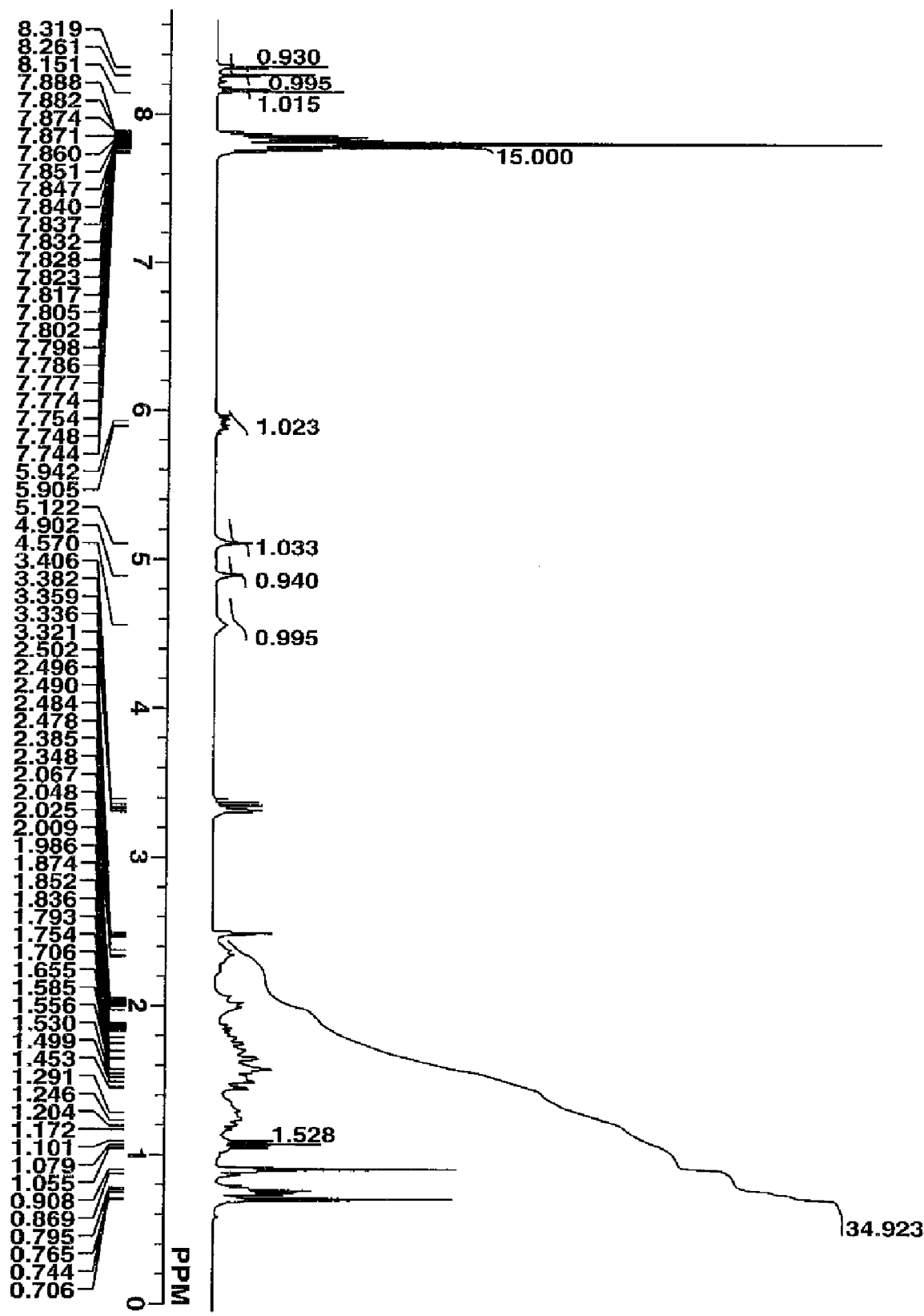
FIG. 3 is a diagram showing the $^1$H-NMR/DMSO-$d_6$ spectrum of PAG-B in Synthesis Example 1-21.
Figure 4:
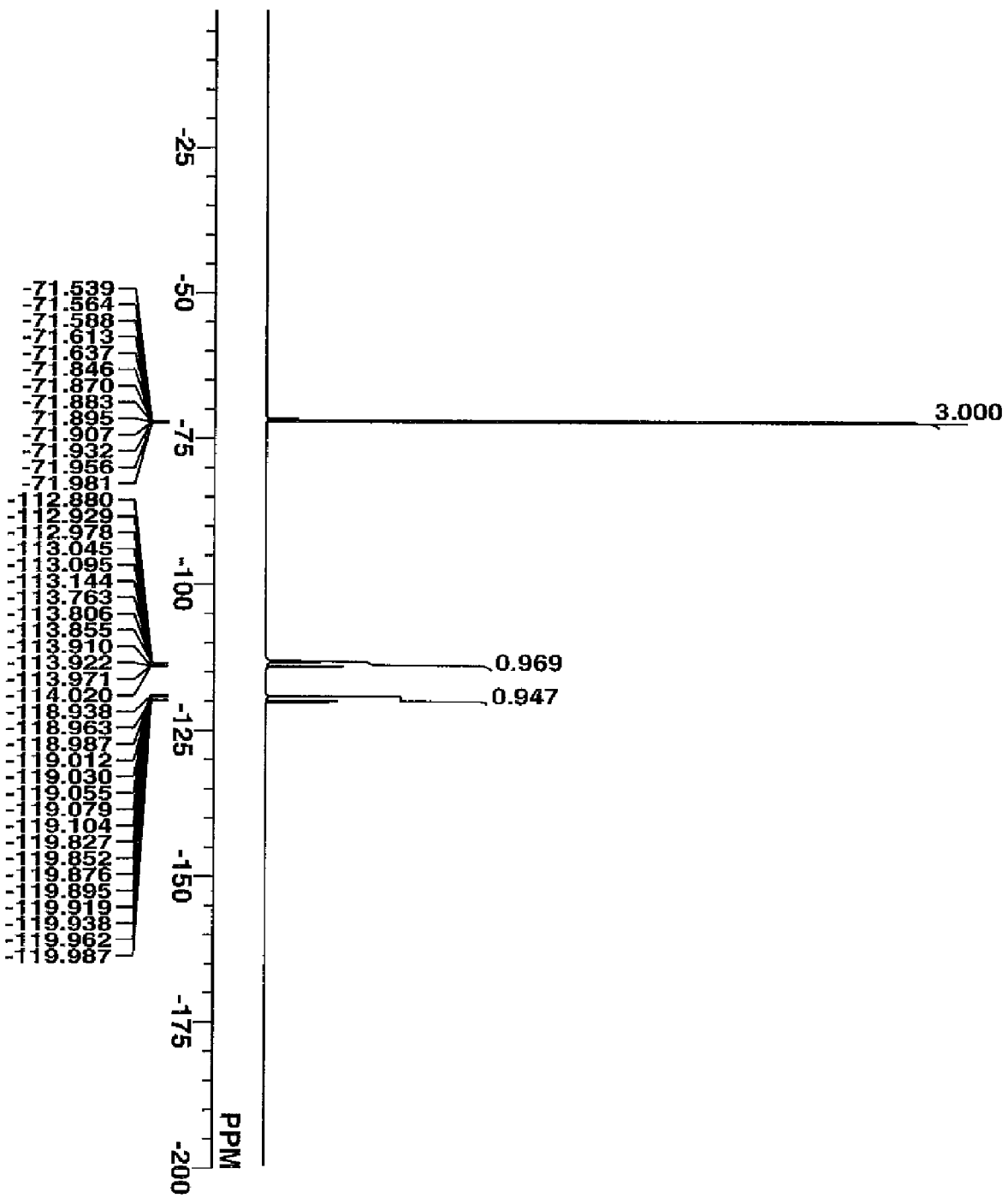
FIG. 4 is a diagram showing the $^{19}$F-NMR/DMSO-$d_6$ spectrum of PAG-B in Synthesis Example 1-21.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 3 and 4. In $^1$H-NMR analysis, minute amounts of residual solvents (diethyl ether, water) were observed.

IR spectra (KBr, cm$^{-1}$) 2942, 2871, 1770, 1716, 1477, 1448, 1373, 1265, 1251, 1184, 1124, 1101, 1070, 995, 750, 684, 642 TOFMS (MALDI) Positive M⁺263 (corresponding to $(C_6H_5)_3S^+$) Negative M⁻703 (corresponding to $CF_3CH(OCO-C_{26}H_{39}O_6)CF_2SO_3^-$)

By repeating the same procedure as in Synthesis Example 1-25 except that one of PAG2 to PAG8 was used instead of PAG1, triphenylsulfonium 2-hydroxy-1,1,3,3,3-pentafluoropropane-1-sulfonate, a series of compounds can be synthesized in which the cation moiety of PAG-B is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium or phenacyltetrahydrothiophenium.

Synthesis Example 1-22

Synthesis of triphenylsulfonium 2-choresteryloxycarbonyl-oxy-1,1,3,3,3-pentafluoropropane-1-sulfonate (PAG-C)

To a mixed solution of 4.9 g (0.01 mole) of triphenylsulfonium 2-hydroxy-1,1,3,3,3-pentafluoropropane-1-sulfonate of Synthesis Example 1-11 and 4.5 g (0.01 mole) of choresteryl chloroformate in 20 g of dichloromethane, a mixture of 1.0 g (0.01 mole) of triethylamine, 0.24 g (0.002 mole) of N,N-dimethylaminopyridine and 5 g of dichloromethane was added dropwise. The reaction mixture was stirred at room temperature for 2 hours. Thereafter, a dilute hydrochloric acid solution prepared from 2 g of 12N hydrochloric acid and 20 g of water was added to the reaction mixture, whereupon the organic layer was separated. The organic layer was then washed with 20 g of water, after which dichloromethane was distilled off in vacuum. 30 g of methyl isobutyl ketone was added to the residue. The solution was washed with 20 g of water, after which methyl isobutyl ketone was distilled off in vacuum. The residue was washed with hexane and dried, obtaining the target compound. White crystals, 7.9 g (yield 87%). The target compound had the structure shown below.

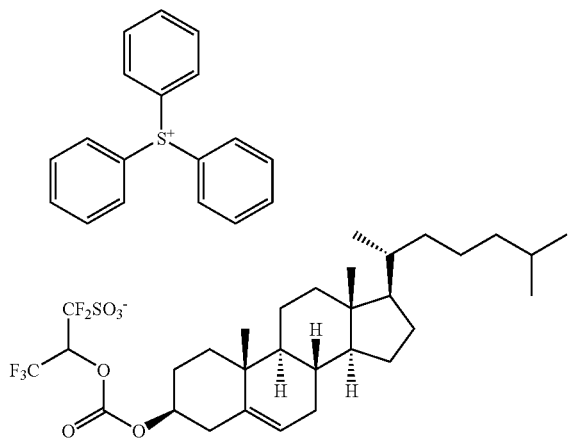

Figure 5:
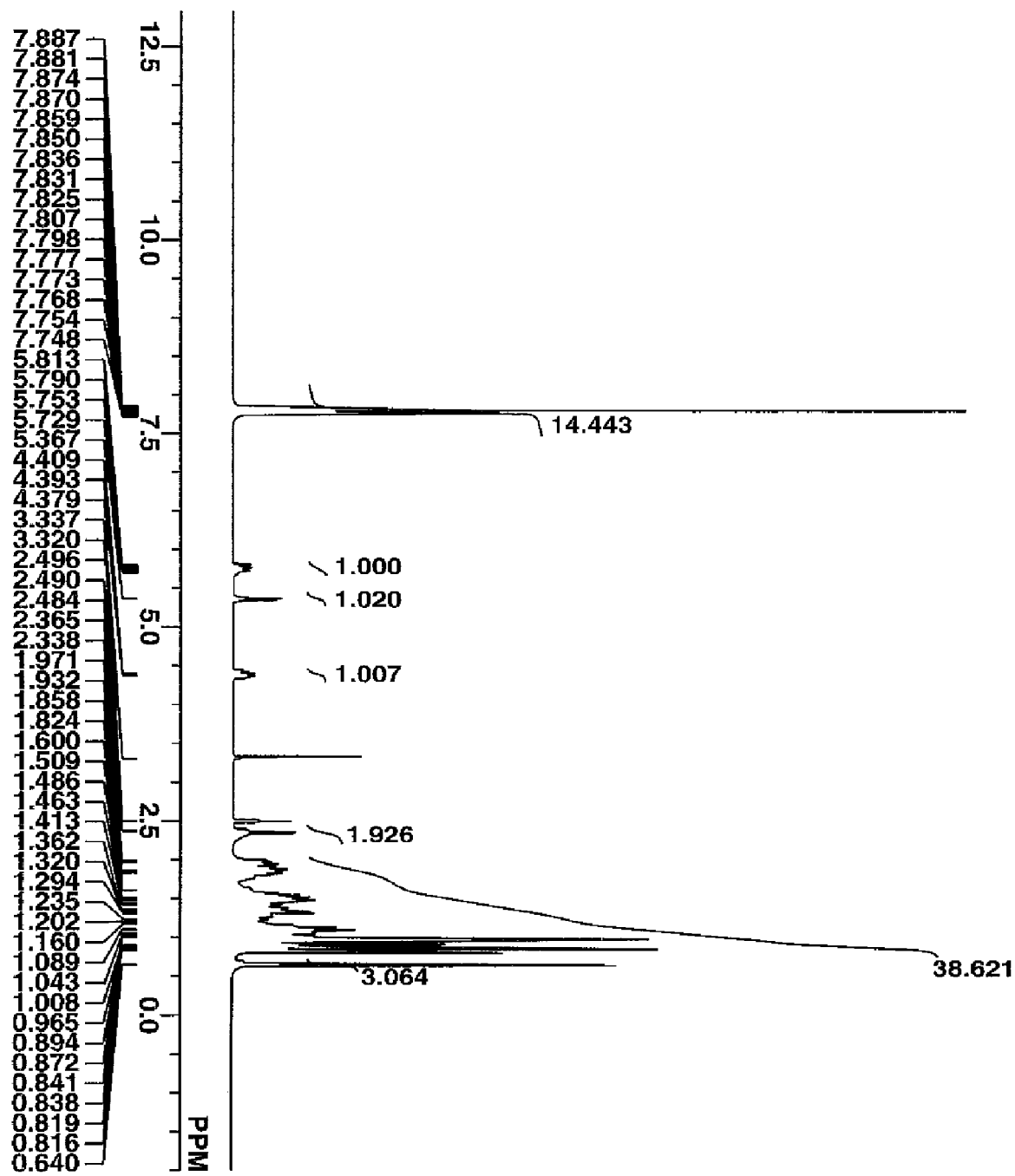
FIG. 5 is a diagram showing the $^1$H-NMR/DMSO-$d_6$ spectrum of PAG-C in Synthesis Example 1-22.
Figure 6:
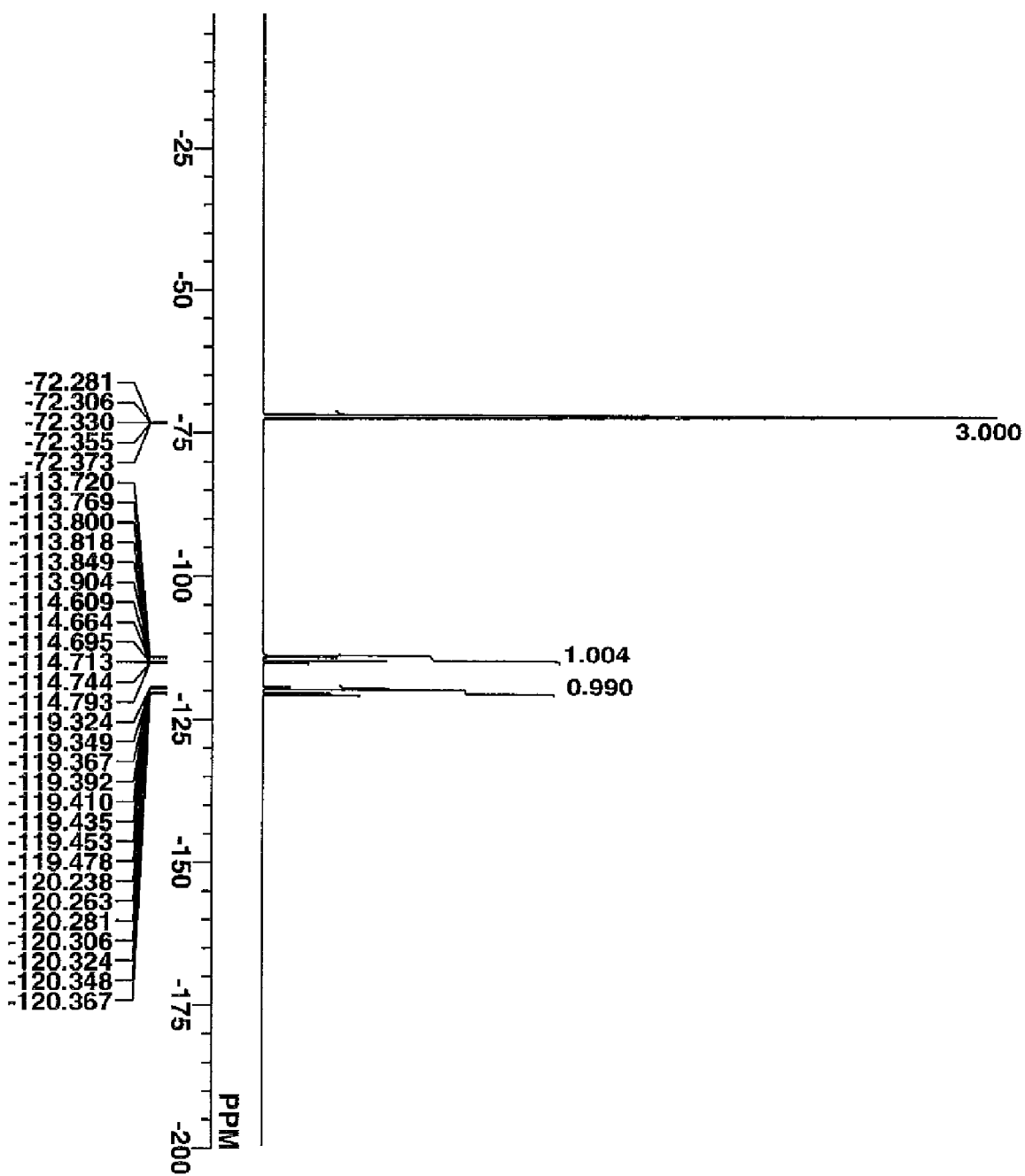
FIG. 6 is a diagram showing the $^{19}$F-NMR/DMSO-$d_6$ spectrum of PAG-C in Synthesis Example 1-22.

The target compound was analyzed by spectroscopy. The data of IR spectroscopy and TOFMS are shown below. The NMR spectra, ¹H-NMR and ¹⁹F-NMR in DMSO-d₆ are shown in FIGS. 5 and 6. In ¹H-NMR analysis, minute amounts of residual solvents (diethyl ether, water) were observed.

IR spectra (KBr, cm⁻¹) 3419, 2950, 2867, 2852, 1768, 1477, 1448, 1373, 1332, 1249, 1187, 1166, 1132, 1072, 993, 970, 944, 748, 684, 640, 551, 522, 501 TOFMS (MALDI) Positive M⁺263 (corresponding to $(C_6H_5)_3S^+$) Negative M⁻641 (corresponding to $CF_3CH(OCOO-C_{27}H_{45})CF_2SO_3^-$)

By repeating the same procedure as in Synthesis Example 1-22 except that one of PAG2 to PAG8 was used instead of PAG1, triphenylsulfonium 2-hydroxy-1,1,3,3,3-pentafluoropropane-1-sulfonate, a series of compounds can be synthesized in which the cation moiety of PAG-C is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium or phenacyltetrahydrothiophenium.

Synthesis Example 1-23

Synthesis of triphenylsulfonium 2-{4-[4-(10,13-dimethyl-3,7,12-trioxo-hexadecahydro-cyclopenta[a]phenanthren-17-yl)-pentanoyloxy]-acetoxy}-1,1,3,3,3-pentafluoropropane-1-sulfonate (PAG-F)

Synthesis Example 1-23-1

Synthesis of triphenylsulfonium 2-(2-chloroacetoxy)-1,1,3,3,3-pentafluoropropane-1-sulfonate (PAG intermediate 1)

To a mixed solution of 148 g (0.30 mole) of triphenylsulfonium 2-hydroxy-1,1,3,3,3-pentafluoropropane-1-sulfonate of Synthesis Example 1-11 and 37.3 g (0.33 mole) of chloroacetyl chloride in 600 g of acetonitrile, 28.5 g (0.36 mole) of pyridine was added dropwise. The solution was stirred for 3 hours at room temperature. The reaction solution was then concentrated, to which 300 g of a 5% dilute hydrochloric acid solution and 600 g of dichloromethane were added, whereupon the organic layer was separated. The organic layer was washed with 300 g of water, after which dichloromethane was distilled off in vacuum. To the residue was added 600 g of methyl isobutyl ketone. This was washed three times with 300 g of water, 300 g of dilute ammonia water, and 300 g of water, after which methyl isobutyl ketone was distilled off in vacuum. Ether was added to the residue for purification by recrystallization. Filtration and drying gave the target compound. White crystals, 158 g (yield 92%). The compound had the structure shown below.

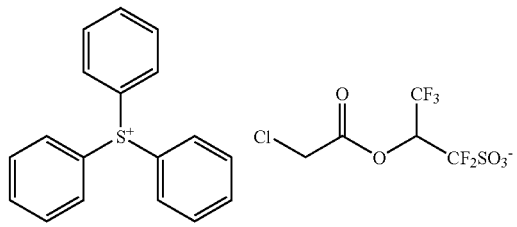

Figure 11:
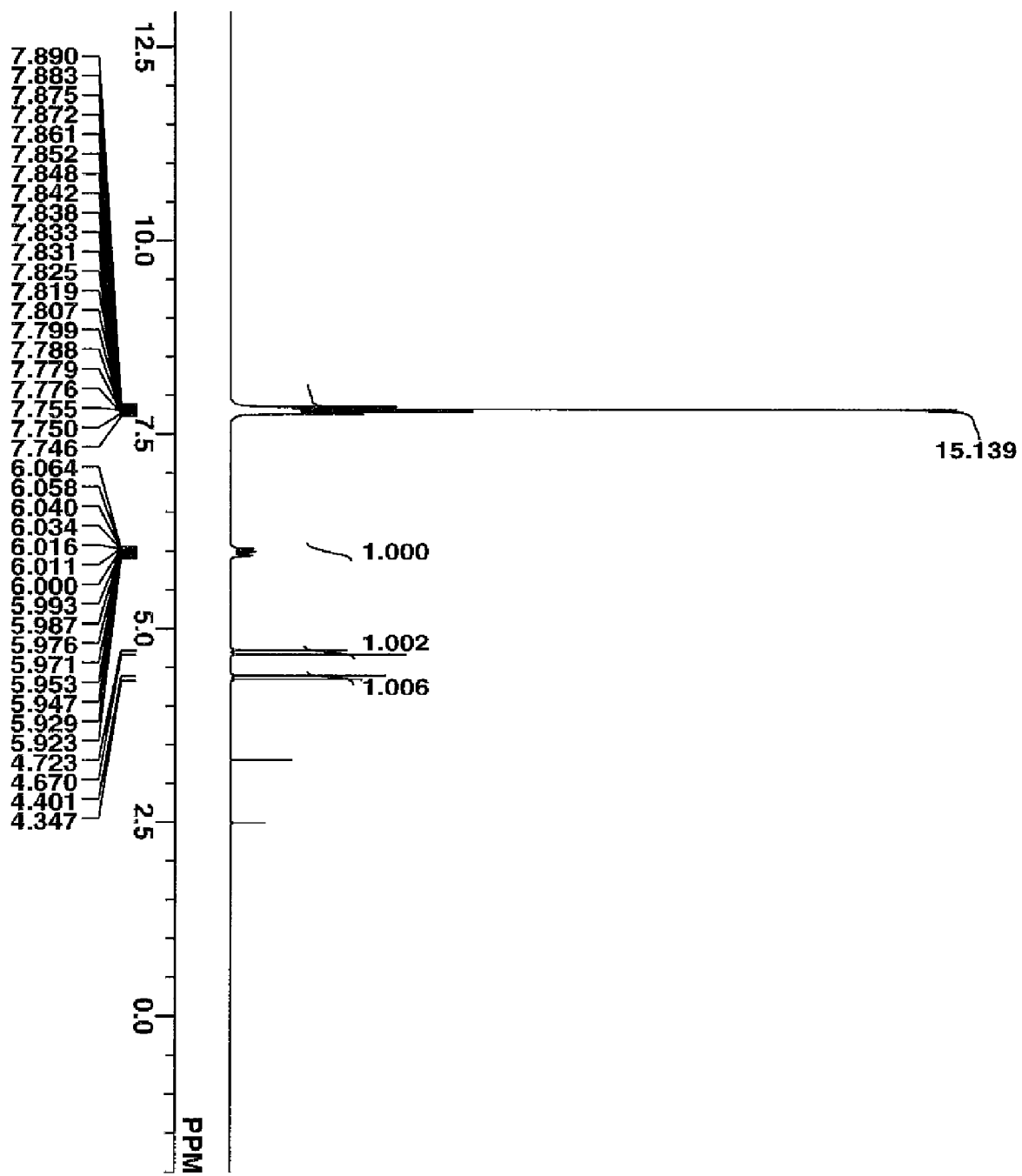
FIG. 11 is a diagram showing the $^1$H-NMR/DMSO-$d_6$ spectrum of PAG intermediate 1 in Synthesis Example 1-23-1.
Figure 12:
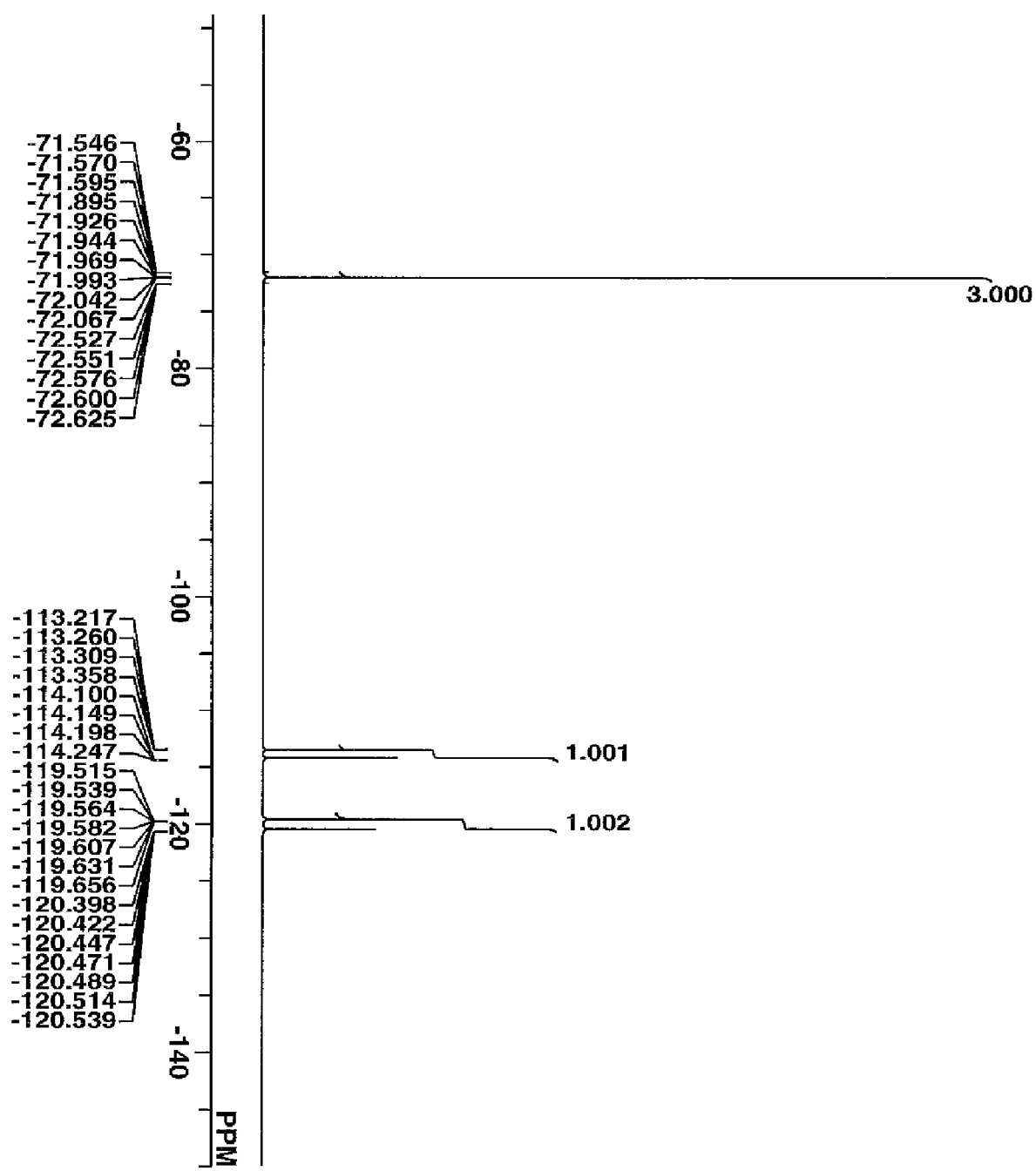
FIG. 12 is a diagram showing the $^{19}$F-NMR/DMSO-d, spectrum of PAG intermediate 1 in Synthesis Example 1-23-1.

The target compound was analyzed by spectroscopy. The data of IR spectroscopy and TOFMS are shown below. The NMR spectra, ¹H-NMR and ¹⁹F-NMR in DMSO-d₆ are shown in FIGS. 11 and 12. In ¹H-NMR analysis, a minute amount of water was observed.

IR spectra (KBr, cm⁻¹) 1781, 1479, 1448, 1407, 1371, 1263. 1249, 1216, 1197, 1143, 1124, 1068, 995, 943, 750, 682, 642, 501 TOFMS (MALDI) Positive M⁺263 (corresponding to $(C_6H_5)_3S^+$) Negative M⁻305 (corresponding to $CF_3CH(OCO-CH_2Cl)CF_2SO_3^-$)

Synthesis Example 1-23-2

Synthesis of triphenylsulfonium 2-{4-[4-(10,13-dimethyl-3,7,12-trioxo-hexadecahydro-cyclopenta[a]phenanthren-17-yl)-pentanoyloxy]-acetoxy}-1,1,3,3,3-pentafluoropropane-1-sulfonate (PAG-F)

To 35 g of dimethylformamide were added 5.69 g (0.01 mole) of triphenylsulfonium 2-(2-chloroacetoxy)-1,1,3,3,3-pentafluoropropane-1-sulfonate obtained in Synthesis Example 1-23-1, 4.67 g (0.01 mole) of sodium dehydrocholate, and 0.30 g (0.002 mole) of sodium iodide. This was heated and stirred at 90° C. for 15 hours. The reaction solution was allowed to cool down to room temperature, after which 50 g of water and 100 g of dichloromethane were added. The organic layer was taken out and washed with 75 g of water, after which dichloromethane was distilled off in vacuum. To the residue was added 60 g of methyl isobutyl ketone. This was washed three times with 50 g of water, 50 g of a 0.1% sodium hydroxide aqueous solution, and 50 g of water, after which methyl isobutyl ketone was distilled off in vacuum. The residue was purified by silica gel chromatography and recrystallized by diisopropyl ether, yielding the target compound, triphenylsulfonium 2-{4-[4-(10,13-dimethyl-3,7,12-trioxo-hexadecahydro-cyclopenta[a]phenanthren-17-yl)-pentanoyloxy]-acetoxy}-1,1,3,3,3-pentafluoropropane-1-sulfonate. White crystals, 2.3 g (yield 24%). The compound had the structure shown below.

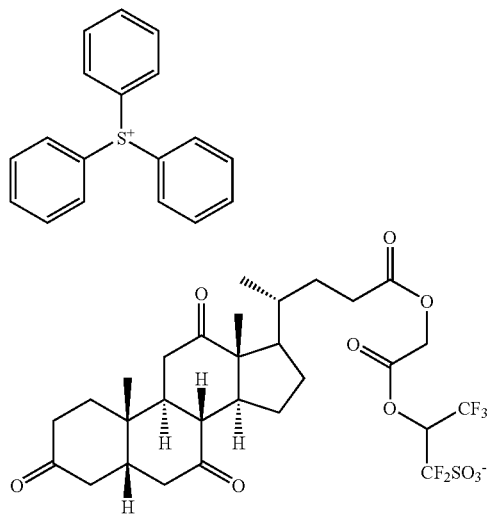

Figure 13:
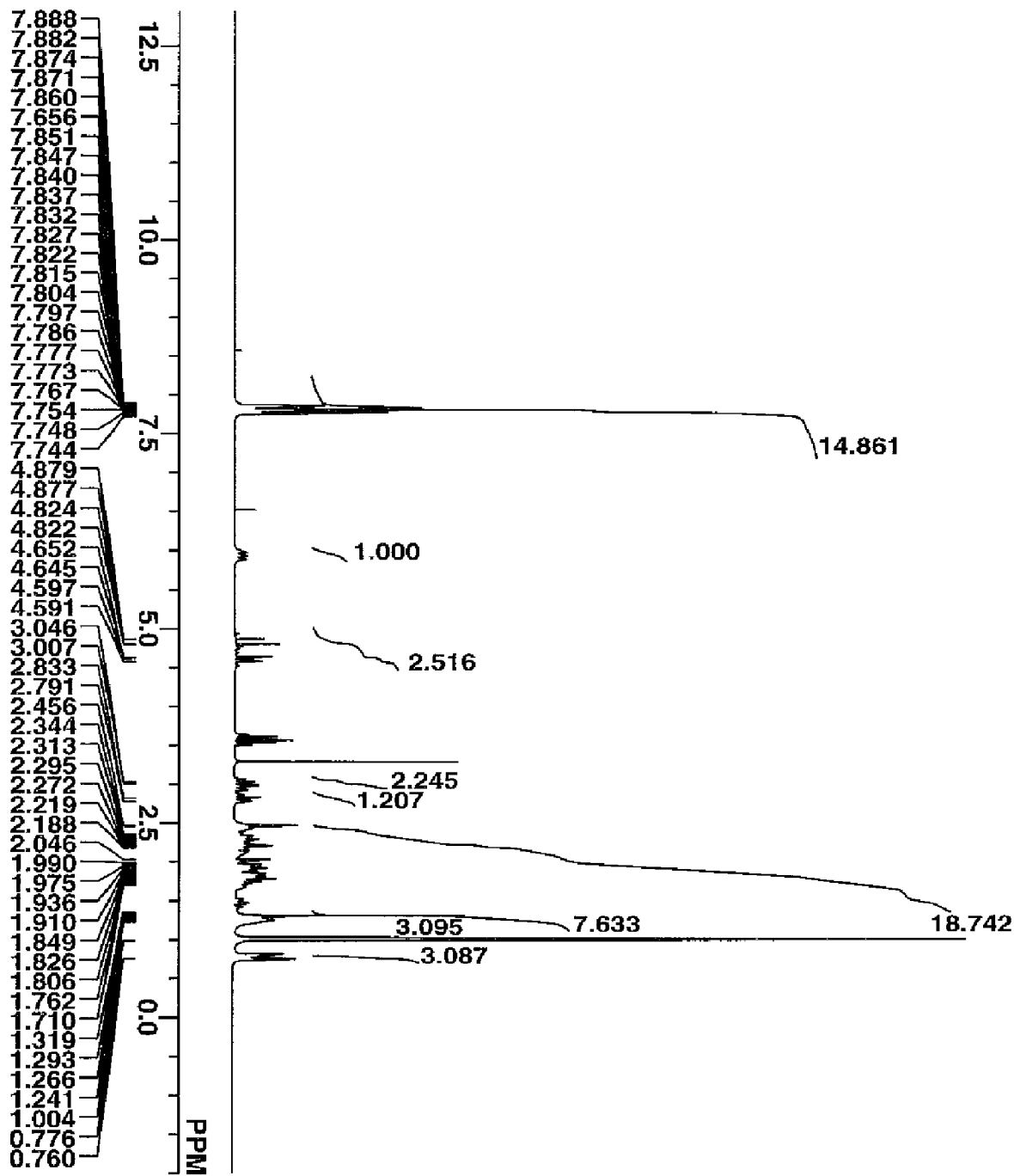
FIG. 13 is a diagram showing the $^1$H-NMR/DMSO-$d_6$ spectrum of PAG-F in Synthesis Example 1-23-2.
Figure 14:
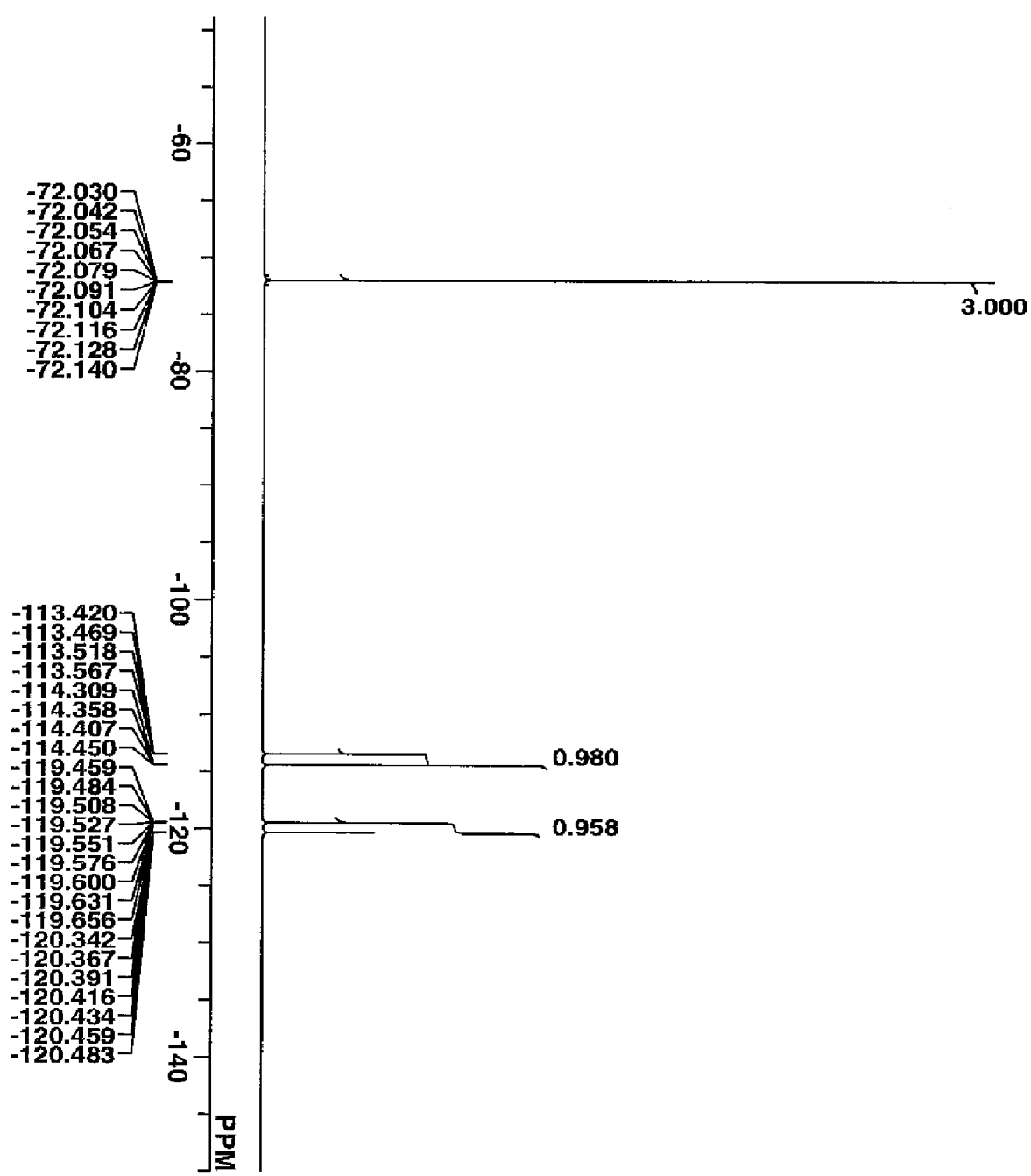
FIG. 14 is a diagram showing the $^{19}$F-NMR/DMSO-$d_6$ spectrum of PAG-F in Synthesis Example 1-23-2.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 13 and 14. In $^1$H-NMR analysis, minute amounts of residual solvents (diisopropyl ether, water) was observed.

IR spectra (KBr, cm$^{-1}$) 3434, 2971, 2875, 1789, 1749, 1706, 1477, 1448, 1382, 1324, 1251, 1216, 1186, 1168, 1143, 1108, 1072, 997, 750, 684. 642, 503 TOFMS (MALDI) Positive M$^+$263 (corresponding to (C$_6$H$_5$)$_3$S$^+$) Negative M$^-$671 (corresponding to CF$_3$CH(OCO—C$_{25}$H$_{35}$O)CF$_2$SO$_3^-$)

By repeating the same procedure as in Synthesis Example 1-23 except that one of PAG2 to PAG8 was used instead of PAG1, triphenylsulfonium 2-hydroxy-1,1,3,3,3-pentafluoropropane-1-sulfonate, a series of compounds can be synthesized in which the cation moiety of PAG-F is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium or phenacyltetrahydrothiophenium.

Synthesis Example 1-24

Synthesis of triphenylsulfonium 2-{4-[4-(10,13-dimethyl-3,7,12-trioxo-hexadecahydro-cyclopenta[a]phenanthren-17-yl)-pentanoyloxy]-butyryloxy}-1,1,3,3,3-pentafluoro-propane-1-sulfonate (PAG-G)

Synthesis Example 1-24-1

Synthesis of triphenylsulfonium 2-(4-chlorobutyryloxy)-1,1,3,3,3-pentafluoropropane-1-sulfonate (PAG intermediate 2)

To a mixed solution of 7.39 g (0.015 mole) of triphenylsulfonium 2-hydroxy-1,1,3,3,3-pentafluoropropane-1-sulfonate and 2.33 g (0.017 mole) of chlorobutyric acid chloride in 37 g of acetonitrile, 1.42 g (0.018 mole) of pyridine was added dropwise. The solution was stirred for 3 hours at room temperature. Then 18 g of a 5% dilute hydrochloric acid solution was added thereto, whereupon acetonitrile was distilled off in vacuum. Thereafter, 40 g of dichloromethane was added, whereupon the organic layer was separated. The organic layer was washed with 30 g of water, after which dichloromethane was distilled off in vacuum. To the residue was added 40 g of methyl isobutyl ketone. This was washed three times with 30 g of water, 30 g of dilute ammonia water, and 30 g of water, after which methyl isobutyl ketone was distilled off in vacuum. Ether was added to the residue. Decantation and vacuum drying gave the target compound. Brown oil, 7.94 g (yield 87%). The compound had the structure shown below.

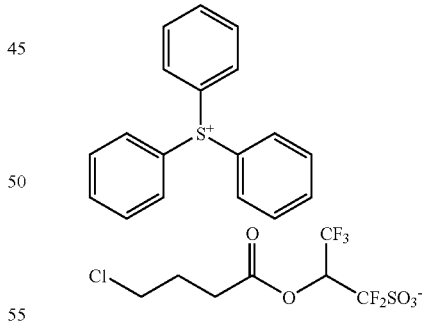

Figure 15:
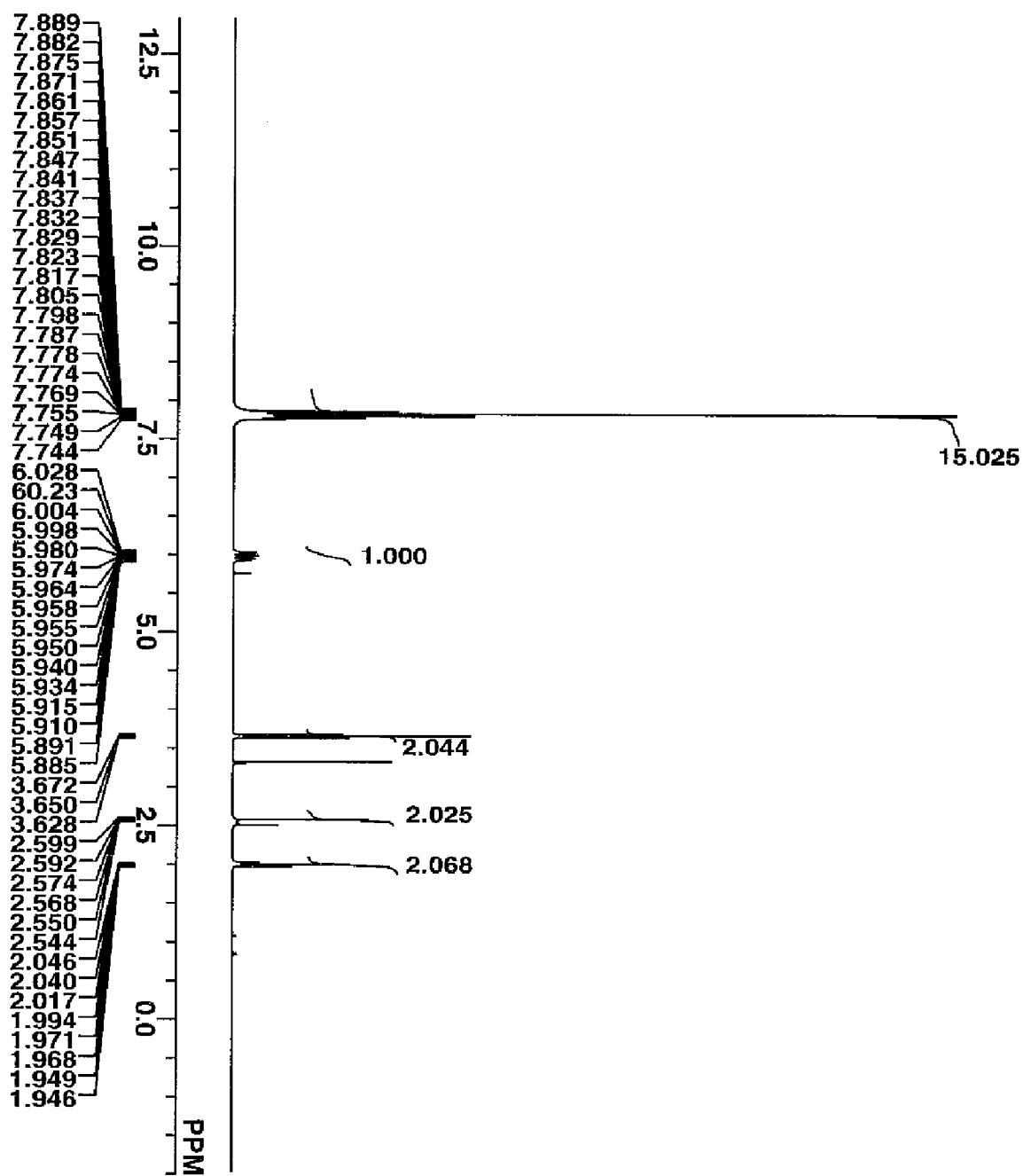
FIG. 15 is a diagram showing the $^1$H-NMR/DMSO-$d_6$ spectrum of PAG intermediate 2 in Synthesis Example 1-24-1.
Figure 16:
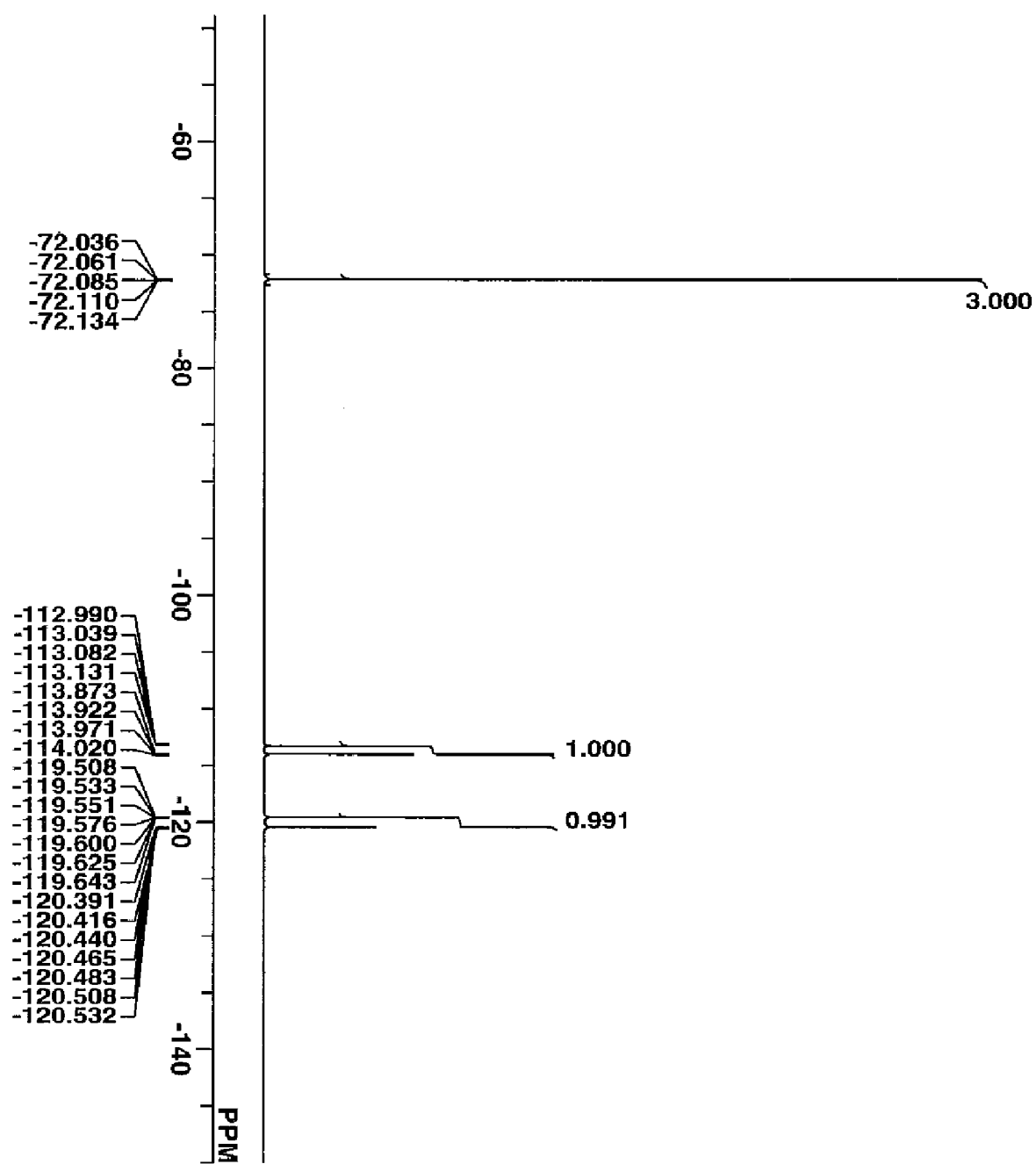
FIG. 16 is a diagram showing the $^{19}$F-NMR/DMSO-$d_6$ spectrum of PAG intermediate 2 in Synthesis Example 1-24-1.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 15 and 16. In $^1$H-NMR analysis, a minute amount of water was observed.

IR spectra (KBr, cm$^{-1}$) 3446, 1772, 1477, 1448, 1373, 1326, 1253, 1216, 1186, 1128, 1072, 995, 750, 684, 642, 503 TOFMS (MALDI) Positive M$^+$263 (corresponding to (C$_6$H$_5$)$_3$S$^+$) Negative M$^-$333 (corresponding to CF$_3$CH(OCO—C$_3$H$_6$Cl)CF$_2$SO$_3^-$)

Synthesis Example 1-24-2

Synthesis of triphenylsulfonium 2-{4-[4-(10,13-dimethyl-3,7,12-trioxo-hexadecahydro-cyclopenta[a]phenanthren-17-yl)-pentanoyloxy]-butyryloxy}-1,1,3,3,3-pentafluoro-propane-1-sulfonate (PAG-G)

To 48 g of dimethylformamide were added 7.94 g (0.013 mole) of triphenylsulfonium 2-(2-chlorobutyryloxy)-1,1,3,3,3-pentafluoropropane-1-sulfonate obtained in Synthesis Example 1-24-1, 6.21 g (0.015 mole) of sodium dehydrocholate, and 0.40 g (0.003 mole) of sodium iodide. This was heated and stirred at 80° C. for 11 hours. The reaction solution was allowed to cool down to room temperature, after which 75 g of water and 150 g of dichloromethane were added. The organic layer was taken out and washed with 75 g of water, after which dichloromethane was distilled off in vacuum. To the residue was added 80 g of methyl isobutyl ketone. This was washed three times with 60 g of water, 60 g of a 0.1% sodium hydroxide aqueous solution, and 60 g of water, after which methyl isobutyl ketone was distilled off in vacuum. The residue was purified by silica gel chromatography and recrystallized by diethyl ether, yielding the target compound, triphenylsulfonium 2-{4-[4-(10,13-dimethyl-3,7,12-trioxo-hexadecahydro-cyclopenta[a]phenanthren-17-yl)-pentanoyloxy]-butyryloxy}-1,1,3,3,3-pentafluoropropane-1-sulfonate. White crystals, 6.39 g (yield 50%). The compound had the structure shown below.

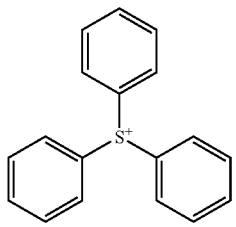

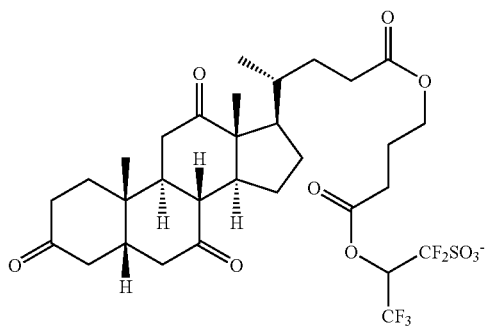

Figure 17:
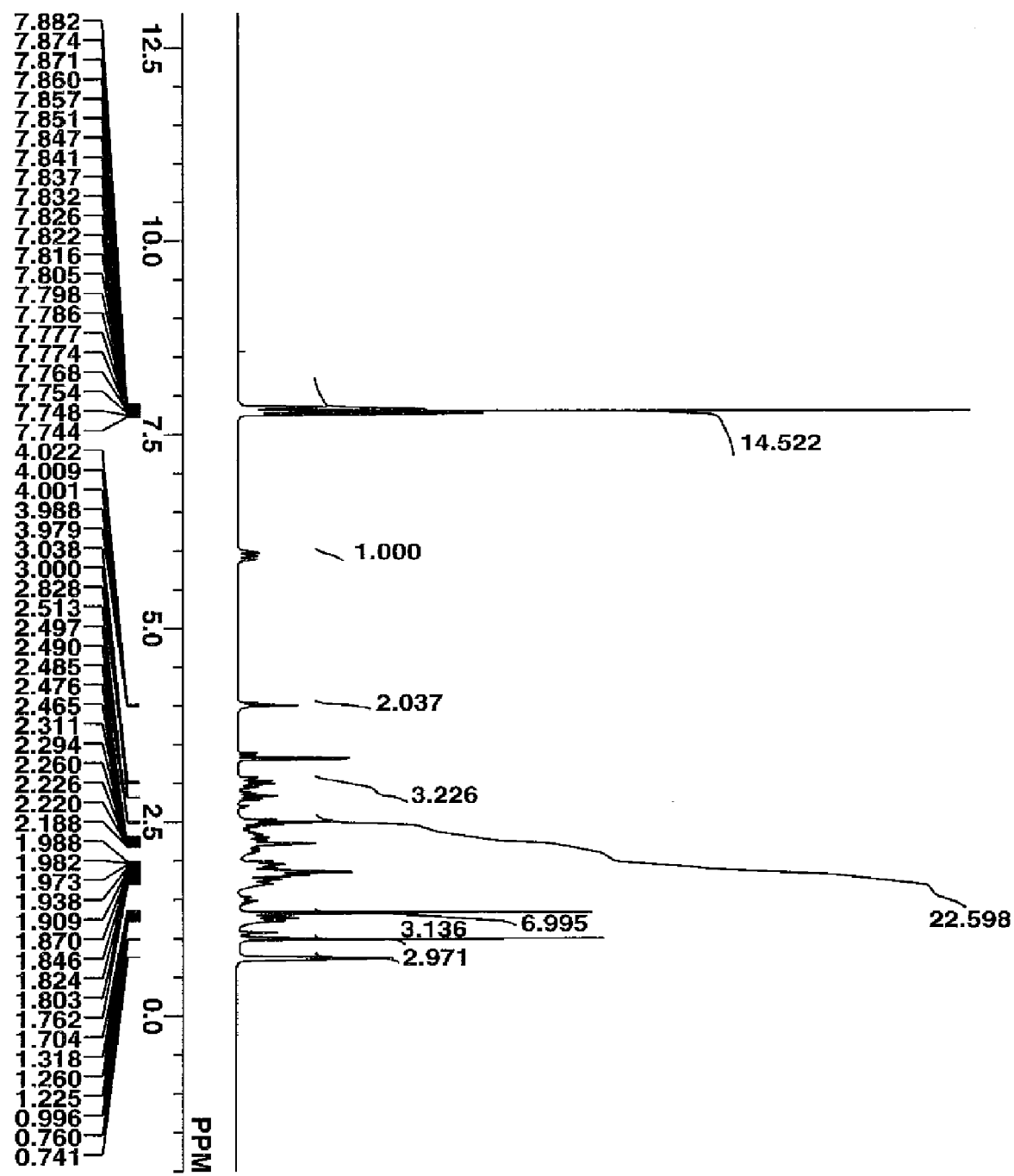
FIG. 17 is a diagram showing the $^1$H-NMR/DMSO-$d_6$ spectrum of PAG-G in Synthesis Example 1-24-2.
Figure 18:
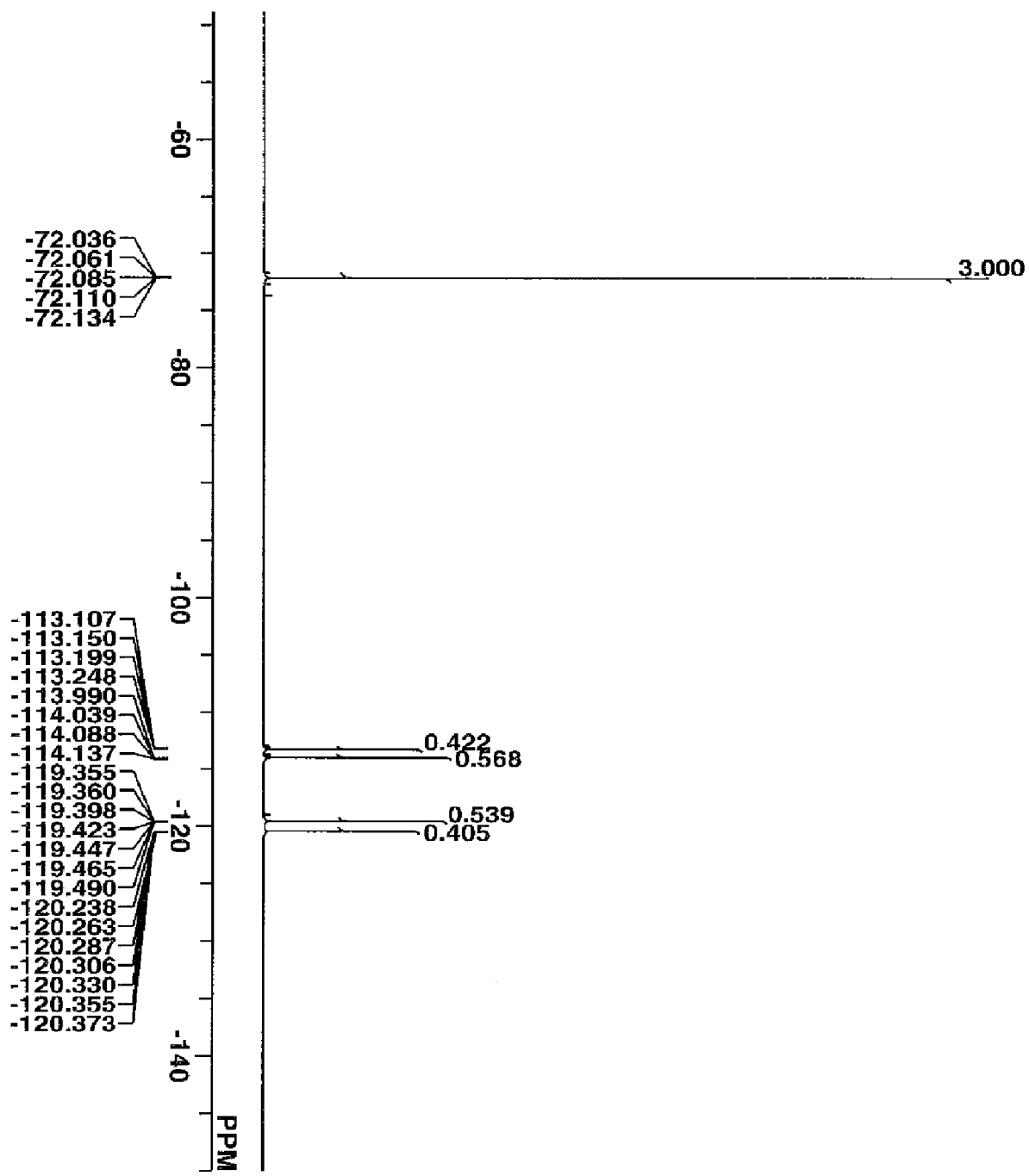
FIG. 18 is a diagram showing the $^{19}$F-NMR/DMSO-$d_6$ spectrum of PAG-G in Synthesis Example 1-24-2.

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 17 and 18. In $^1$H-NMR analysis, minute amounts of residual solvents (diethyl ether, water) was observed.

IR spectra (KBr, cm$^{-1}$) 2967, 2877, 1772, 1706, 1477, 1448, 1380, 1321, 1251, 1216, 1170, 1139, 1103, 1072, 995, 750, 684, 642, 501 TOFMS (MALDI) Positive M$^+$263 (corresponding to (C$_6$H$_5$)$_3$S$^+$) Negative M$^-$699 (corresponding to CF$_3$CH(OCO—C$_{27}$H$_{39}$O$_5$)CF$_2$SO$_3^-$)

By repeating the same procedure as in Synthesis Example 1-24 except that one of PAG2 to PAG8 was used instead of PAG1, triphenylsulfonium 2-hydroxy-1,1,3,3,3-pentafluoropropane-1-sulfonate, a series of compounds can be synthesized in which the cation moiety of PAG-G is replaced by 4-tert-butylphenyldiphenylsulfonium, 4-tert-butoxyphenyldiphenylsulfonium, tris(4-methylphenyl)sulfonium, tris(4-tert-butylphenyl)sulfonium, bis(4-tert-butylphenyl)iodonium, dimethylphenylsulfonium or phenacyltetrahydrothiophenium.

Reference Example 1-1

Synthesis of sodium salt of chorestanyl difluorosulfoacetate

Sodium difluorosulfoacetate and cholestanol were esterified by the method described in JP-A 2006-257078, obtaining the target compound. This crude product was subjected to the subsequent step of cation exchange reaction without purification.

Reference Example 1-2

Synthesis of triphenylsulfonium cholestanyl difluorosulfoacetate (PAG-D)

The triphenylsulfonium chloride aqueous solution (equivalent to 0.018 mole) of Synthesis Example 1-1 and the crude product (0.018 mole), sodium salt of chorestanyl difluorosulfoacetate of Reference Example 1-1 were dissolved in 50 g of dichloromethane and 50 g of methyl isobutyl ketone. The organic layer was washed 5 times with 50 g of water, and then concentrated. To the residue, 40 g of diethyl ether was added for crystallization. The crystals were filtered and dried, obtaining the target compound. White crystals, 1.5 g (two-step yield 10%). The compound had the structure shown below.

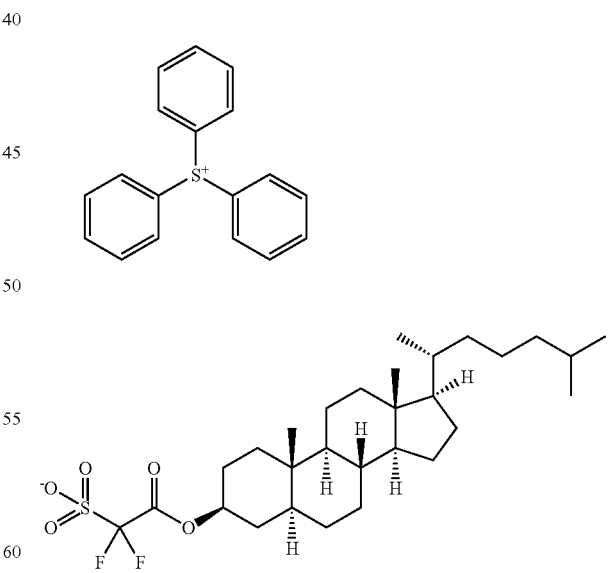

Figure 7:
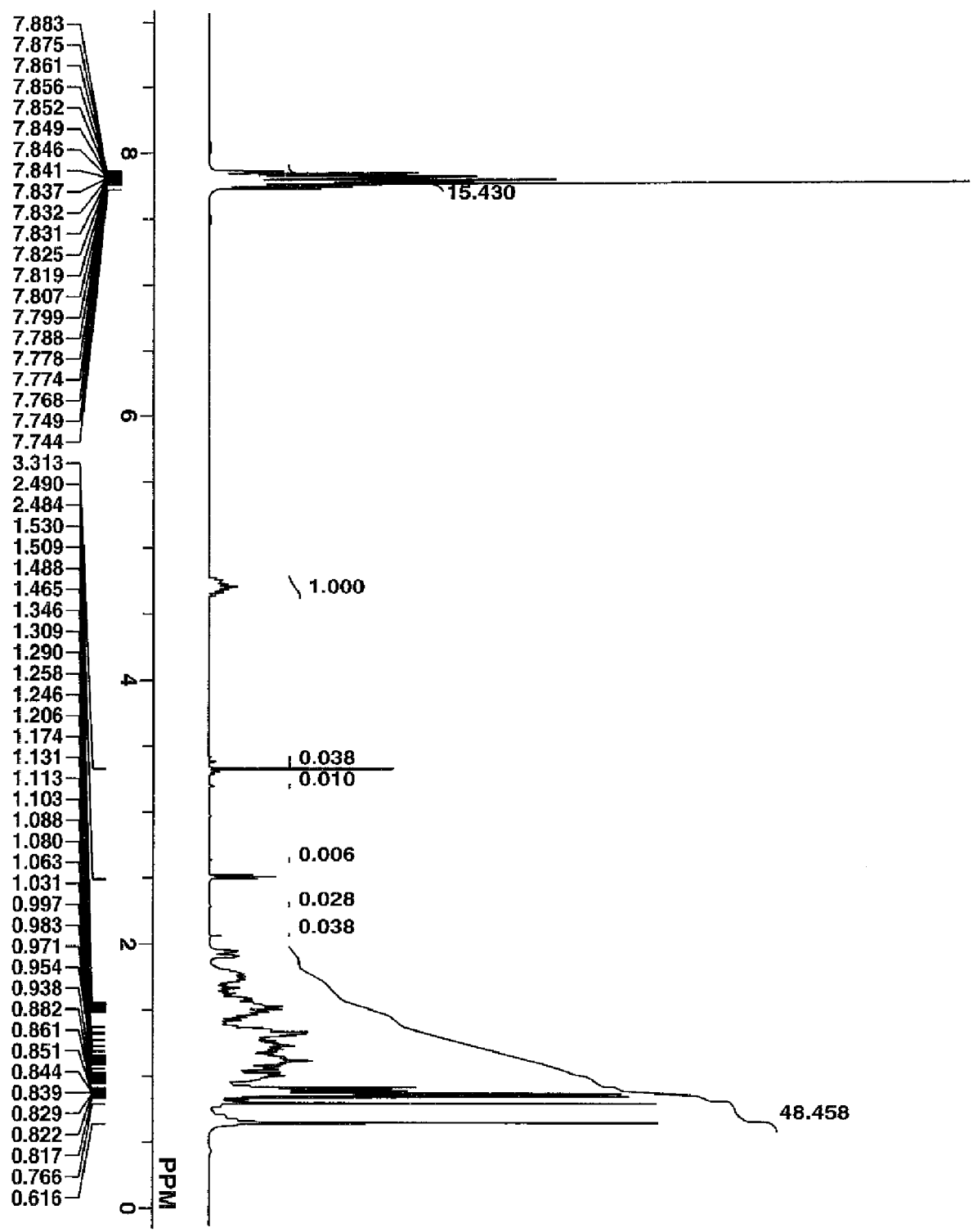
FIG. 7 is a diagram showing the $^1$H-NMR/DMSO-$d_6$ spectrum of PAG-D in Reference Example 1-2.
Figure 8:
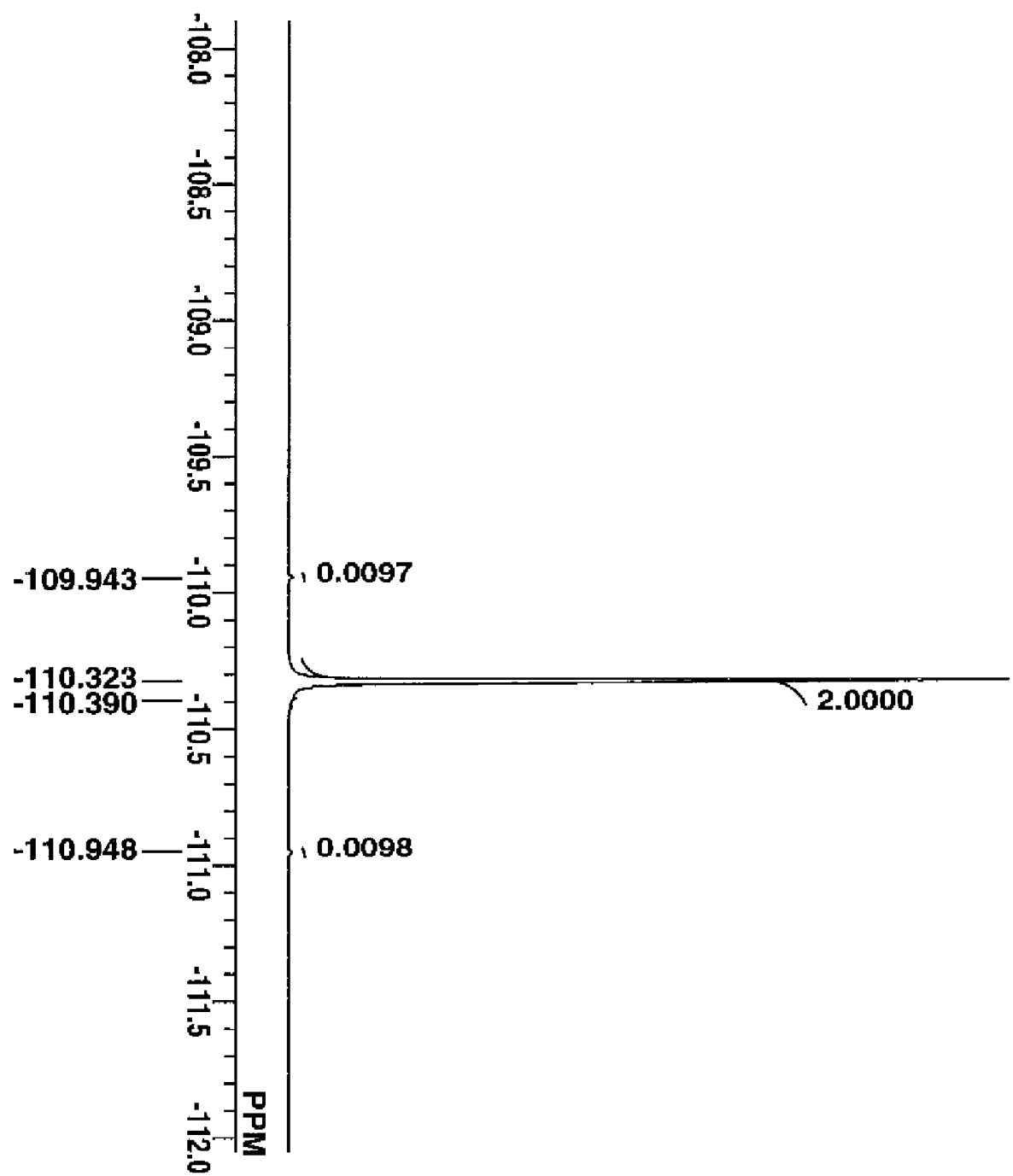
FIG. 8 is a diagram showing the $^{19}$F-NMR/DMSO-$d_6$ spectrum of PAG-D in Reference Example 1-2.

The sulfonium salt was analyzed by spectroscopy. The data of IR spectroscopy and TOFMS are shown below. The NMR spectra, $^1$H-NMR and $^{19}$F-NMR in DMSO-$d_6$ are shown in FIGS. 7 and 8. In $^1$H-NMR analysis, minute amounts of residual solvents (diethyl ether, water) was observed.

IR spectra (KBr, cm$^{-1}$) 2929, 2867, 2850, 1752, 1477, 1446, 1301, 1265, 1251, 1147, 1132, 1070, 995, 754, 686, 653 TOFMS (MALDI) Positive M$^+$263 (corresponding to (C$_6$H$_5$)$_3$S$^+$) Negative M$^-$545 (corresponding to C$_{27}$H$_{47}$OCOCF$_2$SO$_3^-$)

Reference Example 1-3

Synthesis of 4-tert-butylphenyldiphenylsulfonium cholestanyl difluorosulfoacetate (PAG-E)

The target compound was synthesized by the same procedure as in Reference Example 1-2 aside from using the 4-tert-butylphenyldiphenylsulfonium bromide aqueous solution in Synthesis Example 1-2. White crystals, 1.2 g (two-step yield 4%). The compound had the structure shown below.

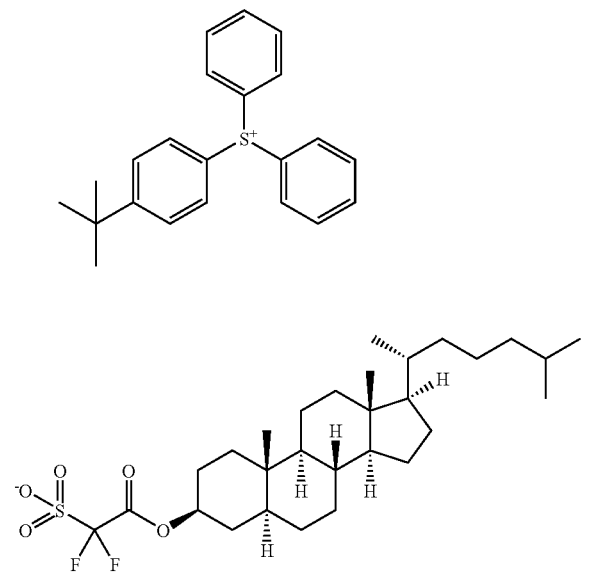

Figure 9:
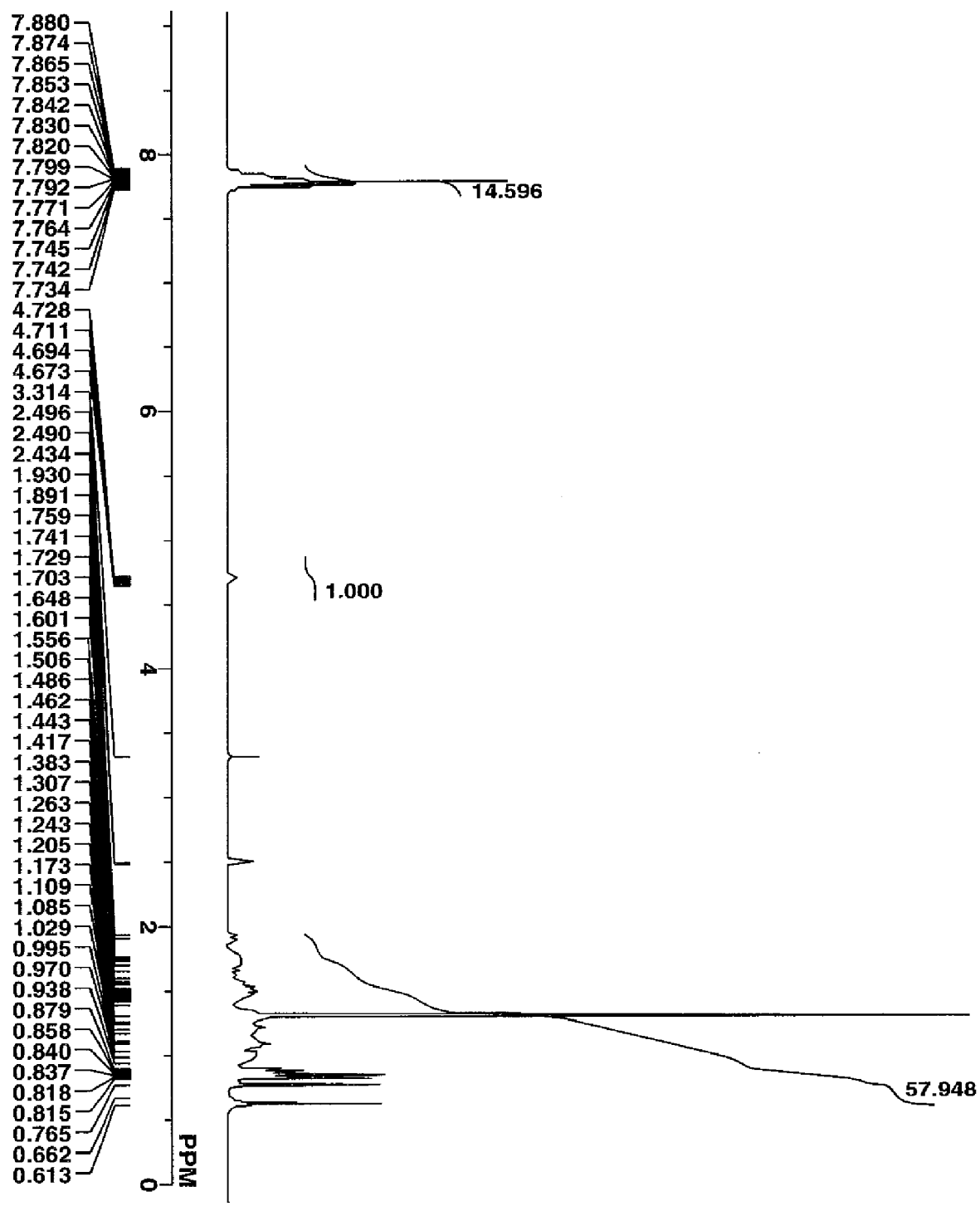
FIG. 9 is a diagram showing the $^1$H-NMR/DMSO-$d_6$ spectrum of PAG-E in Reference Example 1-3.
Figure 10:
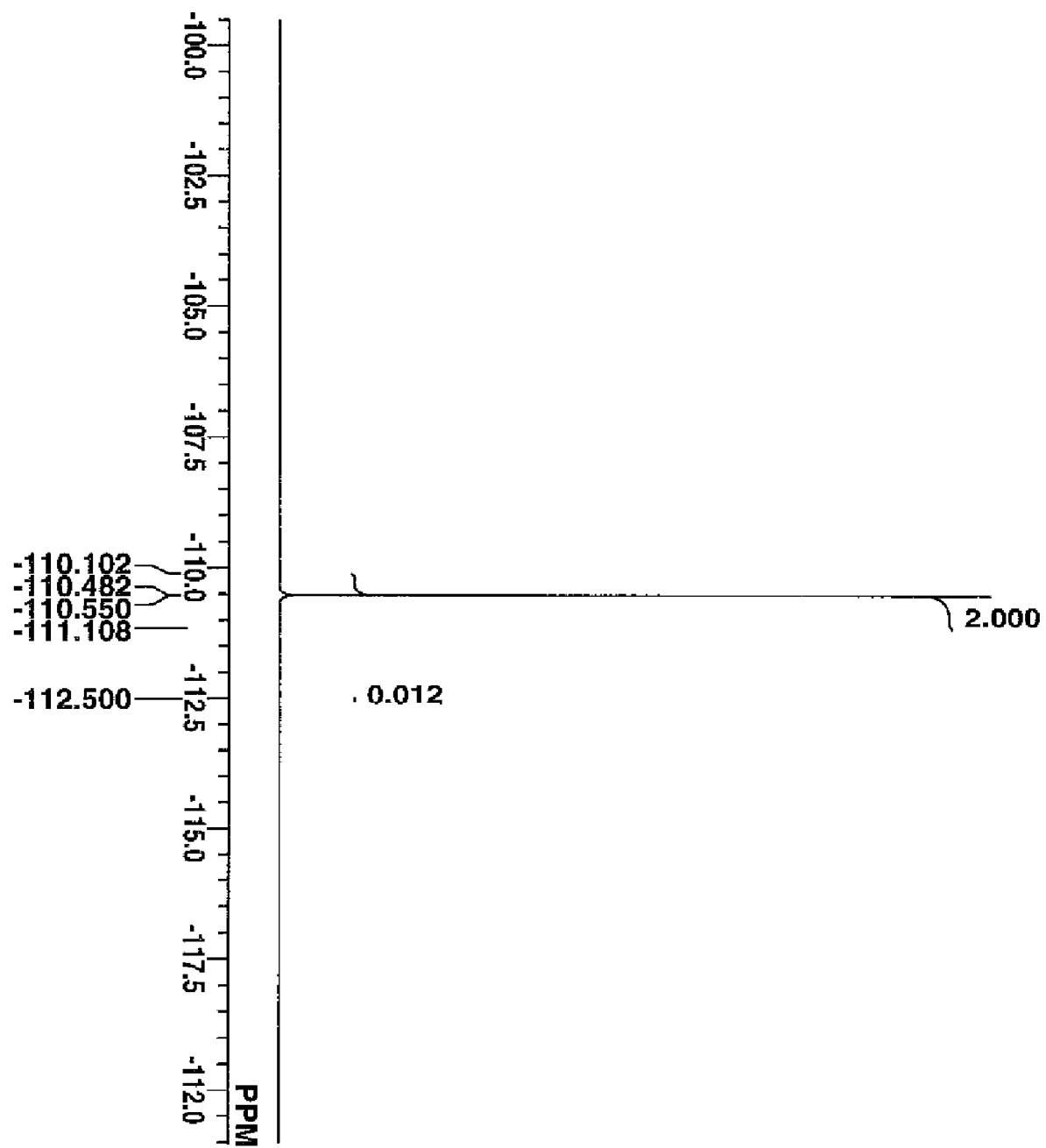
FIG. 10 is a diagram showing the $^{19}$F-NMR/DMSO-$d_6$ spectrum of PAG-E in Reference Example 1-3.

The sulfonium salt was analyzed by spectroscopy. The data of IR spectroscopy and TOFMS are shown below. The NMR spectra, $^1$H-NMR and $^{19}$F-NMR in DMSO-d$_6$ are shown in FIGS. 9 and 10. In $^1$H-NMR analysis, minute amounts of residual solvents (diethyl ether, water) was observed.

IR spectra (KBr, cm$^{-1}$) 2950, 2867, 1756, 1477, 1446, 1332, 1299, 1265, 1249, 1147, 1130, 1070, 997, 754, 686, 655 TOFMS (MALDI) Positive M$^+$319 (corresponding to (C$_{10}$H$_{13}$)(C$_6$H$_5$)$_2$S$^+$) Negative M$^-$545 (corresponding to C$_{27}$H$_{47}$OCOCF$_2$SO$_3^-$)

It is noted that PAG-D in Reference Example 1-2 is described in JP-A 2007-161707, and PAG-E in Reference Example 1-3 is easily presumable therefrom. These compounds are very slightly soluble in propylene glycol monomethyl ether acetate (PGMEA) and cyclohexanone commonly used in resist compositions and thus practically unacceptable. In our experiment, they could not be dissolved in a solvent mixture of PGMEA and cyclohexanone (in a weight ratio 7:3) in a concentration of 1 wt %. In contrast, PAG-A, PAG-B and PAG-C obtained in Synthesis Examples 1-19, 1-21 and 1-22 are fully soluble in the aforementioned solvents and thus practically acceptable.

Polymers for use in the resist compositions of the invention were synthesized in accordance with the following formulation.

Synthesis Example 2-1

Synthesis of Polymer 1

A flask purged with nitrogen was charged with 168.6 g of 2-ethyladamantan-2-yl methacrylate, 85.5 g of 3-hydroxy-1-adamantyl methacrylate, 172.1 g of 2-oxotetrahydrofuran-3-yl methacrylate, and 510 g of propylene glycol methyl ether acetate (PMA) to form a monomer solution. An initiator solution was prepared by adding 14.86 g of 2,2'-azobisisobutyronitrile and 2.6 g of 2-mercaptoethanol to 127 g of PMA. Another flask purged with nitrogen was charged with 292 g of PMA, which was heated at 80° C. while stirring. Thereafter, the monomer solution and the initiator solution were simultaneously added dropwise over 4 hours. After the completion of dropwise addition, the polymerization solution was stirred for a further 2 hours while maintaining the temperature of 80° C., and thereafter, cooled down to room temperature. With vigorous stirring, the polymerization solution was added dropwise to 12 kg of methanol, whereupon a copolymer precipitated. The copolymer was collected by filtration, washed twice with 3 kg of methanol, and vacuum dried at 50° C. for 20 hours, obtaining 384 g of the copolymer in white powder form. The copolymer was analyzed by $^{13}$C-NMR, finding a copolymerization compositional ratio of 33/18/49 mol % in the described order of monomers. It was also analyzed by GPC, finding a weight average molecular weight (Mw) of 6,000 versus polystyrene standards.

Polymer 1

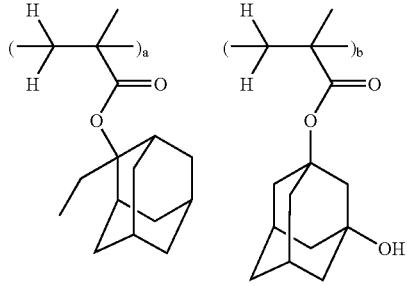

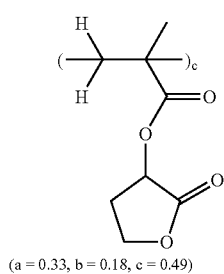

(a = 0.33, b = 0.18, c = 0.49)

Synthesis Examples 2-2 to 2-25

Synthesis of Polymers 2 to 25, 36 to 39

A series of resins as shown in Table 1 were prepared by the same procedure as in Synthesis Example 2-1 except that the type and ratio of monomers were changed. The units in Table 1 have the structure shown in Tables 2 to 6. In Table 1, the ratio of units is a molar ratio.

Synthesis Examples 2-26 to 2-32

Synthesis of Polymers 26 to 32

Each of Polymers 19 to 25 obtained by the above formulation was dissolved in a solvent mixture of methanol and tetrahydrofuran, to which oxalic acid was added. Deprotection reaction took place at 40° C. The solution was neutralized with pyridine and purified by a standard reprecipitation technique, obtaining a polymer comprising hydroxystyrene units.

Synthesis Examples 2-33 to 2-35

Synthesis of Polymers 33 to 35

Polymers 26 to 28 were reacted with ethyl vinyl ether under acidic conditions or with 1-chloro-1-methoxy-2-methyl-propane under basic conditions, obtaining Polymers 33 to 35.

With respect to the deprotection and protection of polyhydroxystyrene derivatives in Synthesis Examples 2-26 to 2-35, reference should be made to JP-A 2004-115630 and JP-A 2005-8766.

TABLE 2

A-1M (R = CH$_3$)    A-2M (R = CH$_3$)
A-1A (R = H)         A-2A (R = H)

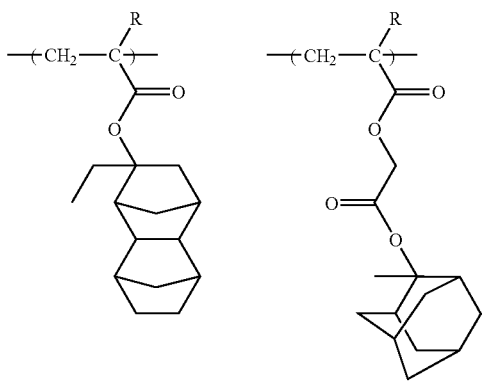

TABLE 1

|  | Resin | Unit 1 (ratio) | Unit 2 (ratio) | Unit 3 (ratio) | Unit 4 (ratio) | Unit 5 (ratio) |
|---|---|---|---|---|---|---|
| Synthesis Example 2-1 | P-01 | A-3M (0.33) | B-1M (0.18) |  | B-6M (0.49) |  |
| 2-2 | P-02 | A-6M (0.25) | B-1M (0.25) | C-3M (0.10) | B-3M (0.40) |  |
| 2-3 | P-03 | A-1M (0.25) | B-1M (0.25) | C-3M (0.10) | B-3M (0.40) |  |
| 2-4 | P-04 | A-5M (0.30) | B-1M (0.25) | C-2M (0.10) | B-3M (0.35) |  |
| 2-5 | P-05 | A-2M (0.40) | B-1M (0.25) |  | B-3M (0.35) |  |
| 2-6 | P-06 | A-1M (0.25) | B-1M (0.25) | A?2M (0.10) | B-3M (0.40) |  |
| 2-7 | P-07 | A-1M (0.30) | B-1M (0.15) | C-4M (0.10) | B-3M (0.45) |  |
| 2-8 | P-08 | A-5M (0.25) | B-1M (0.25) | C-1M (0.10) | B-3M (0.40) |  |
| 2-9 | P-09 | A-3M (0.35) | B-1M (0.35) |  | B-4M (0.30) |  |
| 2-10 | P-10 | A-3M (0.35) | B-1M (0.35) |  | B-7M (0.30) |  |
| 2-11 | P-11 | A-3M (0.30) | B-1M (0.26) | B-8M (0.10) | B-6M (0.34) |  |
| 2-12 | P-12 | A-1M (0.25) | B-1M (0.25) | B-8M (0.10) | B-9M (0.40) |  |
| 2-13 | P-13 | A-1M (0.25) | B-1M (0.25) | C-1M (0.10) | B-3M (0.40) |  |
| 2-14 | P-14 | A-4M (0.30) | B-1M (0.25) |  | B-3M (0.45) |  |
| 2-15 | P-15 | A-1M (0.30) | B-2M (0.35) |  | B-6M (0.35) |  |
| 2-16 | P-16 | A-1M (0.30) | B-1M (0.35) |  | B-3M (0.35) |  |
| 2-17 | P-17 | A-1M (0.35) | B-1M (0.25) |  | B-5M (0.40) |  |
| 2-18 | P-18 | A-1M (0.20) | B-1M (0.25) | A-5M (0.20) | B-3M (0.35) |  |
| 2-19 | P-19 | D-2 (1.0) |  |  |  |  |
| 2-20 | P-20 | D-2 (0.80) | D-4 (0.20) |  |  |  |
| 2-21 | P-21 | D-2 (0.70) | D-5 (0.30) |  |  |  |
| 2-22 | P-22 | D-2 (0.70) | D-4 (0.15) |  | D-7 (0.15) |  |
| 2-23 | P-23 | D-2 (0.80) | A-1M (0.15) |  | D-7 (0.05) |  |
| 2-24 | P-24 | D-2 (0.75) | A-3M (0.15) |  | D-7 (0.10) |  |
| 2-25 | P-25 | D-2 (0.80) | D-6 (0.20) |  |  |  |
| 2-26 | P-26 | D-1 (1.0) |  |  |  |  |
| 2-27 | P-27 | D-1 (0.80) | D-4 (0.20) |  |  |  |
| 2-28 | P-28 | D-1 (0.70) | D-5 (0.30) |  |  |  |
| 2-29 | P-29 | D-1 (0.70) | D-4 (0.15) |  | D-7 (0.15) |  |
| 2-30 | P-30 | D-1 (0.80) | A-1M (0.15) |  | D-7 (0.05) |  |
| 2-31 | P-31 | D-1 (0.75) | A-3M (0.15) |  | D-7 (0.10) |  |
| 2-32 | P-32 | D-1 (0.80) | D-6 (0.20) |  |  |  |
| 2-33 | P-33 | D-1 (0.80) | D-2 (0.20) |  |  |  |
| 2-34 | P-34 | D-1 (0.80) | D-3 (0.20) |  |  |  |
| 2-35 | P-35 | D-1 (0.70) | D-4 (0.20) |  | D-3 (0.10) |  |
| 2-36 | P-36 | A-1M (0.25) | B-1M (0.10) | A-8M (0.10) | B-8M (0.25) | B-9M (0.30) |
| 2-37 | P-37 | A-1M (0.25) | B-1M (0.10) | A-7M (0.10) | B-8M (0.25) | B-9M8 (0.30) |
| 2-38 | P-38 | A-1M (0.30) | B-10M (0.30) | B-3M (0.40) |  |  |
| 2-39 | P-39 | A-1M (0.25) | B-10M (0.10) | C-3M (0.10) | B-3M (0.40) | B-1MM (0.15) |

TABLE 2-continued
A-3M (R = CH₃)  A-4M (R = CH₃)
A-3A (R = H)    A-4A (R = H)
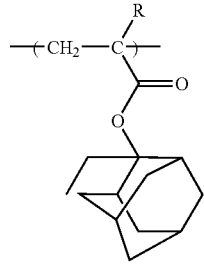 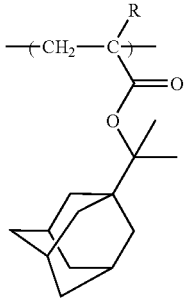
A-5M (R = CH₃)  A-6M (R = CH₃)
A-5A (R = H)    A-6A (R = H)
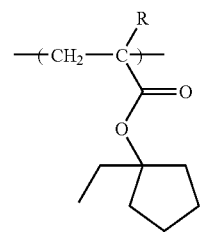 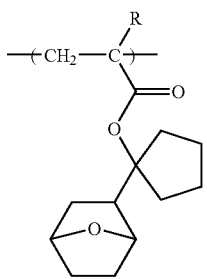
A-7M (R = CH₃)  A-8M (R = CH₃)
A-7A (R = H)    A-8A (R = H)
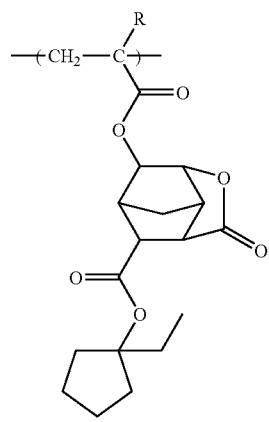 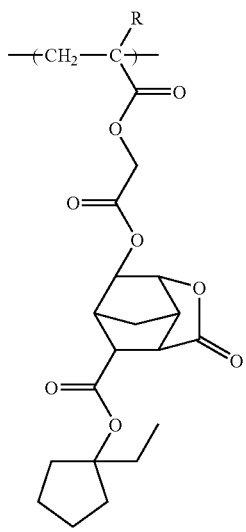
TABLE 3
B-1M (R = CH₃)  B-2M (R = CH₃)
B-1A (R = H)    B-2A (R = H)
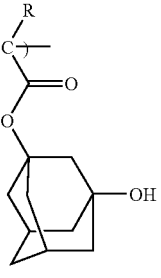 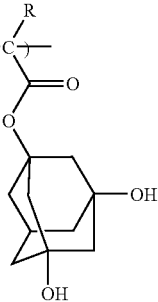
B-3M (R = CH₃)  B-4M (R = CH₃)
B-3A (R = H)    B-4A (R = H)
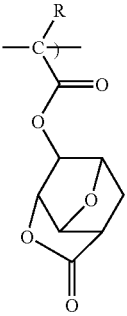 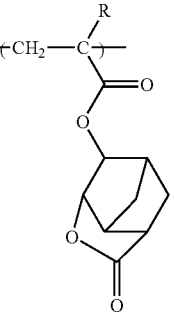
B-5M (R = CH₃)  B-6M (R = CH₃)
B-5A (R = H)    B-6A (R = H)
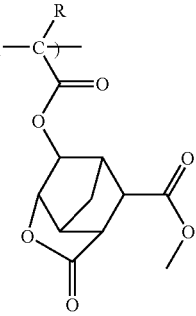 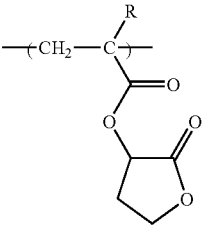

TABLE 3-continued
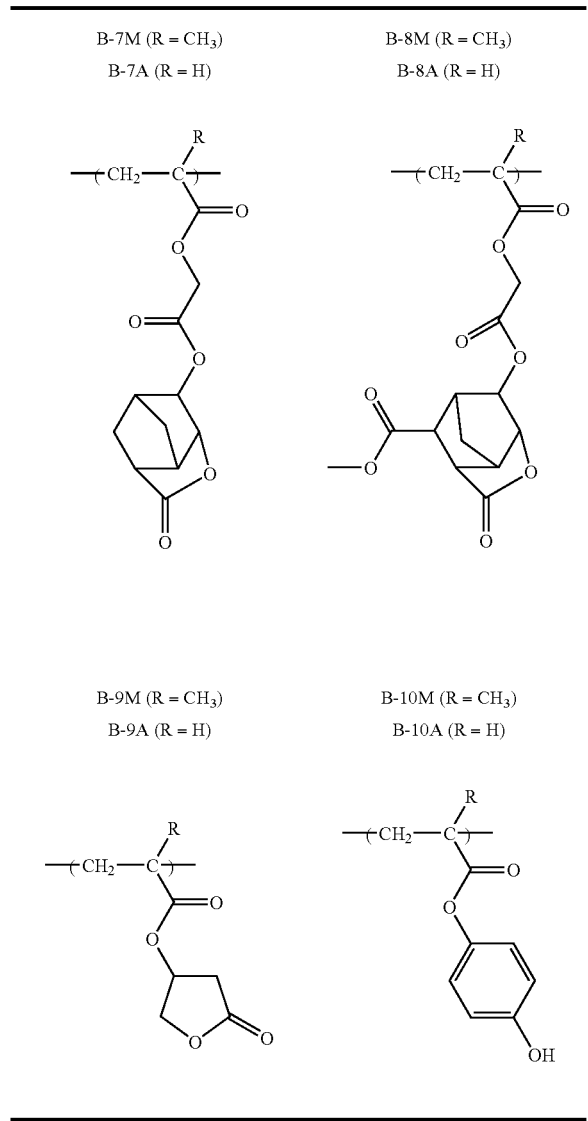
TABLE 4
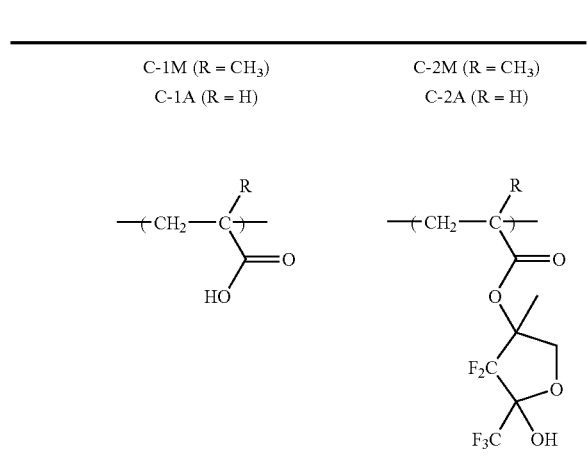
TABLE 4-continued
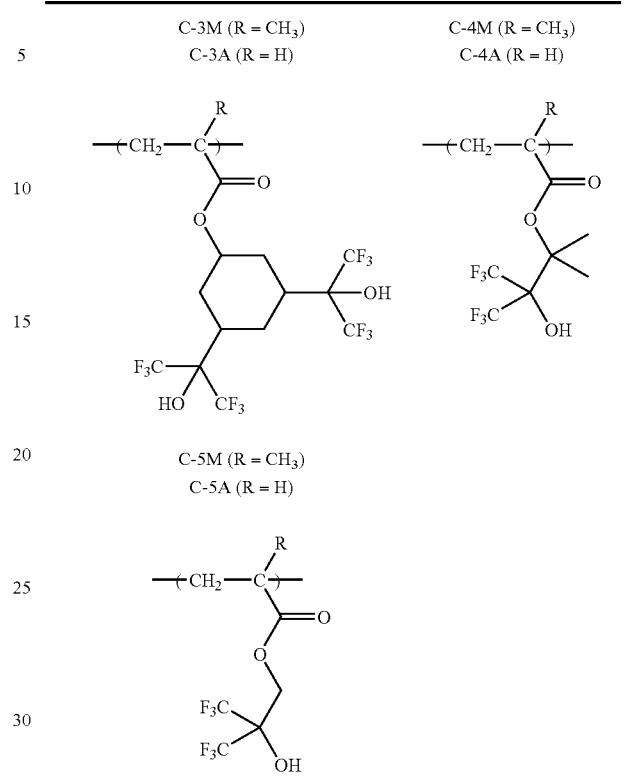
TABLE 5
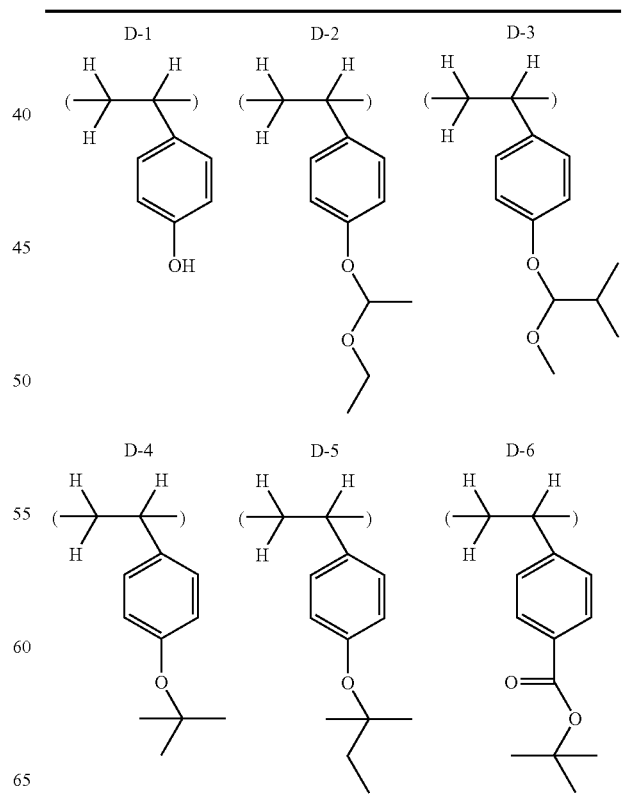

TABLE 5-continued

D-7

Additionally, the following polymers were prepared by well-known techniques.

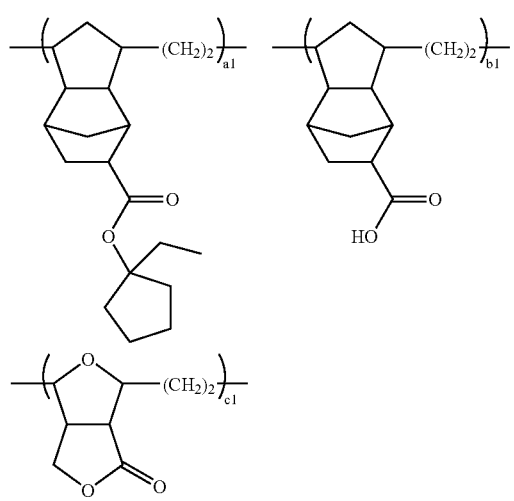

Polymer 40

(a1 = 0.35, b1 = 0.15, c1 = 0.50, Mw = 8,100)

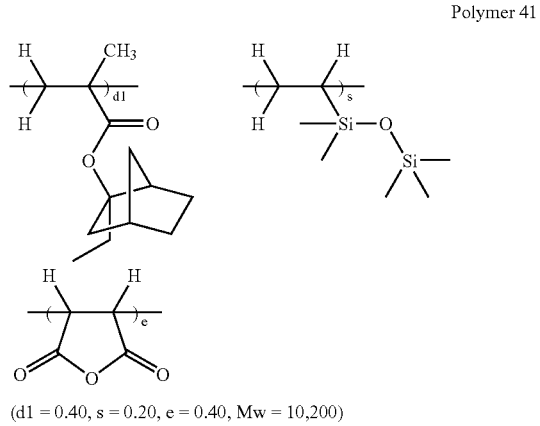

Polymer 41

(d1 = 0.40, s = 0.20, e = 0.40, Mw = 10,200)

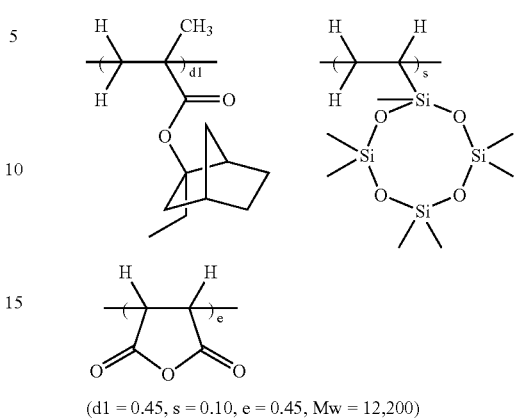

Polymer 42

(d1 = 0.45, s = 0.10, e = 0.45, Mw = 12,200)

Examples 1 to 36 & Comparative Examples 1 to 4

Preparation of Resist Composition

Resist compositions were prepared by dissolving the photoacid generators of Synthesis Example 1, Polymers P-01 to P-42 of Synthesis Example 2 as the base resin, and a quencher in a solvent containing 0.01 wt % of surfactant KH-20 (Seimi Chemical Co., Ltd.) according to the formulation shown in Table 6. They were filtered through a Teflon® filter having a pore size of 0.2 μm, giving resist solutions.

In Table 6, the solvents, quenchers, photoacid generators in Comparative Examples, and acid crosslinker are shown below. Polymers 1 to 42 are designated P-01 to P-42, respectively.

| | |
|---|---|
| PGMEA: | propylene glycol monomethyl ether acetate |
| CyHO: | cyclohexanone |
| EL: | ethyl lactate |
| Base-1: | triethanolamine |
| Base-2: | tris[2-(methoxymethoxy)ethyl]amine |
| PAG-I: | triphenylsulfonium perfluoro-1-butanesulfonate |
| PAG-II: | triphenylsulfonium 2-(adamantane-1-carbonyloxy)-1,1,3,3,3-pentafluoropropane-1-sulfonate (described in JP-A 2007-145797) |
| PAG-III: | triphenylsulfonium (adamantan-1-yl)methoxy-carbonyldifluoromethanesulfonate (described in JP-A 2004-4561) |
| TMGU: | 1,3,4,6-tetramethoxymethylglycoluril |

TABLE 6

| | | Resist composition | Resin (pbw) | PAG (pbw) | Additive (pbw) | Solvent 1 (pbw) | Solvent 2 (pbw) |
|---|---|---|---|---|---|---|---|
| Example | 1 | R-01 | P-01(80) | PAG-A(10.2) | Base-2(1.10) | PGMEA(896) | CyHO(364) |
| | 2 | R-02 | P-01(80) | PAG-B(11.2) | Base-2(1.10) | PGMEA(896) | CyHO(364) |
| | 3 | R-03 | P-01(80) | PAG-C(10.5) | Base-2(1.10) | PGMEA(896) | CyHO(364) |
| | 4 | R-04 | P-02(80) | PAG-A(10.2) | Base-2(1.10) | PGMEA(896) | CyHO(364) |
| | 5 | R-05 | P-03(80) | PAG-A(10.2) | Base-2(1.10) | PGMEA(896) | CyHO(364) |
| | 6 | R-06 | P-04(80) | PAG-F(11.2) | Base-2(1.10) | PGMEA(896) | CyHO(364) |
| | 7 | R-07 | P-05(80) | PAG-G(10.2) | Base-2(1.10) | PGMEA(896) | CyHO(364) |

TABLE 6-continued

|  | Resist composition | Resin (pbw) | PAG (pbw) | Additive (pbw) | Solvent 1 (pbw) | Solvent 2 (pbw) |
|---|---|---|---|---|---|---|
|  | 8 R-08 | P-06(80) | PAG-A(6.0) PAG-II(3.1) | Base-2(1.10) | PGMEA(896) | CyHO(364) |
|  | 9 R-09 | P-07(80) | PAG-A(10.2) | Base-2(1.10) | PGMEA(896) | CyHO(364) |
|  | 10 R-10 | P-08(80) | PAG-A(10.2) | Base-2(1.10) | PGMEA(896) | CyHO(364) |
|  | 11 R-11 | P-09(80) | PAG-A(10.2) | Base-2(1.10) | PGMEA(896) | CyHO(364) |
|  | 12 R-12 | P-10(80) | PAG-A(10.2) | Base-2(1.10) | PGMEA(896) | CyHO(364) |
|  | 13 R-13 | P-11(80) | PAG-A(10.2) | Base-2(1.10) | PGMEA(896) | CyHO(364) |
|  | 14 R-14 | P-12(80) | PAG-A(10.2) | Base-2(1.10) | PGMEA(896) | CyHO(364) |
|  | 15 R-15 | P-13(80) | PAG-A(6.0) PAG-I(2.7) | Base-2(1.10) | PGMEA(896) | CyHO(364) |
|  | 16 R-16 | P-14(80) | PAG-A(10.2) | Base-2(1.10) | PGMEA(896) | CyHO(364) |
|  | 17 R-17 | P-15(80) | PAG-A(10.2) | Base-2(1.10) | PGMEA(896) | CyHO(364) |
|  | 18 R-18 | P-16(80) | PAG-A(10.2) | Base-2(1.10) | PGMEA(896) | CyHO(364) |
|  | 19 R-19 | P-17(80) | PAG-A(10.2) | Base-2(1.10) | PGMEA(896) | CyHO(364) |
|  | 20 R-20 | P-18(80) | PAG-A(10.2) | Base-1(0.58) | PGMEA(896) | CyHO(364) |
|  | 21 R-21 | P-03(40) P-40(40) | PAG-A(10.2) | Base-1(0.58) | PGMEA(896) | CyHO(364) |
|  | 22 R-22 | P-5(40) P-40(40) | PAG-A(10.2) | Base-1(0.58) | PGMEA(896) | CyHO(364) |
|  | 23 R-23 | P-41(80) | PAG-A(8.5) | Base-1(0.58) | PGMEA(896) | CyHO(364) |
|  | 24 R-24 | P-42(80) | PAG-A(8.5) | Base-1(0.58) | PGMEA(896) | CyHO(364) |
|  | 25 R-25 | P-27(80) | PAG-A(10.2) | Base-1(0.80) | PGMEA(896) | EL(364) |
|  | 26 R-26 | P-28(80) | PAG-A(10.2) | Base-1(0.80) | PGMEA(896) | EL(364) |
|  | 27 R-27 | P-29(80) | PAG-A(10.2) | Base-1(0.80) | PGMEA(896) | EL(364) |
|  | 28 R-28 | P-30(80) | PAG-A(10.2) | Base-1(0.80) | PGMEA(896) | EL(364) |
|  | 29 R-29 | P-31(80) | PAG-A(10.2) | Base-1(0.80) | PGMEA(896) | EL(364) |
|  | 30 R-30 | P-32(80) | PAG-A(10.2) | Base-1(0.80) | PGMEA(896) | EL(364) |
|  | 31 R-31 | P-35(80) | PAG-A(10.2) | Base-1(0.80) | PGMEA(896) | EL(364) |
|  | 32 R-32 | P-26(80) | PAG-A(10.2) | Base-1(0.3) TMGU(10) | PGMEA(896) | EL(364) |
|  | 33 R-33 | P-36(80) | PAG-A(10.2) | Base-2(1.10) | PGMEA(896) | CyHO(364) |
|  | 34 R-34 | P-37(80) | PAG-A(10.2) | Base-2(1.10) | PGMEA(896) | CyHO(364) |
|  | 35 R-35 | P-38(80) | PAG-A(10.2) | Base-2(1.10) | PGMEA(896) | CyHO(364) |
|  | 36 R-36 | P-39(80) | PAG-A(10.2) | Base-2(1.10) | PGMEA(896) | CyHO(364) |
| Comparative Example | 1 R-101 | P-01(80) | PAG-I(6.5) | Base-2(1.10) | PGMEA(896) | CyHO(364) |
|  | 2 R-102 | P-01(80) | PAG-II(7.6) | Base-2(1.10) | PGMEA(896) | CyHO(364) |
|  | 3 R-103 | P-01(80) | PAG-III(6.8) | Base-2(1.10) | PGMEA(896) | CyHO(364) |
|  | 4 R-104 | P-27(80) | PAG-I(6.5) | Base-1(0.58) | PGMEA(896) | EL(364) |

Examples 37 to 60 & Comparative Examples 5 to 7

Evaluation of Resist Resolution and Mask Fidelity

An antireflective coating liquid ARC-29A (Nissan Chemical Co., Ltd.) was coated onto a silicon substrate and baked at 200° C. for 60 seconds to form an antireflective coating of 78 nm thick. The resist solution, prepared above, was spin coated onto the antireflective coating and baked on a hot plate at 120° C. for 60 seconds, forming a resist film of 160 nm thick. The resist film was exposed by means of an ArF excimer laser microstepper model NSR-S307E (Nikon Corp., NA 0.85, 4/5 annular illumination, Cr mask), post-exposure baked (PEB) at the temperature shown in Table 7 for 60 seconds, and developed with a 2.38 wt % aqueous solution of tetramethylammonium hydroxide (TMAH) for 60 seconds.

An optimum exposure dose (sensitivity Eop, mJ/cm$^2$) was the exposure which provided a 1:1 resolution at the top and bottom of a 80-nm grouped line-and-space pattern. The minimum line width (nm) of a line-and-space pattern which was ascertained separate at this dose was the resolution of a test resist. For the evaluation of pattern density dependency, a 1:10 isolated line pattern with an on-mask size of 130 nm was formed at the optimum exposure and determined for an actual on-wafer size, which was reported as mask fidelity (a larger value of on-wafer size is better). For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude.

The test results of resist compositions are shown in Table 7.

TABLE 7

|  |  | Resist composition | PEB temp. (° C.) | Eop (mJ/cm$^2$) | Maximum resolution (nm) | Mask fidelity (nm) | Exposure latitude (%) |
|---|---|---|---|---|---|---|---|
| Example | 37 | R-01 | 100 | 32 | 65 | 75 | 13 |
|  | 38 | R-02 | 100 | 40 | 70 | 75 | 14 |
|  | 39 | R-03 | 100 | 42 | 70 | 80 | 14 |
|  | 40 | R-04 | 100 | 32 | 65 | 80 | 14 |
|  | 41 | R-05 | 100 | 30 | 65 | 80 | 14 |

TABLE 7-continued

|  | | Resist composition | PEB temp. (° C.) | Eop (mJ/cm$^2$) | Maximum resolution (nm) | Mask fidelity (nm) | Exposure latitude (%) |
|---|---|---|---|---|---|---|---|
|  | 42 | R-06 | 100 | 40 | 70 | 80 | 13 |
|  | 43 | R-07 | 110 | 32 | 70 | 80 | 14 |
|  | 44 | R-08 | 100 | 30 | 70 | 75 | 13 |
|  | 45 | R-09 | 100 | 32 | 70 | 78 | 13 |
|  | 46 | R-10 | 100 | 30 | 65 | 70 | 13 |
|  | 47 | R-11 | 105 | 35 | 70 | 70 | 13 |
|  | 48 | R-12 | 100 | 33 | 70 | 70 | 13 |
|  | 49 | R-13 | 100 | 32 | 70 | 75 | 13 |
|  | 50 | R-14 | 100 | 33 | 70 | 78 | 13 |
|  | 51 | R-15 | 100 | 32 | 65 | 75 | 13 |
|  | 52 | R-16 | 100 | 30 | 65 | 80 | 14 |
|  | 53 | R-17 | 100 | 30 | 70 | 80 | 13 |
|  | 54 | R-18 | 100 | 32 | 70 | 78 | 13 |
|  | 55 | R-19 | 100 | 33 | 70 | 75 | 13 |
|  | 56 | R-20 | 100 | 31 | 70 | 80 | 13 |
|  | 57 | R-21 | 100 | 30 | 70 | 75 | 13 |
|  | 58 | R-22 | 100 | 33 | 70 | 75 | 13 |
|  | 59 | R-23 | 100 | 30 | 70 | 78 | 12 |
|  | 60 | R-24 | 100 | 30 | 70 | 80 | 12 |
|  | 61 | R-33 | 100 | 30 | 65 | 78 | 12 |
|  | 62 | R-34 | 100 | 34 | 70 | 78 | 13 |
| Comparative | 5 | R-101 | 100 | 28 | 75 | 60 | 10 |
| Example | 6 | R-102 | 100 | 30 | 70 | 65 | 11 |
|  | 7 | R-103 | 100 | 32 | 75 | 65 | 12 |

Examples 63 to 65 & Comparative Example 8

Simulative immersion photolithography was carried out using the resist compositions (R-01, R-04, R-05) of the invention and the resist composition (R-101) for comparison. Specifically, a resist film of 125 nm thick was formed on a wafer by a procedure as described above and exposed by means of an ArF excimer laser microstepper model S307E (Nikon Corp., dipole). Immediately after the exposure, deionized water was fed over the entire surface of the wafer, whereby the exposed surface of resist was immersed in deionized water for 60 seconds (puddle). The wafer was rotated to spin off the water, followed by ordinary PEB and development. The number of defects in the pattern formed after development was counted by a wafer inspection system WINWIN 50-1200L (Tokyo Seimitsu Co., Ltd.). A defect density was computed therefrom.

Defect density (/cm$^2$) = (total number of detected defects)/(test area).

Pattern formed: repetitive pattern of 80 nm (pitch 160 nm) line-and-space

Defect detection: light source UV. detection pixel size 0.125 μm, cell-to-cell mode Additionally, the pattern profile in resist cross-section was observed under a scanning electron microscope (SEM). The results are shown in Table 8.

TABLE 8

|  | Resist composition | Defect density (/cm$^2$) | Pattern profile |
|---|---|---|---|
| Example 63 | R-01 | ≦0.05 | rectangular |
| Example 64 | R-04 | ≦0.05 | rectangular |
| Example 65 | R-05 | ≦0.05 | rectangular |
| Comparative Example 8 | R-101 | 10 | extremely bulged top |

As is evident from Tables 7 and 8, the resist compositions of the invention have a high sensitivity, high resolution and minimized pattern density dependency, and invite neither profile changes nor defects during a long term of water rinsing as compared with the prior art composition, suggesting an ability to comply with the immersion photolithography.

Examples 66 to 68 & Comparative Example 9

Measurement of Leach-out

To 100 parts by weight of the resist compositions (R-01, R-02, R-03) was added 0.2 part by weight of a surfactant (Surfactant-1, shown below) which was insoluble in water, but soluble in alkaline developer. The resulting resist compositions (R-01', R-02', R-03') and comparative composition (R-102) were spin coated on silicon substrates, then baked at 100° C. for 60 seconds to give photoresist films having a thickness of 120 nm. Using an ArF scanner S305B (Nikon Corp.), the entire surface of the photoresist film was irradiated through an open frame at an energy dose of 50 mJ/cm$^2$.

Surfactant-1: a copolymer of 3,3,3-trifluoro-2-hydroxy-1,1-dimethyl-2-trifluoromethylpropyl methacrylate and 2,2,3,3,4,4,5,5-octafluoropentyl methacrylate in a molar ratio of 80:20, with Mw=8,000

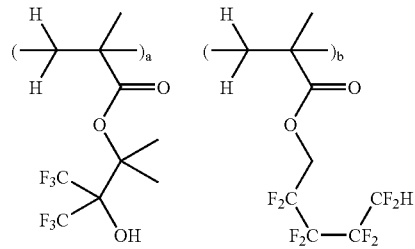

Then a true circle ring of Teflon® having an inner diameter of 10 cm was placed on the resist film, 10 mL of deionized water was carefully injected inside the ring, and the resist film was kept in contact with water at room temperature for 60 seconds. Thereafter, the water was recovered, and a concentration of PAG anion in the water was quantitatively measured by an LC-MS analyzer (Agilent). The anion concentration measured indicates an amount of anions leached out for 60 seconds. The results are shown in Table 9.

TABLE 9

|  | Resist composition | Anion leach-out (ppb) |
|---|---|---|
| Example 66 | R-01' | ≦5 (undetectable) |
| Example 67 | R-02' | ≦5 (undetectable) |
| Example 68 | R-03' | ≦5 (undetectable) |
| Comparative Example 9 | R-102 | 30 |

As is evident from Table 9, the resist compositions of the invention are effective for preventing the generated acid from being leached out in water when processed by immersion lithography using water. They are expected to experience a minimized change of pattern profile by immersion lithography and cause little damage to the exposure tool.

Examples 69, 70 & Comparative Example 10

Evaluation of Resolution on EB Exposure

On a 8-inch silicon wafer having an antireflective coating (DUV-44 by Brewer Science) of 610 Å thick coated thereon, each of the resist compositions (R-25, R-32) of the invention or a comparative resist composition (R-104) was spin coated and heat treated at 100° C. for 60 seconds to form a resist film of 2000 Å thick. Using an EB lithography system HL-800D (Hitachi Hitechnologies, Ltd.) at an accelerating voltage of 50 keV, exposure was performed on the resist film. The resist film was post-exposure baked (PEB) at 120° C. for 60 seconds and developed with a 2.38 wt % TMAH aqueous solution, obtaining a positive pattern (Example 69, Comparative Example 10) or a negative pattern (Example 70).

The resist pattern was evaluated as follows. The optimum exposure (sensitivity, Eop) was defined as the exposure dose ($\mu C/cm^2$) which provided a 1:1 resolution at the top and bottom of a 0.12-μm line-and-space pattern. The resolution of the resist was defined as the minimum line width of a line-and-space pattern that was ascertained separate at the optimum exposure. The profile of the resolved resist pattern was evaluated by observing a cross section of the resist under a SEM.

The post-exposure delay (PED) in vacuum was evaluated by exposing the coated wafer on an EB lithography system, holding it in the vacuum system for 24 hours, thereafter effecting PEB and development. The size of lines of a 0.12-μm line-and-space pattern was measured and a percent change thereof was calculated. If the line size increased by 0.012 μm, the change is reported as +10%. A smaller change indicates better stability. The test results are shown in Table 10.

TABLE 10

|  | Resist composition | Eop ($\mu C/cm^2$) | Resolution (μm) | Pattern profile | Line size change by PED |
|---|---|---|---|---|---|
| Example 69 | R-25 | 20 | 0.08 | Rectangular | 0 |
| Example 70 | R-32 | 25 | 0.08 | Rectangular | 0 |
| Comparative Example 10 | R-104 | 25 | 0.10 | Somewhat rounded top | +10% |

It is evident from Table 10 that the resist composition of the invention -is also improved in resolution and vacuum PED when processed by EB lithography. The resist composition is expected to perform equally when processed by the EUV or KrF lithography using polyhydroxystyrene derivatives.

Examples 71, 72 & Comparative Examples-11, 12

Evaluation of Sensitivity and Resolution on EUV Exposure

On a HMDS-treated silicon wafer, each of the resist compositions (R-35, R-36) of the invention and comparative resist compositions (R-101, R-102) was spin coated and heat treated at 110° C. for 60 seconds to form a resist film of 50 nm thick. The resist film was exposed on an EUV microstepper (NA 0.3, dipole illumination), post-exposure baked (PEB) at 95° C. for 60 seconds, and developed with a 2.38 wt % TMAH aqueous solution, obtaining a positive pattern.

The resist pattern was evaluated as follows. The optimum exposure (sensitivity, Eop) was defined as the exposure dose ($mJ/cm^2$) which provided a 1:1 resolution at the top and bottom of a 32-nm line-and-space pattern. The resolution of the resist was defined as the minimum line width of a line-and-space pattern that was ascertained separate at the optimum exposure. The results are shown in Table 11.

TABLE 11

|  | Resist composition | Eop ($mJ/cm^2$) | Resolution (nm) |
|---|---|---|---|
| Example 71 | R-35 | 19 | 27 |
| Example 72 | R-36 | 20 | 27 |
| Comparative Example 11 | R-101 | 42 | 29 |
| Comparative Example 12 | R-102 | 40 | 32 |

It is evident from Table 11 that the resist composition comprising the photoacid generator of the invention exhibits a high sensitivity and resolution even when processed by the EUV lithography.

Japanese Patent Application No. 2007-230363 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator for chemically amplified resist compositions which generates a sulfonic acid in response to high-energy radiation selected from UV, deep-UV, EUV, electron beam, x-ray, excimer laser, gamma-ray and synchrotron radiation, said sulfonic acid having the general formula (1a) or (1c):

$$R^1—COOCH(CF_3)CF_2SO_3^-H^+ \quad (1a)$$

$$R^1—O—COOCH(CF_3)CF_2SO_3^-H^+ \quad (1c)$$

wherein $R^1$ is a $C_{20}$-$C_{50}$ hydrocarbon group having a steroid structure.

2. The photoacid generator of claim 1 which generates a sulfonic acid having the following structural formula (1d) or (1e).

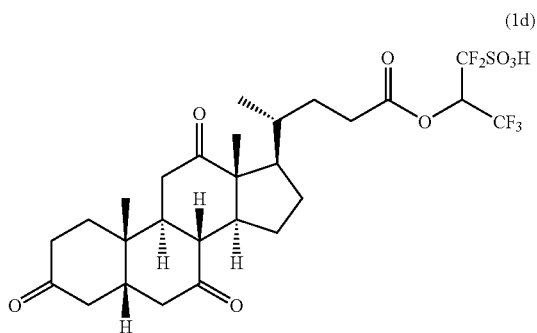
(1d)

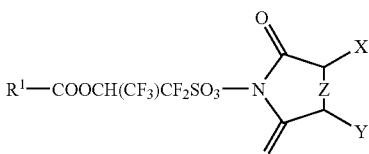
(5a)

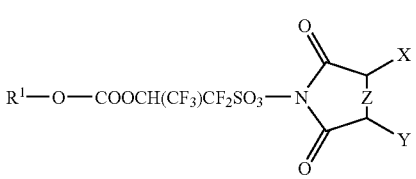
(5c)

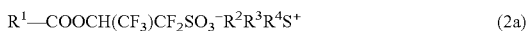
(1e)

3. A sulfonium salt having the general formula (2a) or (2c):

R¹—COOCH(CF₃)CF₂SO₃⁻R²R³R⁴S⁺   (2a)

R¹—O—COOCH(CF₃)CF₂SO₃⁻R²R³R⁴S⁺   (2c)

wherein R¹ is a $C_{20}$-$C_{50}$ hydrocarbon group having a steroid structure, R², R³ and R⁴ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of R², R³ and R⁴ may bond together to form a ring with the sulfur atom.

4. A sulfonium salt having the general formula (3a) or (3c):

R¹—COOCH(CF₃)CF₂SO₃⁻(R⁵(O)ₙ)ₘPh'S⁺Ph₂   (3a)

R¹—O—COOCH(CF₃)CF₂SO₃⁻(R⁵(O)ₙ)ₘPh'S⁺Ph₂   (3c)

wherein R¹ is a $C_{20}$-$C_{50}$ hydrocarbon group having a steroid structure, R⁵ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, Ph denotes phenyl, and Ph' denotes a phenyl group in which a number "m" of hydrogen atoms are substituted by R⁵(O)ₙ— groups.

5. A iodonium salt having the general formula (4a) or (4c):

R¹—COOCH(CF₃)CF₂SO₃⁻((R⁵(O)ₙ)ₘPh')₂I⁺   (4a)

R¹—O—COOCH(CF₃)CF₂SO₃⁻((R⁵(O)ₙ)ₘPh')₂I⁺   (4c)

wherein R¹ is a $C_{20}$-$C_{50}$ hydrocarbon group having a steroid structure, R⁵ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, and Ph' denotes a phenyl group in which a number "m" of hydrogen atoms are substituted by R⁵(O)ₙ— groups.

6. An N-sulfonyloxyimide compound having the general formula (5a) or (5c):

wherein R¹ is a $C_{20}$-$C_{50}$ hydrocarbon group having a steroid structure, X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene or oxygen atom.

7. An oxime sulfonate compound having the general formula (6a) or (6c):

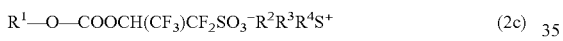
(6a)

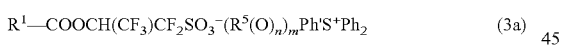
(6c)

wherein R¹ is a $C_{20}$-$C_{50}$ hydrocarbon group having a steroid structure, q is 0 or 1, when q is 0, p is a substituted or unsubstituted $C_1$-$C_{20}$ alkyl group or a substituted or unsubstituted $C_6$-$C_{15}$ aryl group, when q is 1, p is a single bond, a substituted or unsubstituted $C_1$-$C_{20}$ alkylene group or a substituted or unsubstituted $C_6$-$C_{15}$ arylene group, EWG is a cyano, trifluoromethyl, perfluoroethyl, perfluoropropyl, 5H-perfluoropentyl, 6H-perfluorohexyl, nitro or methyl group, and when q is 1, two EWG's may bond together to form a ring of 6 carbon atoms with the carbon atoms to which they are attached.

8. A resist composition comprising a base resin, an acid generator, and an organic solvent, said acid generator comprising a photoacid generator which generates a sulfonic acid having formula (1a) or (1c) as set forth in claim 1.

9. A resist composition comprising a base resin, an acid generator, and an organic solvent, said acid generator comprising a photoacid generator which generates a sulfonic acid having the following structural formula (1d) or (1e) as set forth in claim 2.

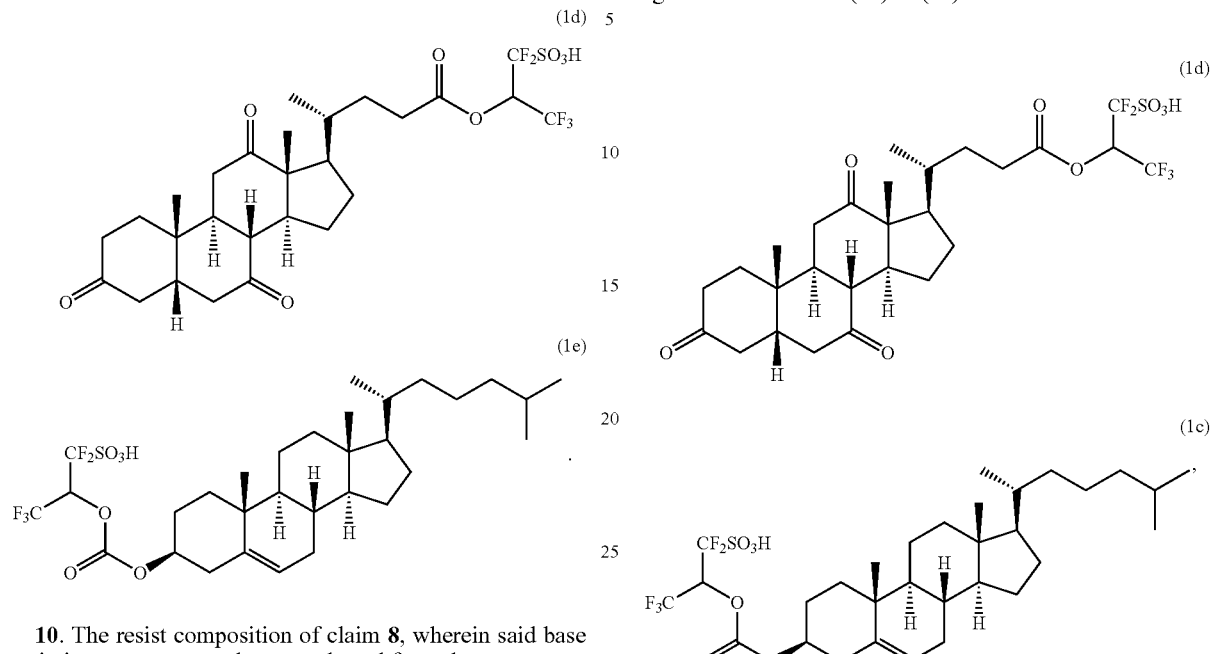

10. The resist composition of claim 8, wherein said base resin is one or more polymers selected from the group consisting of poly(meth)acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers.

11. The resist composition of claim 8, wherein said base resin is a polymeric structure containing silicon atoms.

12. The resist composition of claim 8, wherein said base resin is a polymeric structure containing fluorine atoms.

13. A chemically amplified positive resist composition comprising a base resin as set forth in claim 10, a photoacid generator which generates a sulfonic acid having the general formula (1a) or (1c):

$$R^1\text{—COOCH(CF}_3)\text{CF}_2\text{SO}_3^-\text{—H}^+\text{—} \quad (1a)$$

$$R^1\text{—O—COOCH(CF}_3)\text{CF}_2\text{SO}_3^-\text{—H}^+\text{—} \quad (1c)$$

wherein $R^1$ is a $C_{20}$-$C_{50}$ hydrocarbon group having a steroid structure, and a solvent, wherein said base resin is insoluble or substantially insoluble in a liquid developer, and becomes soluble under the action of the acid.

14. A chemically amplified positive resist composition comprising a base resin as set forth in claim 10, a photoacid generator which generates a sulfonic acid having the following structural formula (1d) or (1e):

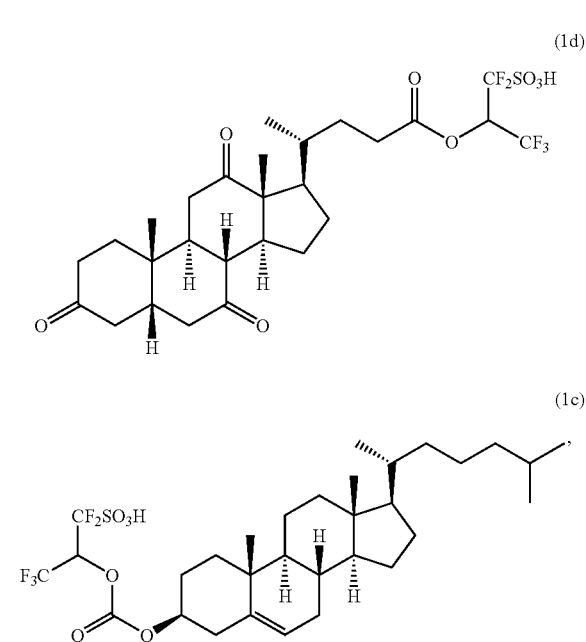

and a solvent, wherein said base resin is insoluble or substantially insoluble in a liquid developer, and becomes soluble under the action of the acid.

15. The chemically amplified positive resist composition of claim 13, further comprising a quencher.

16. The chemically amplified positive resist composition of claim 13, further comprising a dissolution inhibitor.

17. A process for forming a pattern comprising the steps of:
applying the resist composition of claim 8 onto a substrate to form a coating,
heat treating the coating and exposing it to high-energy radiation having a wavelength of up to 300 nm through a photomask, and
optionally heat treating and developing the exposed coating with a developer.

18. The process of claim 17, wherein the exposing step relies on immersion lithography comprising directing radiation from an ArF excimer laser having a wavelength of 193 nm through a projection lens, with a liquid such as water, glycerin or ethylene glycol intervening between the coated substrate and the projection lens.

* * * * *